United States Patent
Yee et al.

(10) Patent No.: US 12,173,317 B2
(45) Date of Patent: Dec. 24, 2024

(54) USE OF HISTONE MODIFIERS TO REPROGRAM EFFECTOR T CELLS

(71) Applicant: Board of Regents, The University of Texas System, Austin, TX (US)

(72) Inventors: Cassian Yee, Houston, TX (US); Junmei Wang, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1060 days.

(21) Appl. No.: 17/042,022

(22) PCT Filed: Mar. 28, 2019

(86) PCT No.: PCT/US2019/024693
§ 371 (c)(1),
(2) Date: Sep. 25, 2020

(87) PCT Pub. No.: WO2019/191501
PCT Pub. Date: Oct. 3, 2019

(65) Prior Publication Data
US 2021/0189337 A1 Jun. 24, 2021

Related U.S. Application Data

(60) Provisional application No. 62/649,265, filed on Mar. 28, 2018.

(51) Int. Cl.
*C12N 5/0783* (2010.01)
*A61K 35/17* (2015.01)
(52) U.S. Cl.
CPC ............ *C12N 5/0636* (2013.01); *A61K 35/17* (2013.01); *C12N 2501/065* (2013.01); *C12N 2501/2321* (2013.01); *C12N 2506/11* (2013.01)

(58) Field of Classification Search
CPC ............ C12N 5/0636; C12N 2501/065; C12N 2501/2321; C12N 2506/11; A61K 35/17; A61K 39/4611; A61K 39/464491; A61K 45/06; A61P 35/00
See application file for complete search history.

(56) References Cited

U.S. PATENT DOCUMENTS

2006/0269973 A1 11/2006 Yee
2015/0023938 A1 1/2015 Yee

FOREIGN PATENT DOCUMENTS

WO  WO 2015-164675  10/2015
WO  WO 2017-219150  12/2017
(Continued)

OTHER PUBLICATIONS

Miltenyi T cell Activation/Expansion kit product page (Year: 2018).*
(Continued)

*Primary Examiner* — Jeremy C Flinders
*Assistant Examiner* — Thomas R. Amick
(74) *Attorney, Agent, or Firm* — Parker Highlander PLLC

(57) ABSTRACT

The present disclosure provides methods for re-programming effector T cells to a central memory phenotype comprising culturing the effector T cells with a histone deacetylase inhibitor (HDACi) and IL-21. Further provided are methods of treating cancer comprising administering the central memory T cells.

23 Claims, 46 Drawing Sheets
Specification includes a Sequence Listing.

(56) References Cited

FOREIGN PATENT DOCUMENTS

| WO | WO 2019/173636 | 9/2019 |
| WO | WO 2020/051374 | 3/2020 |

OTHER PUBLICATIONS

Huang, et al. Oncotarget vol. 8,2 (2017): 2694-2707) (Year: 2017).*
Mahnke et al. Eur J Immunol. 2013;43(11):2797-2809 (Year: 2013).*
Kroesen (Kroesen, Michiel et al. "HDAC inhibitors and immunotherapy; a double edged sword?." Oncotarget vol. 5, 16 (2014): 6558-72.). (Year: 2014).*
McCaw et al., "Modulation of antitumor immunity with histone deacetylase inhibitors," Immunotherapy, 9(16):1359-1372, 2017.
Office Action issued in Japanese Application No. 2020-551874, mailed Feb. 21, 2023, and English translation thereof.
Sodre et al., "Epigenetic reprogramming of immune cells through selective inhibition of HDAC6 reduces suppressive phenotypes and augments anti-tumor properties of T-cells," In: Proceedings of the American Association for Cancer Research Annual Meeting, Cancer Res, 77(13 Suppl): Abstract 638, 2017.
Agarwal et al., "Gene regulation and chromatin remodeling by IL-12 and type I IFN in programming for CD8 T cell effector function and memory," The Journal of Immunology, 183:1695-1704, 2009.
Bae et al., "Histone deacetylase (HDAC) inhibitor ACY241 enhances anti-tumor activities of antigen-specific central memory cytotoxic T lymphocytes against multiple myeloma and solid tumors," Leukemia, 32(9):1932-1947, 2018.
Extended European Search Report issued in European Application No. 19775917.8, mailed Dec. 3, 2021.
Ho et al., "The road to memory: an early rest for the long journey," J Immunol., 191(11):5603-5614, 2013.
Kaka et al., "Genetic modification of T cells with IL-21 enhances antigen presentation and generation of central memory tumor-specific cytotoxic T-lymphocytes," J Immunother, 32(7):726-736, 2009.
Klebanoff et al., "Central memory self/tumor-reactive CD8+ T cells confer superior antitumor immunity compared with effector memory T cells," Proc Natl Acad Sci U S A, 102(27):9571-9576, 2005.
Laino et al., "Targeting histone deacetylase 6 in T-cells to improve melanoma immunotherapy," In Proceedings of the AACR Special Conference: Tumor Immunology and Immunotherapy; Cancer Immunol Res., Abstract PR09, 3(10 Supplement), 2015.
Li et al., "IL-21 influences the frequency, phenotype, and affinity of the antigen-specific CD8 T cell response," J. Immunol., 175(4):2261-2269, 2005.
Loschinski et al., "IL-21 modulates memory and exhaustion phenotype of T-cells in a fatty acid oxidation-dependent manner," Oncotarget, 9(17):13125-13138, 2018.
PCT International Preliminary Report on Patentability issued in International Application No. PCT/US2019/024693, mailed Sep. 29, 2020.
PCT International Search Report and Written Opinion issued in International Application No. PCT/US2019/024693, mailed Jun. 20, 2019.
Wang et al., "Histone deacetylase inhibitors and IL21 cooperate to reprogram human effector CD8 + T cells to memory T cells," Cancer Immunology Research, 8(6):794-805, 2020.
Weber et al., "A critical role for TCF-1 in T-lineage specification and differentiation," Nature, 476(7358):63-68, 2011.
Yee, "The use of endogenous T cells for adoptive transfer," Immunol. Rev., 257(1):250-263, 2014.
Zhang et al., "Epigenetic manipulation restores functions of defective CD8+ T cells from chronic viral infection," Molecular Therapy, 22(9):1698-1706, 2014.
Office Action issued in European Application No. 19775917.8, mailed Aug. 28, 2024.

* cited by examiner

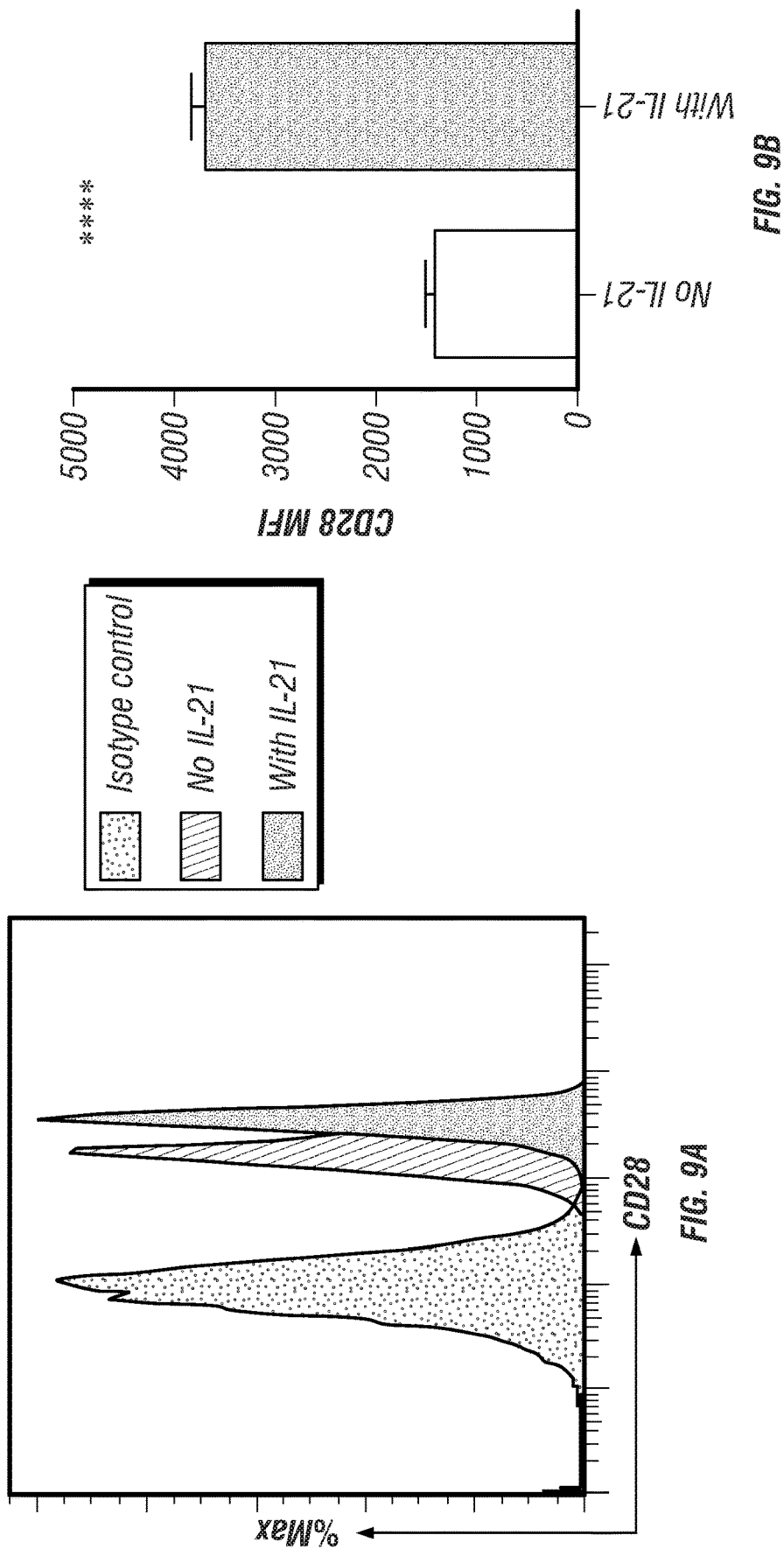

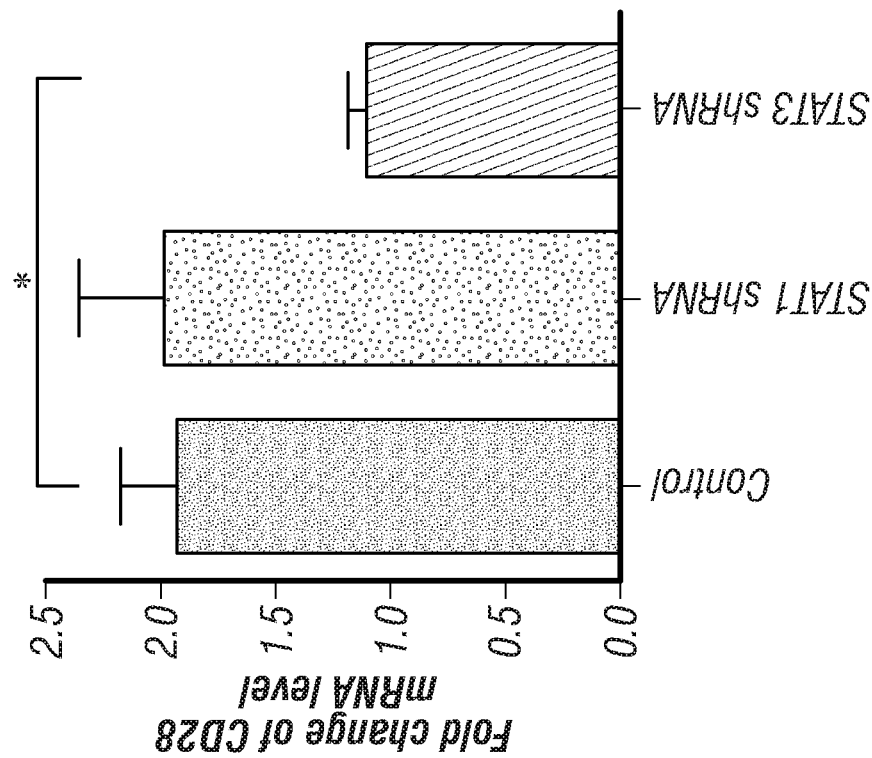
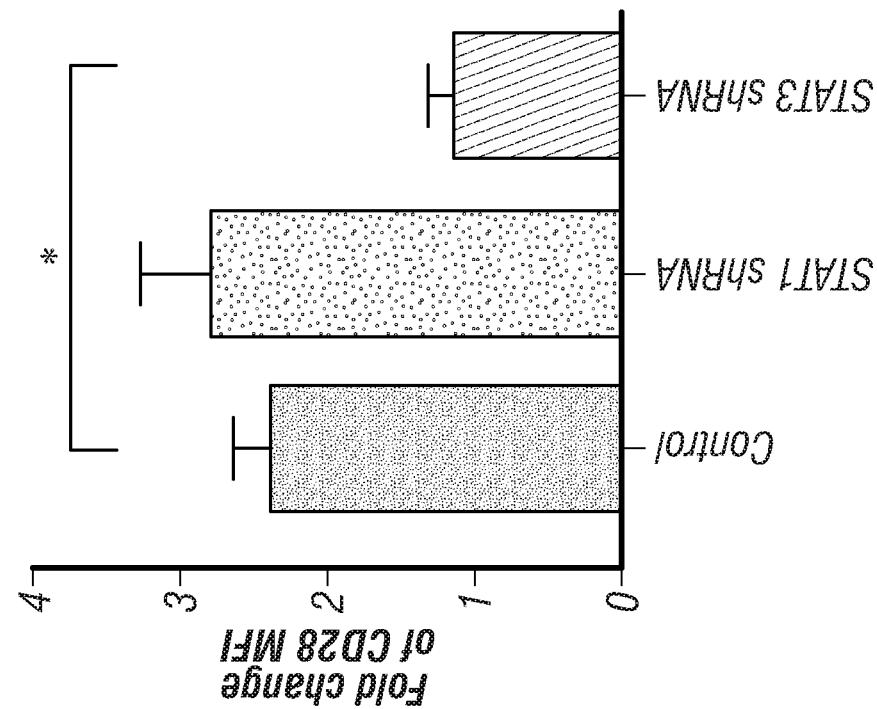
FIG. 10F
FIG. 10E

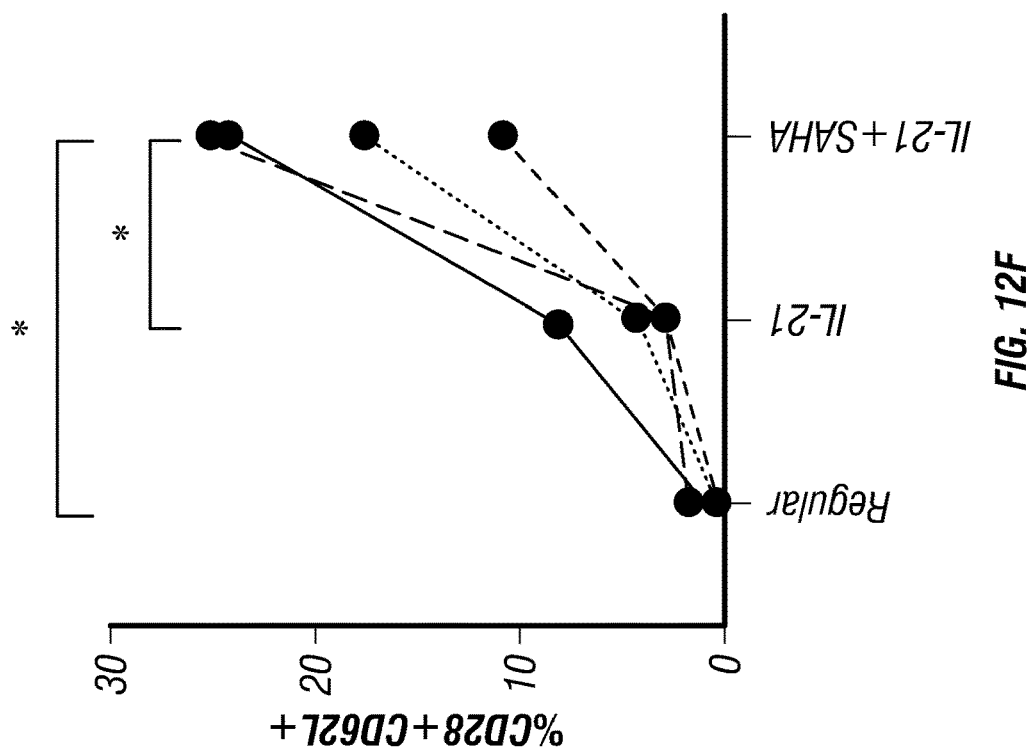
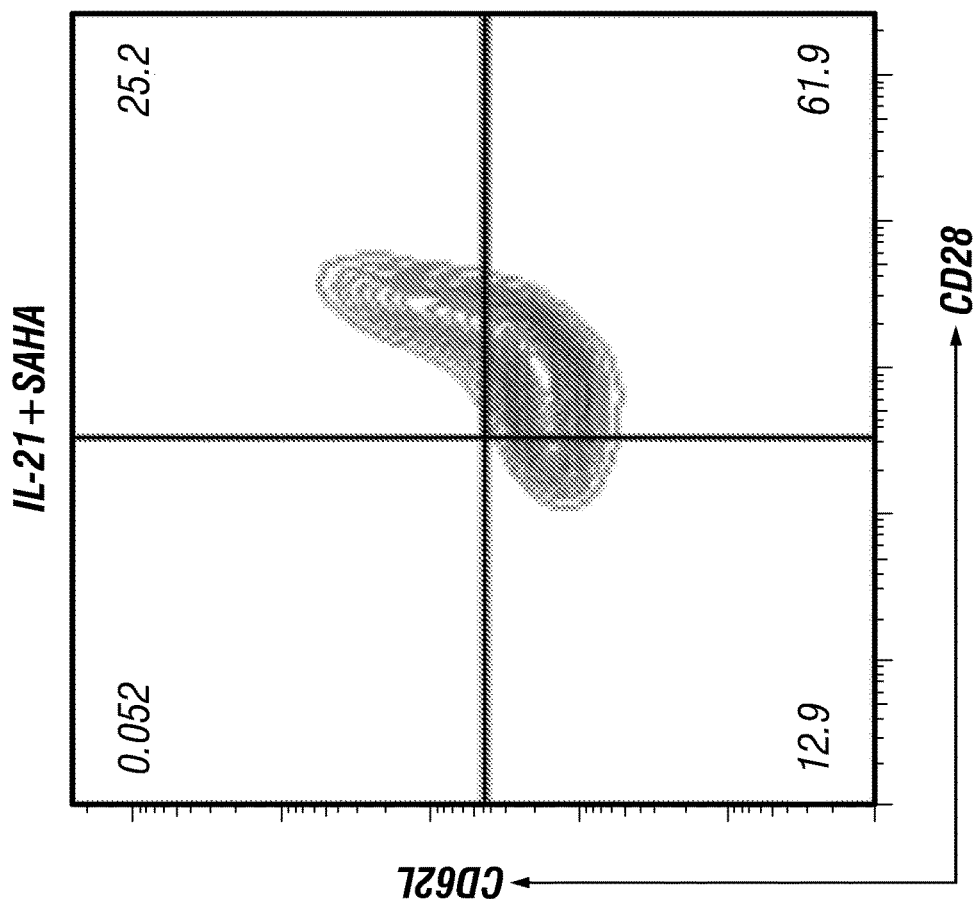
FIG. 12E (Cont'd)
FIG. 12F

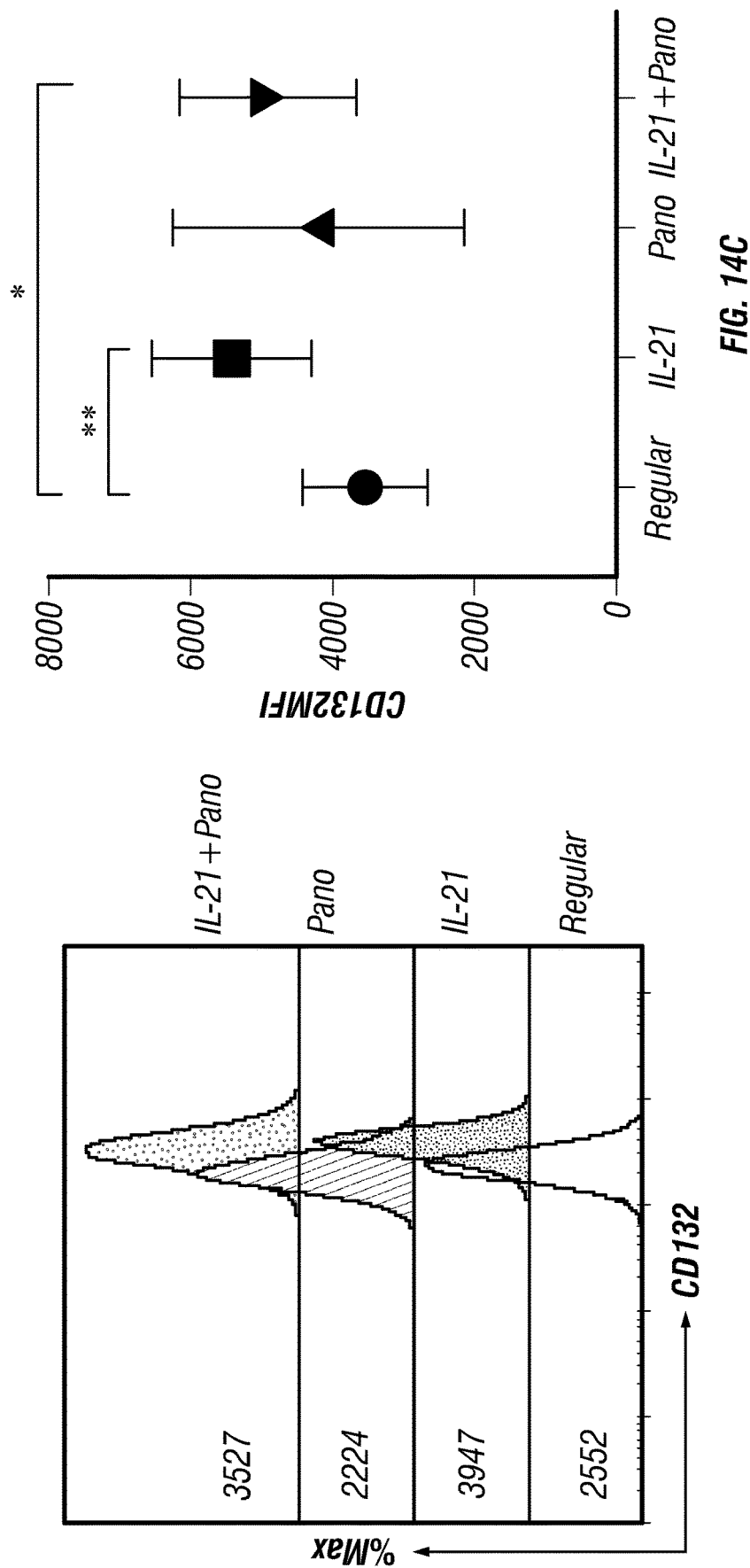

USE OF HISTONE MODIFIERS TO REPROGRAM EFFECTOR T CELLS

This application is a national phase application under 35 U.S.C. § 371 of International Application No. PCT/US2019/024693, filed Mar. 28, 2019, which claims the benefit of U.S. Provisional Patent Application No. 62/649,265, filed Mar. 28, 2018, each of which is incorporated herein by reference in its entirety.

INCORPORATION OF SEQUENCE LISTING

The sequence listing that is contained in the file named "UTFC.P1311WO_ST25.txt", which is 3.81 KB (as measured in Microsoft Windows) and was created on Mar. 28, 2019 is filed herewith by electronic submission and is incorporated by reference herein.

FIELD

The present invention relates generally to the fields of medicine and immunology. More particularly, it concerns methods of generating T cells with a central memory phenotype.

BACKGROUND

Adoptive T cell therapy (ACT), the administration of ex vivo activated and expanded autologous tumor-specific T lymphocytes has been shown to induce clinical responses in metastatic melanoma patients previously refractory to conventional therapy. Patient response rate correlates with persistence of the infused T cells in vivo. Often, however, antigen-specific T cells found in the peripheral blood and tumor sites are well-differentiated effector, effector memory, and sometimes terminal effector cells with very limited proliferative ability. Central memory $CD8^+$ T cells are capable of self-renewal and highly express costimulatory receptor CD28 and other memory-associated markers (e.g., CD127 and CD62L) (Klebanoff et al., 2005). Thus, there is an unmet need for methods to generate central memory T cells capable of self-renewal from well-differentiated effector cells. These T cells with a central memory phenotype could be used for ACT with a high response rate due to their increased persistence in vivo.

SUMMARY

Certain embodiments of the present disclosure provide methods (e.g., in vitro or ex vivo) for generating T cells with a central memory phenotype from T cells with an effector phenotype, such as by re-programming or de-differentiation.

In one embodiment, there is provided a method for reprogramming antigen-specific effector T cells ($T_{EFF}$ cells) into central memory T cells ($T_{CM}$ cells), the method comprising obtaining a starting population of lymphocytes comprising $T_{EFF}$ cells from a subject; optionally preparing a sample enriched in $T_{EFF}$ cells from the starting population of lymphocytes comprising $T_{EFF}$ cells; and culturing the starting population of lymphocytes comprising $T_{EFF}$ cells or the sample enriched in $T_{EFF}$ cells in the presence of a histone deacetylase inhibitor (HDACi) and interleukin-21 (IL-21), each in an amount sufficient to re-program the $T_{EFF}$ cells into $T_{CM}$ cells, wherein the re-programming produces a population of lymphocytes enriched for $T_{CM}$ cells as compared to the number of $T_{CM}$ cells in the starting population of lymphocytes comprising $T_{EFF}$ cells obtained from a subject.

In some aspects, obtaining a starting population of lymphocytes comprising $T_{EFF}$ cells comprises taking a sample of tumor infiltrating lymphocytes (TILs) or a sample comprising peripheral blood mononuclear cells (PBMCs) from a subject. In additional aspects, the method further comprises the step of preparing a sample enriched in $T_{EFF}$ cells from the starting population of lymphocytes comprising $T_{EFF}$ cells. In some aspects, the step of preparing a sample enriched in $T_{EFF}$ cells from the starting population of lymphocytes comprising $T_{EFF}$ cells comprises isolating $CD8^+$ $T_{EFF}$ cells from the starting population of lymphocytes comprising $T_{EFF}$ cells.

In certain aspects, the step of preparing a sample enriched in $T_{EFF}$ cells from the starting population of lymphocytes comprising $T_{EFF}$ cells further comprises depleting the starting population of lymphocytes comprising $T_{EFF}$ cells of myeloid-derived suppressor cells (MDSCs), $T_{REGs}$, NK cells, and macrophages. In some aspects, the step of preparing a sample enriched in $T_{EFF}$ cells from the starting population of lymphocytes comprising $T_{EFF}$ cells comprises depleting the starting population of lymphocytes comprising $T_{EFF}$ cells of myeloid-derived suppressor cells (MDSCs), $T_{REGs}$, NK cells, and macrophages. In some aspects, the step of preparing a sample enriched in $T_{EFF}$ cells from the starting population of lymphocytes comprising $T_{EFF}$ cells further comprises isolating $CD8^+$ $T_{EFF}$ cells from the starting population of lymphocytes comprising $T_{EFF}$ cells.

In some aspects, the $CD8^+$ $T_{EFF}$ cells express CD45RO. In certain aspects, the $CD8^+$ $T_{EFF}$ cells have high expression of CD45RO. In particular aspects, positive, high, or low expression of a cell surface marker, antigen or protein is defined relative to the expression level of said cell surface marker, antigen or protein in a control population. In particular aspects the control population is a population negative for or with an undetectable level of a cell surface marker, antigen or protein. In some aspects the control population is in the same sample as the population with positive, high or low expression. In other aspects the control population is in a sample substantially similar to the sample containing the population with positive, high or low expression. For example, high expression of CD45RO in $CD8^+$ $T_{EFF}$ cells can be defined as an elevated expression level relative to the expression level of CD45RO in $CD8^+$ $T_{EFF}$ cells of a control population. Relative expression level may be measured as the relative fluorescence signal of a cell surface marker, antigen or protein, in particular as measured by flow cytometry.

In particular instances, high expression of a cell surface marker, antigen or protein may correspond to a 2, 3, 4, 5, 6, 7, 8, 9 or 10 (or any value derivable therein) times greater expression than the expression level determined in a low expression population. Specifically, high expression of a cell surface marker, antigen or protein may correspond to a 2, 3, 4, 5, 6, 7, 8, 9 or 10 (or any value derivable therein) times greater fluorescence signal relative to the fluorescence signal of a control cell population. A control cell population may be a cell population with low, undetectable, or normal expression of a cell surface marker, antigen, or protein. In other instances, high expression of a cell surface marker, antigen or protein may correspond to a 20, 30, 40, 50, 60, 70, 80, 90, 100, 200, 300, 400, 500, 1000 or 10,000 (or any value derivable therein) times greater expression than the expression level determined in a low expression population. High expression of a cell surface marker, antigen or protein may correspond to a 20, 30, 40, 50, 60, 70, 80, 90, 100, 200, 300, 400, 500, 1000 or 10,000 (or any value derivable therein) times greater fluorescence signal relative to the fluorescence signal of a control cell population.

Low expression of a cell surface marker, antigen or protein may correspond to a 2, 3, 4, 5, 6, 7, 8, 9 or 10 (or any value derivable therein) times greater fluorescence signal relative to the fluorescence signal corresponding to an expression level of negative or not detectable for said surface marker or antigen. Low expression of a cell surface marker, antigen or protein may correspond to a 20, 30, 40, 50, 60, 70, 80, 90, 100, 200, 300, 400, 500, 1000 or 10,000 (or any value derivable therein) times greater fluorescence signal relative to the fluorescence signal corresponding to an expression level of negative or not detectable for said surface marker or antigen.

Positive expression refers to an expression level of a cell surface marker, antigen or protein that is detectable by a given detection methods, such as detection of a fluorescence signal. As used herein, both high and low expression levels may be considered positive expression.

In certain aspects, the CD8$^+$ T$_{EFF}$ cells are cultured in the presence of an HDACi prior to adding IL-21. In particular aspects, the CD8$^+$ T$_{EFF}$ cells are cultured in the presence of an HDACi for 12 to 48 hours (e.g., 12-15, 15-20, 20-25, 25-30, 30-35, 35-40, or 40-48 hours) prior to adding IL-21. In certain aspects, the CD8$^+$ T$_{EFF}$ cells are cultured in the presence of an HDACi for 1 to 3 days (e.g., 1, 2, or 3 days) prior to adding IL-21. In specific aspects, the CD8$^+$ T$_{EFF}$ cells are cultured in the presence of IL-21 prior to adding an HDACi. In some aspects, the CD8$^+$ T$_{EFF}$ cells are cultured in the presence of IL-21 for 12 to 48 hours (e.g., 12-15, 15-20, 20-25, 25-30, 30-35, 35-40, or 40-48 hours) prior to adding an HDACi. In particular aspects, the CD8$^+$ T$_{EFF}$ cells are cultured in the presence of IL-21 for 1 to 3 days, such as 1, 2, or 3 days, prior to adding an HDACi. In some aspects, the CD8$^+$ T$_{EFF}$ cells are simultaneously cultured in the presence of an HDACi and IL-21. In certain aspects, the culturing is for 7 to 20 days (e.g., 8, 9, 10, 11, 12, 13, 14, 15, 16, 17, 18, 19, or 20 days). In some aspects, the culturing is for 12 to 16 days (e.g., 12, 13, 14, 15, or 16 days). In specific aspects, the IL-21 is present at a concentration of 10 ng/mL to 50 ng/mL (e.g., 10-20, 20-30, 30-40, or 40-50 ng/mL). In particular aspects, the IL-21 is present at a concentration of 20 ng/mL to 40 ng/mL (e.g. 20-25, 25-30, 30-35, or 35-40 ng/mL). In some aspects, the HDACi is present at a concentration of 1 nM to 5 nM (e.g., 1-2, 2-3, 3-4, or 4-5 nM). In particular aspects, the HDACi is present at a concentration of 2 nM of 4 nM (e.g., 2, 3, or 4 nM). In some aspects, the IL-21 is present at a concentration of 10 ng/mL to 50 ng/mL (e.g., 10-20, 20-30, 30-40, or 40-50 ng/mL) and the HDACi is present at a concentration of 1 nM to 5 nM (e.g., 1-2, 2-3, 3-4, or 4-5 nM). In certain aspects, the IL-21 is present at a concentration of 20 ng/mL to 40 ng/mL (e.g. 20-25, 25-30, 30-35, or 35-40 ng/mL) and the HDACi is present at a concentration of 2 nM of 4 nM (e.g., 2, 3, or 4 nM).

In certain aspects, the HDACi is a classical HDACi. In some aspects, the classical HDACi is selected from the group consisting of trichostatin A, trapoxin B, phenylbutyrate, valproic acid, vorinostat (suberanilohydroxamic acid or SAHA, marketed as ZOLINZA®), belinostat (PXD101, marketed as BELEODAQ®), panobinostat (marketed as FARYDAQ®), dacinostat (LAQ824), entinostat (SNDX-275 or MS-275), tacedinaline (CI994), and mocetinostat (MGCD0103). In particular aspects, the HDACi is SAHA. In other aspects, the HDAC is panobinostat.

In some aspects, the resulting T$_{CM}$ cells are CD8$^+$ and also express at least two of CD45RO, CD28, CD62L, and CCR7. In some aspects, the resulting T$_{CM}$ cells are CD8$^+$ and have high expression of at least two of CD45RO, CD28, CD62L, and CCR7. In certain aspects, the resulting T$_{CM}$ cells are CD8$^+$ and also express at least three of CD45RO, CD28, CD62L, and CCR7 (i.e., are CD8$^+$/CD45RO$^+$/CD28$^+$/CD62L+/CCR7$^+$). In some aspects, the resulting T$_{CM}$ cells are CD8$^+$ and also have high expression of CD45RO, CD28, CD62L, and CCR7. In certain aspects, the resulting T$_{CM}$ cells also express increased levels of granzyme B and perforin 1.

In additional aspects, the method further comprises a step of expanding the T$_{CM}$ cells. In some aspects, the expanding comprises treating the T$_{CM}$ cells with at least one of anti-CD3, anti-CD28, and anti-CD137/4-1BB. In certain aspects, the expanding comprises treating the T$_{CM}$ cells with anti-CD3 and anti-CD28. In specific aspects, the expanding comprises treating the T$_{CM}$ cells with anti-CD3, anti-CD28, and anti-CD137/4-1BB.

In further aspects, the method further comprises a step of contacting the starting population of lymphocytes comprising T$_{EFF}$ cells or the sample enriched in T$_{EFF}$ cells with IL-2 prior to or concurrently with the step of culturing the starting population of lymphocytes comprising T$_{EFF}$ cells or the sample enriched in T$_{EFF}$ cells in the presence of an HDACi and IL-21, each in an amount sufficient to re-program the T$_{EFF}$ cells into T$_{CM}$ cells. In some aspects, the population of lymphocytes enriched for T$_{CM}$ cells comprises at least 5-fold (e.g., 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-fold or higher) more T$_{CM}$ cells than in the starting population of lymphocytes comprising T$_{EFF}$ cells. In certain aspects, the population of lymphocytes enriched for T$_{CM}$ cells comprises at least 10-fold more T$_{CM}$ cells than in the starting population of lymphocytes comprising T$_{EFF}$ cells. In specific aspects, the population of lymphocytes enriched for T$_{CM}$ cells comprises at least 30-fold more T$_{CM}$ cells than in the starting population of lymphocytes comprising T$_{EFF}$ cells. In some aspects, the population of lymphocytes enriched for T$_{CM}$ cells display increased proliferation in response to treatment with IL-2 and/or IL-15 compared to the starting population of lymphocytes comprising T$_{EFF}$ cells in response to treatment with IL-2 and/or IL-15.

In another embodiment, there is provided a pharmaceutical composition comprising the population of lymphocytes enriched for T$_{CM}$ cells produced according to the embodiments (e.g., obtaining a starting population of lymphocytes comprising T$_{EFF}$ cells from a subject; optionally preparing a sample enriched in T$_{EFF}$ cells from the starting population of lymphocytes comprising T$_{EFF}$ cells; and culturing the starting population of lymphocytes comprising T$_{EFF}$ cells or the sample enriched in T$_{EFF}$ cells in the presence of a histone deacetylase inhibitor (HDACi) and interleukin-21 (IL-21), each in an amount sufficient to re-program the T$_{EFF}$ cells into T$_{CM}$ cells, wherein the re-programming produces a population of lymphocytes enriched for T$_{CM}$ cells as compared to the number of T$_{CM}$ cells in the starting population of lymphocytes comprising T$_{EFF}$ cells obtained from a subject). Further provided herein is a pharmaceutical composition of the embodiments for use in the treatment of cancer.

A further embodiment provides the use of a therapeutically effective amount of the population of lymphocytes enriched for T$_{CM}$ cells produced according to the embodiments (e.g., obtaining a starting population of lymphocytes comprising T$_{EFF}$ cells from a subject; optionally preparing a sample enriched in $T_{EFF}$ cells from the starting population of lymphocytes comprising $T_{EFF}$ cells; and culturing the starting population of lymphocytes comprising $T_{EFF}$ cells or the sample enriched in $T_{EFF}$ cells in the presence of a histone deacetylase inhibitor (HDACi) and interleukin-21 (IL-21), each in an amount sufficient to re-program the $T_{EFF}$ cells into $T_{CM}$ cells, wherein the re-programming produces a population of lymphocytes enriched for $T_{CM}$ cells as compared to the number of $T_{CM}$ cells in the starting population of lymphocytes comprising $T_{EFF}$ cells obtained from a subject) for the treatment of cancer.

In another embodiment, there is provided a composition comprising a therapeutically effective amount of the population of lymphocytes enriched for $T_{CM}$ cells produced by the methods of the embodiments (e.g., obtaining a starting population of lymphocytes comprising $T_{EFF}$ cells from a subject; optionally preparing a sample enriched in $T_{EFF}$ cells from the starting population of lymphocytes comprising $T_{EFF}$ cells; and culturing the starting population of lymphocytes comprising $T_{EFF}$ cells or the sample enriched in $T_{EFF}$ cells in the presence of a histone deacetylase inhibitor (HDACi) and interleukin-21 (IL-21), each in an amount sufficient to re-program the $T_{EFF}$ cells into $T_{CM}$ cells, wherein the re-programming produces a population of lymphocytes enriched for $T_{CM}$ cells as compared to the number of $T_{CM}$ cells in the starting population of lymphocytes comprising $T_{EFF}$ cells obtained from a subject) for the treatment of cancer in a subject.

A further embodiment provides a method of treating cancer in a subject comprising administering a therapeutically effective amount of the population of lymphocytes enriched for $T_{CM}$ cells produced by the methods of the embodiment or the pharmaceutical composition of the embodiments to the subject. In some aspects, the method further comprises a step of performing lymphodepletion on the subject prior to administration of the therapeutically effective amount of the population of lymphocytes enriched for $T_{CM}$ cells. In certain aspects, the therapeutically effective amount of the population of lymphocytes enriched for $T_{CM}$ cells is derived from a sample of autologous tumor infiltrating lymphocytes (TILs) having antitumor activity. In some aspects, the population of lymphocytes enriched for $T_{CM}$ cells is administered to the subject intravenously, intraperitoneally, or intratumorally. In particular aspects, the subject is a human.

In additional aspects, the method further comprises the step of administering at least one additional therapeutic agent to the subject. In some aspects, the at least one additional therapeutic agent is selected from the group consisting of chemotherapy, radiotherapy, and immunotherapy. In particular aspects, the at least one additional therapeutic agent is an immunotherapy. In specific aspects, the immunotherapy is an immune checkpoint inhibitor. In some aspects, the immune checkpoint inhibitor inhibits an immune checkpoint protein or ligand thereof selected from the group consisting of CTLA-4, PD-1, PD-L1, PD-L2, LAG-3, BTLA, B7H3, B7H4, TIM3, KIR, or adenosine A2a receptor (A2aR). In particular aspects, the immune checkpoint inhibitor inhibits PD-1. In certain aspects, the immune checkpoint inhibitor inhibits CTLA-4.

In yet another embodiment, there is provided a method for generating $T_{CM}$ cells from $T_{EFF}$ cells comprising obtaining a starting population of lymphocytes comprising $T_{EFF}$ cells from a subject; simultaneously adding an HDACi at a concentration between 2 nM and 4 nM and IL-21 at a concentration between 20 ng/mL and 40 ng/mL to the starting population of lymphocytes comprising $T_{EFF}$ cells; and culturing the starting population of lymphocytes comprising $T_{EFF}$ cells for 12 to 16 days, thereby re-programming the $T_{EFF}$ cells to produce a population of lymphocytes enriched for $T_{CM}$ cells as compared to the number of $T_{CM}$ cells in the starting population of lymphocytes comprising $T_{EFF}$ cells.

In another embodiment, there is provided a composition comprising a population of human central memory-like $CD8^+$ T cells, wherein at least 20% (e.g., at least 25%, 26%, 27%, 28%, 29%, 30%, 35%, 40%, 45%, 50%, 55%, 60%, 65%, 70%, or higher) of the T cells are $CD28^+CD62L^+CD127^-CCR7^-$ T cells of have high expression of CD28 and CD62L along with low expression of CD127 and CCR7. In some aspects, at least 50% or 60% of the T cells are $CD28^+CD62L^+CD127^-CCR7^-$ T cells. In certain aspects, the $CD28^+CD62L^+CD127^-CCR7^-$ T cells further express or have high expression of Lef1 and/or Tcf1. In particular aspects, the $CD28^+CD62L^+CD127^-CCR7^-$ T cells have essentially no CD45RA and/or CD45RO expression. In some aspects, the $CD28^+CD62L^+CD127^-CCR7^-$ T cells have low CD45RA and/or CD45RO expression.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 9A-9F: IL-21 upregulates CD28 expression in activated human naïve $CD8^+$ T cells. (A) Representative histogram of CD28 surface level on M27-specific $CD8^+$ T cells and the isotype control antibody was used as a negative staining control. (B) MFI of CD28 protein levels on the surface of M27-specific $CD8^+$ T cells. (n=12, mean±SEM, **** $p<0.0001$, unpaired t test). MFI: mean fluorescence intensity. (C) Representative histogram of CD28 surface level on human naïve $CD8^+$ T cells stained on day7 after activation. The isotype control antibody was used as a negative staining control. (D) MFI of CD28 protein levels on the surface of $CD8^+$ T cells activated with the indicated conditions for 7 days. (n=4, mean±SEM, * $p<0.05$, paired t test). (E) The quantitative RT-PCR results of CD28 mRNA levels in sort-purified human Mart1 (M27)-specific $CD8^+$ T cells generated with or without IL-21. The expression level in cells expanded without IL-21 was set as 1. (n=2, mean±SEM,  $p<0.01$, unpaired t test). (F) The quantitative RT-PCR results of CD28 mRNA levels in human $CD8^+$ T cells activated with the indicated conditions for 7 days. The expression level in cells activated with anti-CD3/CD28 beads for 7 days was set as 1. (n=6, mean±SEM,  $p<0.01$, paired t test). Results of quantitative RT-PCR for CD28 gene were normalized to RPL13A. The results in A, B, and E were representative out of 2 (E) or 3 (A-B) independent experiments using cells from different healthy donors. Panel C was representative from 4 independent experiments using cells from different healthy donors. The results in D and F were pooled from 4 (D) or 6 (F) independent experiments using cells from different healthy donors.

FIGS. 10A-10G: STAT3 activation is essential for IL-21-induced CD28 upregulation. (A) Representative histograms of CD28 surface level on activated human $CD8^+$ T cells from healthy donors or Job's syndrome patients. HD: healthy donor. (B) Fold change of CD28 MFI, which is presented as fold of MFI of cells activated with anti-CD3/CD28 and IL-21 over MFI of cells activated with only anti-CD3/CD28. (n=3, mean±SEM, * $p<0.05$, unpaired t test). (C) Fold change of quantitative RT-PCR results of CD28 mRNA levels in human $CD8^+$ T cells from healthy donors or Job's syndrome patients activated with anti-CD3/CD28 or together with IL-21 for 7 days. The expression level in cells from healthy donor or Job's syndrome patient activated with anti-CD3/28 beads alone for 7 days was set as 1. (n=3, mean±SEM, ** $p<0.01$, unpaired t test). (D) Representative histograms of CD28 surface level on human $CD8^+$ T cells transfected with control, STAT1 or STAT3 shRNAs and activated with the indicated conditions for 7 days. (E) Fold change of CD28 MFI on the surface of negative control (Control) or STAT-knockdown $CD8^+$ T cells activated with the indicated conditions for 7 days. Data is presented as fold of MFI of cells activated with anti-CD3/CD28 and IL-21 over MFI of cells activated with only anti-CD3/CD28. (n=6, mean±SEM, * $p<0.05$, one-way ANOVA). (F) Fold change of quantitative PCR results of CD28 mRNA levels in human $CD8^+$ T cells transfected with control, STAT1 or STAT3 shRNAs and activated with anti-CD3/CD28 or together with IL-21 for 7 days. The expression level in cells activated with CD3/28 beads alone for 7 days was set as 1. (n=4, mean±SEM, * $p<0.05$, one-way ANOVA). (G) ChIP results of STAT3 binding to the proximal and distal STAT sites on the human CD28 promoter. (n=6, mean±SEM,  $p<0.01$, * $p<0.001$, two-way ANOVA). The results were representative (A, D, G) or pooled from 3 (B, C, G), 4 (F), or 6 (E) independent experiments using cells from different donors.

[n=3; mean±SEM;  p<0.01, * p<0.001; two-way ANOVA]. The results were representative out of two (C, E, F) or three (A, D), or pooled from 3 (B) independent experiments using cells from different donors.

FIGS. 12A-12F: SAHA allows IL-21-induced pSTAT3 to access the CD28 promoter and to upregulate CD28 expression in effector CD8$^+$ T cells. (A) ChIP results of H3 acetylation level on the CD28 promoter for M27-specific effector CD8$^+$ T cells left untreated (None) or treated with SAHA for 24 hours. [n=3; mean±SEM; *** p<0.001; two-way ANOVA]. (B) ChIP results of STAT3 binding to the CD28 promoter for M27-specific effector CD8$^+$ T cells left untreated or treated with SAHA for 24 hours, followed by IL-21 stimulation for 30 minutes. [n=3; mean±SEM; ns: not significant, * p<0.05, ** p<0.01; two-way ANOVA]. (C) Representative histogram of CD28 levels on CTLs treated with the indicated conditions for 4 days. The numbers inside the histogram graph show the representative CD28 MFI for each condition and the vertical line separates CD28$^-$ and CD28$^+$ populations. (D) MFI of CD28 on CTLs from independent experiments (n=4; mean±SEM; * p<0.05; one-way ANOVA, comparing IL-2+SAHA to the other conditions). (E) Representative plots of CD28 and CD62L levels on TILs expanded with the indicated conditions for 2 weeks. The numbers within the plots annotate the percentage of cells in each quadrant. (F) Percentage of CD28$^+$CD62L$^+$ cells in TILs expanded with the indicated conditions from independent experiments (n=4; * p<0.05; one-way ANOVA). The representative results out of two (B), three (A), or four (C, E) independent experiments are shown.

Figure 13A:
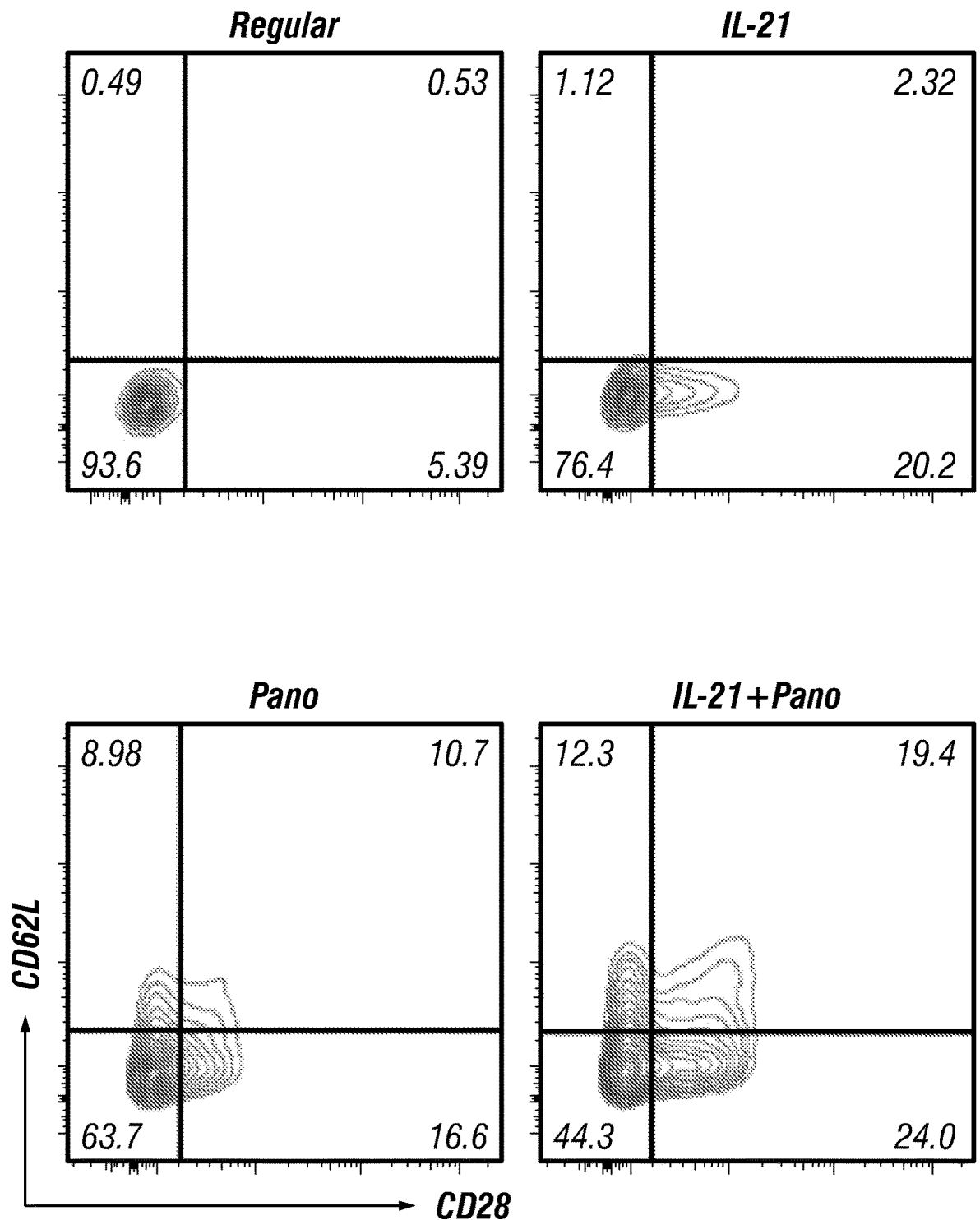
Figure 13B:
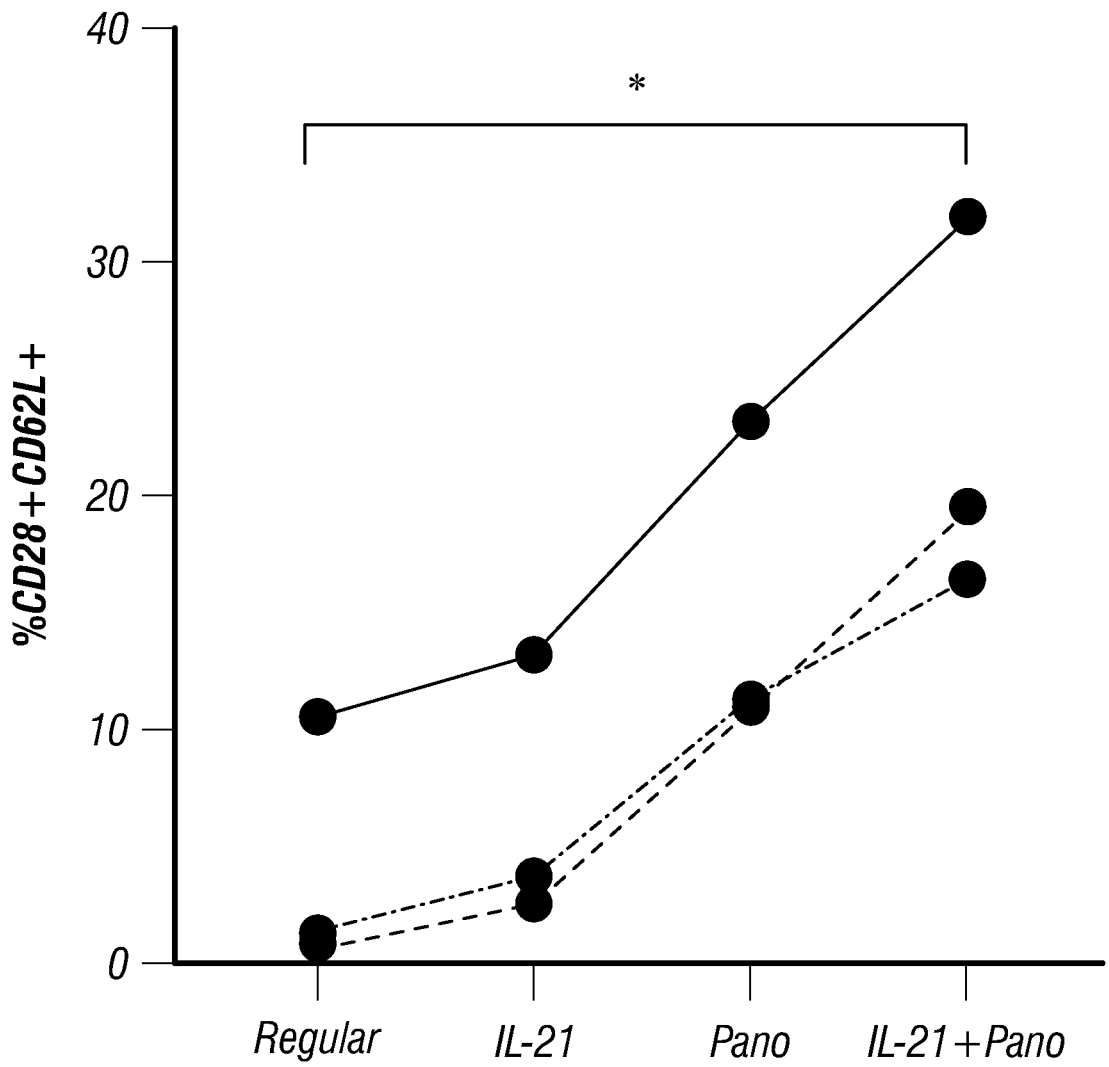

FIGS. 13A-13B: IL-21 and Panobinostat (Pano) cooperate to induce CD28$^+$CD62L$^+$ cells. (A) Representative plots of CD28 and CD62L levels on CTLs expanded with the indicated conditions for 2 weeks. The numbers within the plots annotate the percentage of cells in each quadrant. (B) Percentage of CD28$^+$CD62L$^+$ cells in CTLs expanded with the indicated conditions from independent experiments (n=3; * p<0.05; one-way ANOVA, as compared to CTLs expanded with the regular protocol). The representative results out of three (A) independent experiments are shown.

FIGS. 14A-14D: IL-21/Panobinostat-expanded CTLs display central memory-like characteristics in vitro. (A) Proliferation of expanded CTLs when treated with either IL-2 or IL-15 indicated by CFSE dilution. The numbers indicate the percentage of cells divided 2 times or more in 2 days. (B) Representative histogram of CD132 (γC) levels on CTLs expanded with the indicated conditions. The numbers show the representative MFI of CD132 in each condition. (C) Summary of CD132 MFI on CTLs expanded with the indicated conditions from independent experiments (n=6; mean±SEM; * p<0.05,  p<0.01; one-way ANOVA, as compared to CTLs expanded with the regular protocol). (D) The representative results of mRNA gene expression in CD28$^-$CD62L− and CD28$^+$CD62L$^+$ cells sorted from CTLs expanded with IL-21 and Panobinostat. Gene expression was normalized to housekeeping gene RPL13A expression. (n=2; mean±SD;  p<0.01, ns: not significant; two-tailed t test). The representative results out of two (A), three (D), or six (B) independent experiments are shown.

Figure 15A:
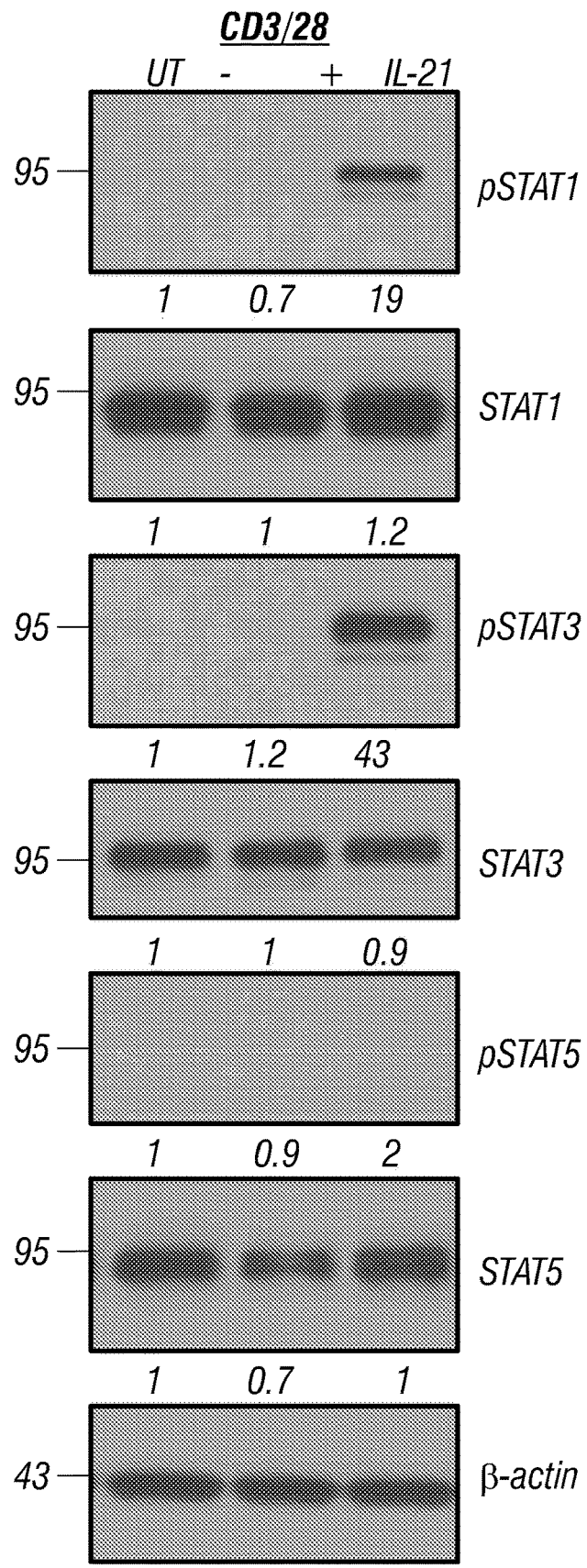
Figure 15B:
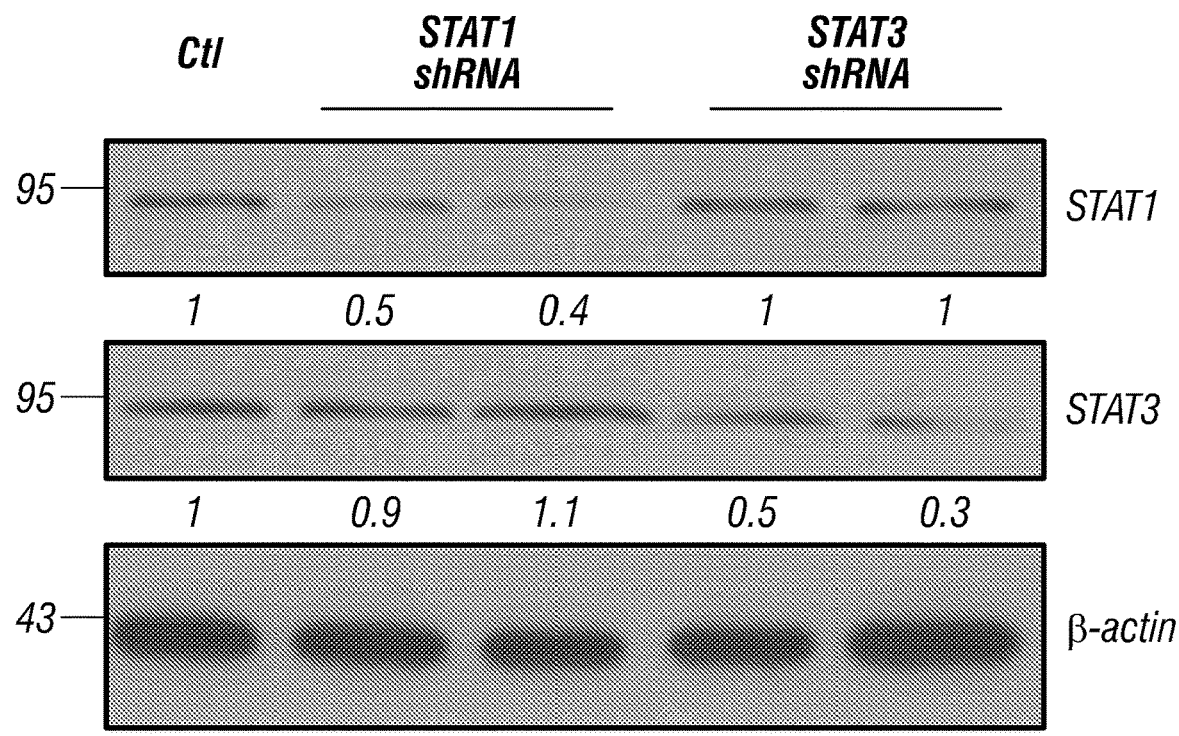

FIGS. 15A-15B: STAT3 is required for IL-21-mediated CD28 upregulation in human naïve CD8$^+$ T cells. (A) Representative western result of pSTAT1, pSTAT3 and pSTAT5 levels at 30 minutes after cell treatment. (B) Western results of total STAT1 and STAT3 level in human CD8$^+$ T cells transfected with negative control, STAT1 or STAT3 shRNAs. β-actin was used as the loading control. The bands were quantified using ImageJ and normalized to the density of actin in the corresponding samples. Molecular weight is indicated in kilodaltons. The representative results out of two (B) or three (A) independent experiments are shown. UT: untreated. Ctl: control.

Figure 16:
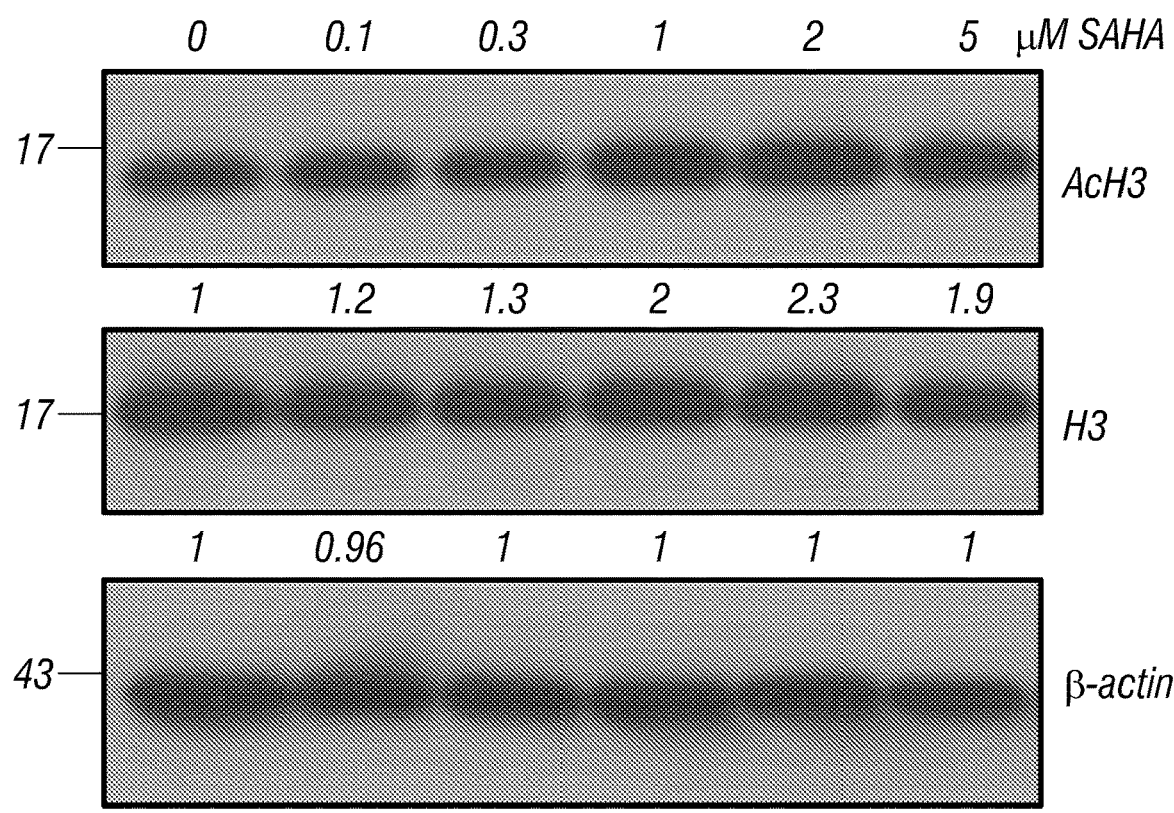

FIG. 16: SAHA increases H3 acetylation in a dose-dependent manner. Western blot results of dose-dependent increase of H3 acetylation (AcH3) level by SAHA. H3 and β-actin were used as loading controls. The bands were quantified using ImageJ and normalized to the density of actin in the corresponding samples. Molecular weight is indicated in kilodaltons. The representative results out of two independent experiments are shown.

Figure 17A:
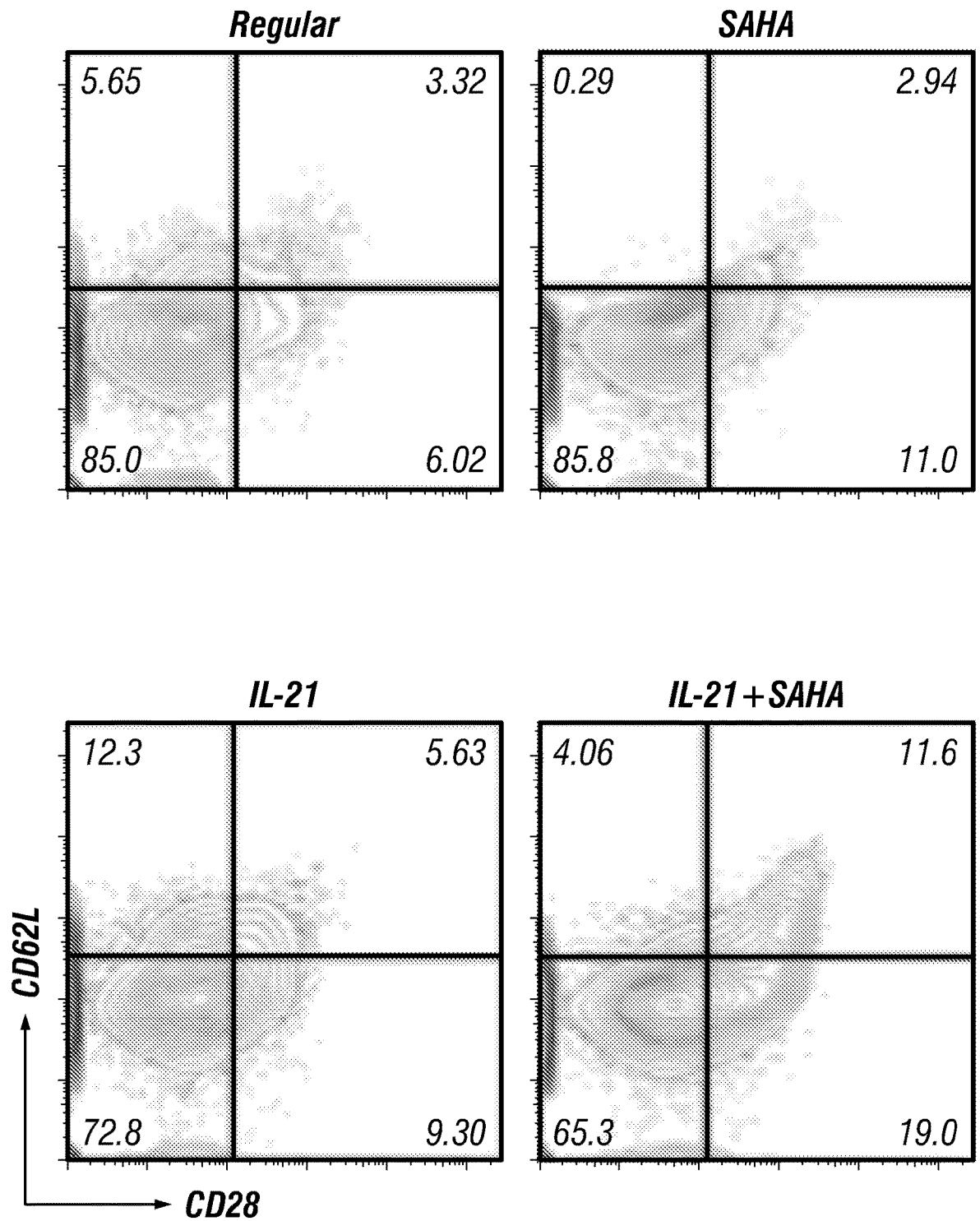
Figure 17A:
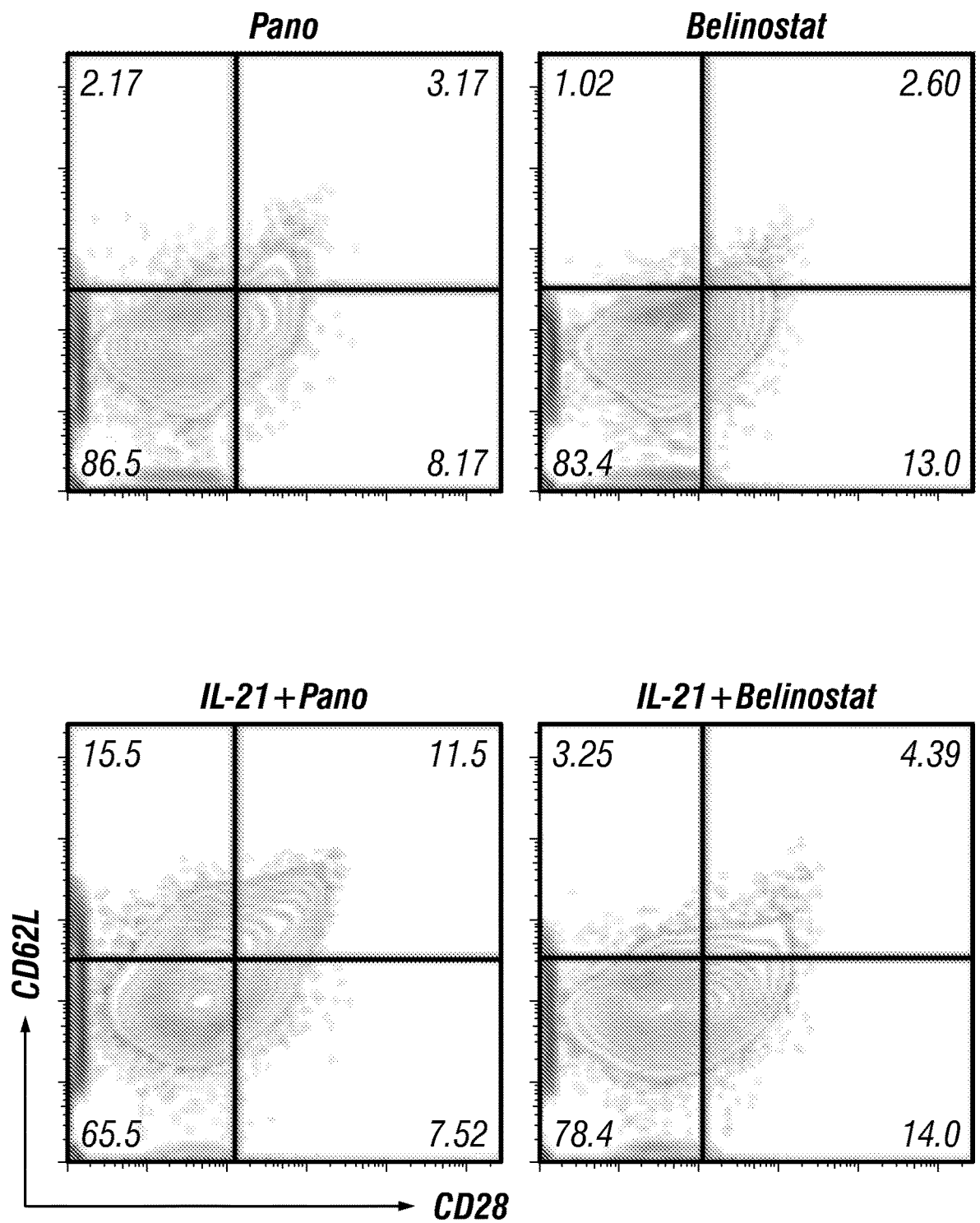
Figure 17B:
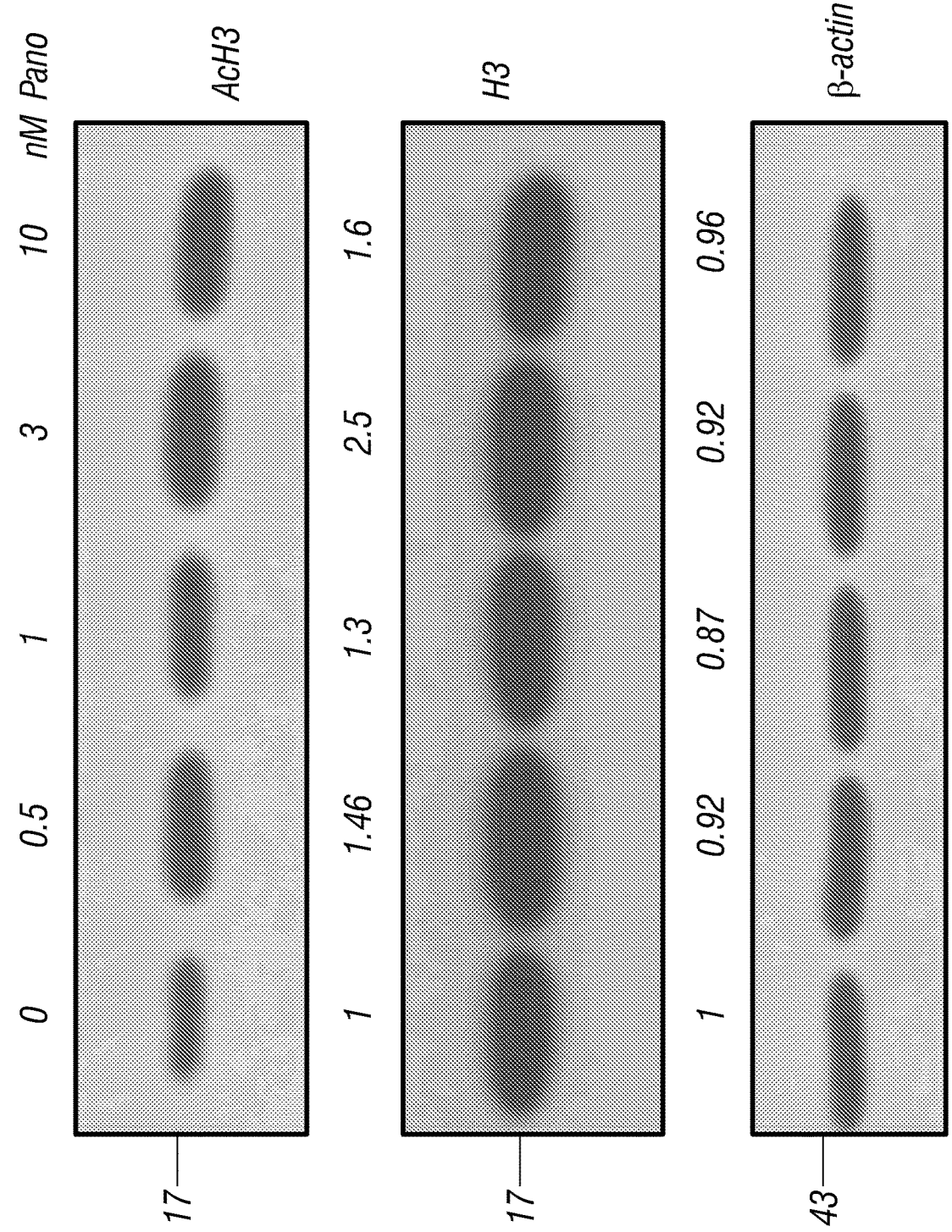

FIGS. 17A-17B: IL-21 and Panobinostat (Pano) synergize to upregulate CD28 and CD62L expression. (A) Representative plots of CD28 and CD62L levels on TILs expanded with the indicated conditions for 2 weeks. The numbers within the plots annotate the percentage of cells in each quadrant. (B) Western results of dose-dependent increase of AcH3 level by Panobinostat. H3 and β-actin were used as loading controls. The bands were quantified using ImageJ and normalized to the density of actin in the corresponding samples. Molecular weight is indicated in kilodaltons. The representative results out of two independent experiments are shown.

Figure 18A:
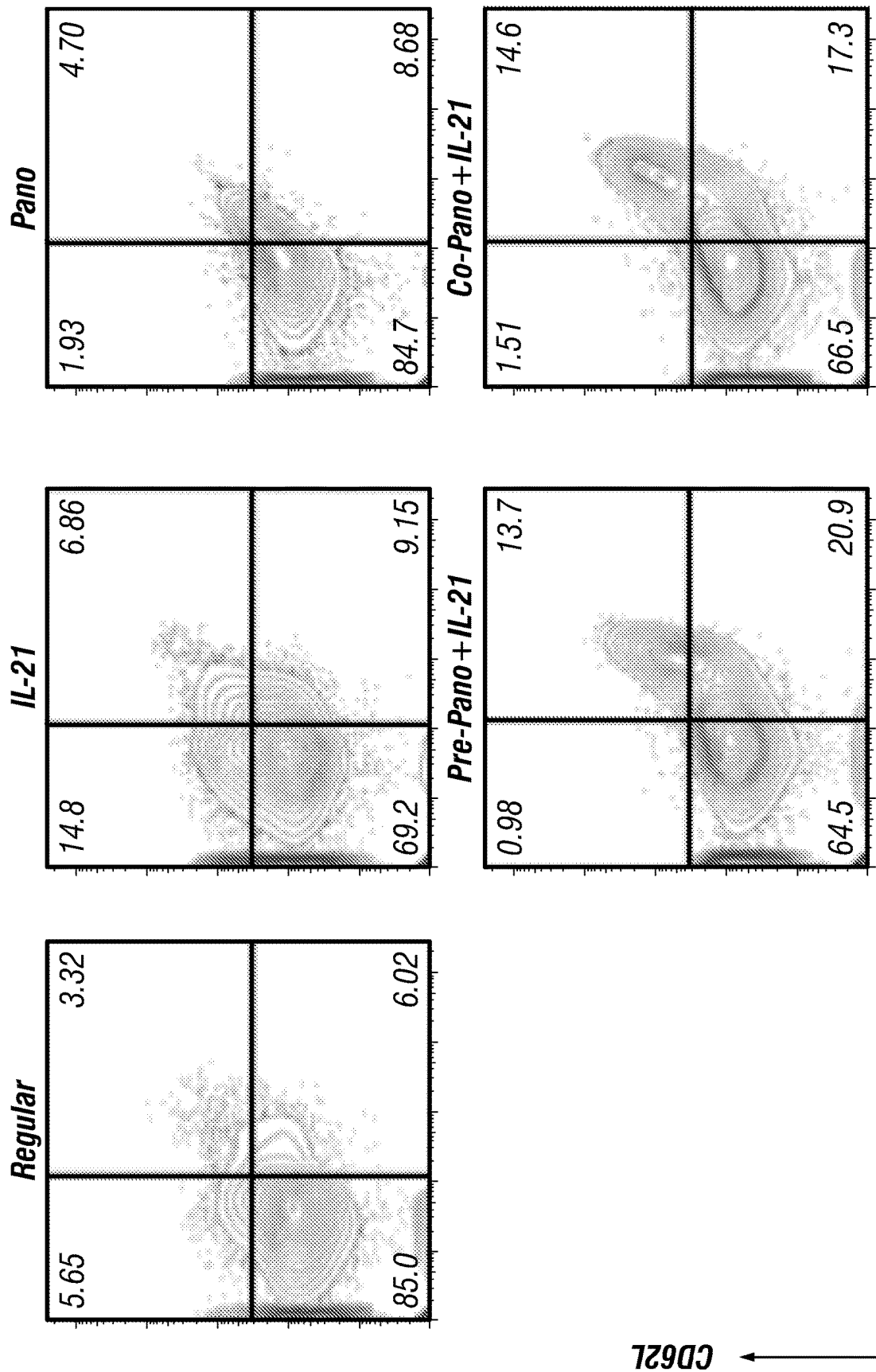
Figure 18B:
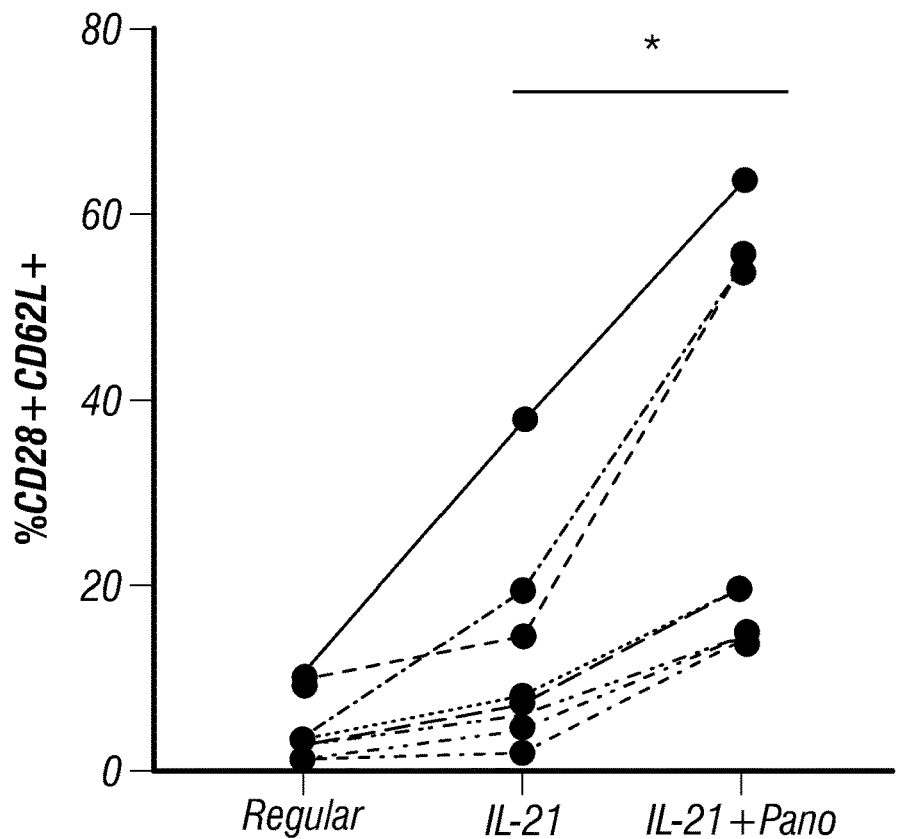
Figure 18C:
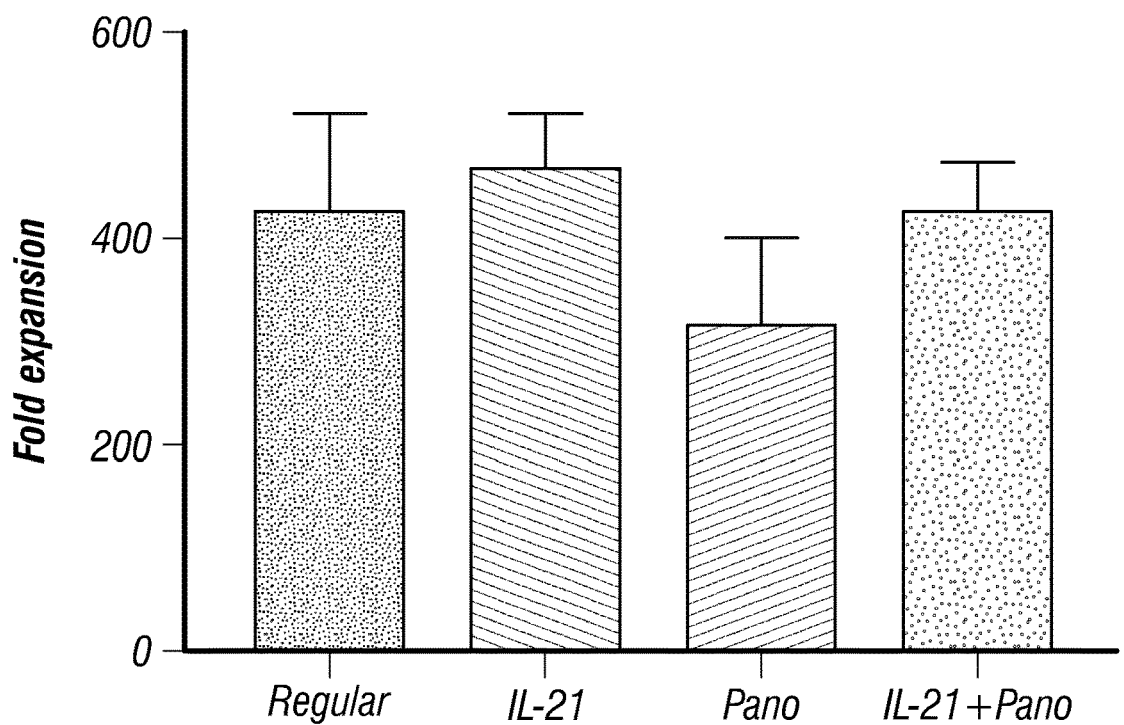

FIGS. 18A-18C: IL-21 and Panobinostat synergize to induce CD28$^+$CD62L$^+$ cells. (A) Representative plots of CD28 and CD62L levels on TILs expanded with the indicated conditions for 2 weeks. The numbers within the plots annotate the percentage of cells in each quadrant. (B) Percentage of CD28+CD62L$^+$ TILs at the end of REP from independent experiments (n=7; * p<0.05; one-way ANOVA). (C) REP expansion fold of CTLs expanded with the indicated conditions for 2 weeks from four independent experiments. Bar graph shows mean±SEM of each condition. The representative results out of two (A) independent experiments are shown.

Figure 19:
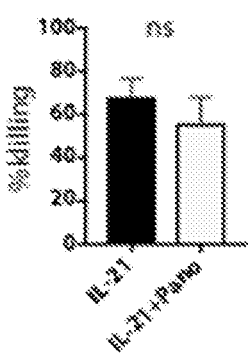

FIG. 19: IL-21/Panobinostat-expanded CTLs exhibit comparable tumor killing capability to CTLs expanded with IL-21. Chromium release assay results demonstrate the percentage of target tumor cell killing by CTLs expanded with the indicated conditions (n=5; mean±SD; ns: not significant; two-tailed t test).

DETAILED DESCRIPTION

I. Definitions

The singular terms "a", "an", and "the" as used herein and in the appended claims include plural referents unless the context clearly dictates otherwise. Thus, for example, reference to "a cell" includes a plurality of such cells and reference to "the peptide" includes reference to one or more peptides and equivalents thereof (e.g., polypeptides) known to those skilled in the art.

The term "or" as used herein and in the appended claims means "and/or" unless explicitly indicated to refer to alternatives only or the alternatives are mutually exclusive.

The term "another" as used herein and in the appended claims may mean at least a second or more.

The term "about" as used herein indicates that a particular value or measurement includes the inherent variation associated with the device used to obtain the measurement, to calculate the value, or the natural variation that exists among the study subjects.

The term "essentially free" as used herein with respect to a component of a solution (e.g., a preparation of one or more proteins, polymers, or small molecules) means that the preparation was not formulated to include that component, or that such component is present only in trace amounts (e.g., as a contaminant). In certain embodiments, a preparation of a molecule of interest is essentially free of a particular component if the preparation comprises less than 0.05% (w/w) of that component. In certain embodiments, a preparation of a molecule of interest is essentially free of a particular component if the preparation comprises less than 0.01% (w/w) of that component. In certain embodiments, a preparation of a molecule of interest is essentially free of a particular component if no amount of the specified component can be detected in the preparation using standard analytical methods (e.g., UV spectrophotometry, mass spectrometry, nuclear magnetic resonance spectroscopy, etc.).

The term "enriched" as used herein with respect to a component of a solution or suspension (e.g., a preparation of one or more cell types, proteins, polymers, or small molecules) means that the preparation was formulated to include that component at a higher than normal concentration, or in greater than normal numbers (e.g., a suspension of lymphocytes may be enriched for effector T lymphocytes).

As used herein, the terms "T cell" or "T lymphocyte" refer to lymphocytes or white blood cells of a type produced by or processed in the thymus gland and actively participating in the adaptive immune response. The term encompasses but is not limited to effector T cells ($T_{EFF}$ cells), CD4$^+$ helper T cells (CD4$^+$ T cells or $T_H$ cells), CD8$^+$ cytotoxic or killer T cells (CD8$^+$ or CTLs), memory T cells, regulatory or suppressor T cells ($T_{REGs}$), natural killer T cells ($T_{NK}$), mucosal associated invariant T cells, and gamma delta or γδ$^+$ T cells ($T_{γδ}$).

Each T cell expresses a T cell receptor (TCR), which recognizes peptide antigens in the context of major histocompatibility complex (MHC) molecules displayed on the surface of antigen-presenting or pathogen-infected cells. The major TCR species comprises an alpha (α) subunit and a beta (β) subunit each encoded by genes that undergo somatic V(D)J recombination to produce a diverse repertoire of antigen-reactive T cells, with up to a possible $10^{14}$ unique TCRαβ heterodimers in each individual. The minor TCR species ($T_{γδ}$) is also produced by somatic V(D)J recombination. Successful recombination of a functional TCR and emergence from the thymus results in a resting, "naïve" T cell capable mainly of migrating through the secondary lymphoid tissues (lymph nodes and spleen) and peripheral circulation, but as yet incapable of producing any kind of response that could protect against infectious challenge.

Producing a T cell capable of mediating immune protection first requires "activation" of the naïve T cell. This involves coordinated interactions between a number of molecules on the T cell and an antigen-presenting cell (APC), a cell that bears an antigenic peptide derived from the infectious agent non-covalently bound to a major histocompatibility complex (MHC) class I or class II molecule. The TCR is composed of two chains (α and β), which recognize the peptide antigen only when it is bound in the context of an appropriate class I or class II MHC molecule. On the T cell, the TCR associates with a complex of membrane proteins collectively known as CD3 (composed of γ-, δ-, ε-, and ζ-subunits), and it is the cytosolic region of this complex that is responsible for propagating an intracellular signal following TCR ligation. Each TCR also associates with either a CD4 or CD8 co-receptor, depending on the type of T cell. These two molecules bind to MHC (class I for CD8 and class II for CD4), further stabilizing the interaction between the T cell and APC.

The category of $T_{EFF}$ comprises various T cell types that actively respond to an immune stimulus (e.g., co-stimulation) including $T_H$, CTL, $T_{REGs}$, and potentially other T cell types. $T_H$ cells assist other lymphocytes in immunologic processes, including the maturation of B cells into plasma cells and memory B cells, and activation of CTLs and macrophages. $T_H$ cells are activated when presented with peptide antigens derived from extracellular proteins bound to MHC class II molecules expressed on the surface of antigen-presenting cells (APCs). There are several subtypes of $T_H$ cells including, but not limited to, $T_H1$, $T_H2$, $T_H3$, $T_H9$, $T_H17$, $T_H22$, and T follicular helper cells (TFH), each secreting one or more different signaling proteins (i.e., cytokines) to up- or down-regulate different aspects of the adaptive immune response. CTLs are capable of killing virus-infected cells and tumor cells, and have been implicated in rejection of transplanted tissue. CTLs are activated when presented with peptides derived from non-self intracellular proteins bound to MHC class I molecules expressed on the surface of target cells. $T_{REGs}$ play a critical role in the maintenance of immunological tolerance by turning off or suppressing T cell-mediated immunity towards the end of an immune reaction and suppressing autoreactive T cells that escaped negative selection in the thymus. There are at least three main classes of $T_{REGs}$: CD4$^+$FoxP3$^+$, CD4$^+$FoxP3$^-$ $T_{REGs}$, and type 1 regulatory T cells (Tri cells), which are CD4$^+$CD49b$^+$LAG-3$^+$CD226$^+$.

CD4$^+$ and CD8$^+$ T cells are most simply classified as naïve or antigen-experienced populations, including memory T cells ($T_{MEM}$) and $T_{EFF}$ cells. Two main subtypes of $T_{MEM}$ cells, $T_{CM}$ cells and $T_{EM}$ cells, are known to differ in their effector functions and ability to home to different anatomical sites. The various types and subtypes of T cells, e.g., naïve T cells, $T_{CM}$ cells, $T_{EM}$ cells, and $T_{EFF}$ cells, can be distinguished by analyzing expression of one or more cell surface proteins characteristic of each type. Standard markers include, for example, CD45, a protein tyrosine phosphatase regulating src-family kinases, is expressed on all hematopoietic cells. Human CD45 can be expressed as one of several isoforms by alternative splicing of three exons comprising part of the extracellular domain. Six isoforms are traditionally identified in humans, comprising variants having either 1, 2, or 3 of the alternatively spliced exons: CD45RA, CD45RO, CD45RB, CD45RAB, CD45RBC, and CD45RABC.

Naïve T cells express CD45RA, L-selectin (CD62L), interleukin receptor 7-alpha subunit (IL7Rα; CD127), and CD28. The category of memory T cells ($T_{MEM}$) comprises various subtypes including, but not limited to, central memory T cells ($T_{CM}$ cells) and effector memory T cells ($T_{EM}$ and $T_{EMRA}$ cells). $T_{CM}$ cells express CD45RO, L-selectin (CD62L), interleukin receptor 7-alpha subunit (IL7Rα; CD127), CD28, and C—C chemokine receptor type 7 (CCR7). $T_{EM}$ cells express CD45RO, lower and somewhat heterogeneous levels of L-selectin (CD62L), interleukin receptor 7-alpha subunit (IL7Rα; CD127), and CD28, but not CCR7. $T_{EMRA}$ cells (terminally differentiated effector memory cells re-expressing CD45RA) express CD45RA, lower and somewhat heterogeneous levels of L-selectin (CD62L), interleukin receptor 7-alpha subunit (IL7Rα; CD127), and CD28, but not CCR7.

As used herein, the terms "tumor infiltrating lymphocytes" or "TILs" refer to a complex mixture of immune cells observed in or isolated from many different types of solid tumor, comprising a mixture of cytotoxic T cells (CTLs) and helper T cells ($T_H$ cells), as well as B cells, macrophages, natural killer cells, and professional antigen presenting cells (APCs) such as, for example, dendritic cells.

As used herein, the term "antigen" refers to a toxin, protein, or other foreign substance that induces a humoral or cellular immune response in a vertebrate, e.g., a human, especially the production of antibodies, the activation of B cells, and/or the activation of T cells. Antigens comprise one or more epitopes.

As used herein, the terms "epitope" or "antigenic determinant" refer to one or more portions of a particular antigen that are recognized by the immune system such as, for example, by antibodies, B cells, or T cells. Thus, an epitope is the specific part of an antigen to which an antibody binds, or the specific peptide bound to a major histocompatibility complex (MHC) molecule to which a T cell receptor binds. Epitopes recognized by antibodies may be linear or conformational. A linear epitope is an epitope that interacts with an antibody through its primary amino acid sequence, e.g., that is formed by a continuous linear sequence of amino acids in the antigen. A conformational epitope is an epitope that interacts with an antibody based on the three-dimensional structure or shape of the antigen (i.e., its tertiary structure), e.g., that is formed by discontinuous or non-linear segments of amino acids in the antigen.

As used herein, the term "neoepitope" refers to a new epitope or an epitope on a new antigen (a "neoantigen"), such as an antigen present in a cancer cell or cancerous tissue as a result of a non-naturally occurring mutation present in the cancer cell or cancerous tissue but not in healthy tissue.

The terms "tumor-associated antigen", "tumor antigen", "tumor-specific antigen", or "cancer cell antigen" are used interchangeably herein to refer to proteins, carbohydrates, or other molecules either uniquely or more abundantly expressed on one or more particular tumor types compared to normal, non-cancerous tissue and capable of stimulating an antigen-specific humoral and/or cellular immune response in a cancer patient.

As used herein, the terms "chimeric antigen receptor", "CAR", "chimeric T cell receptor", "artificial T cell receptor" or "chimeric immunoreceptor" refer to an engineered chimeric receptor construct grafting a desired non-MHC-restricted antigen-binding specificity onto an immune effector cell, e.g., an effector T cell. CARs may comprise, for example, an extracellular antigen-binding domain (e.g., an antibody or an antibody fragment such as, for example, a single-chain variable fragment (scFv) having the desired antigen specificity), a spacer sequence, a transmembrane domain, and one or more intracellular signaling domains. Exemplary intracellular signaling domains may comprise one or more intracellular tyrosine-based activation motifs ("ITAMs"), such as CD3-zeta (CD3ζ), and/or one or more costimulatory signaling domains, such as, for example, CD28, 4-1BB/CD137, ICOS, OX40, or combinations thereof.

As used herein, the terms "antigen presenting cells" or "APCs" refer to a class of immune cells capable of antigen presentation, i.e., capable of presenting an antigenic peptide bound by cell surface major histocompatibility complex molecules to one or more other immune cells, e.g., T cells. Most immune cell types can serve as some type of APC, but professional APCs, e.g., macrophages, B cells, and dendritic cells, present foreign antigens to $T_H$ cells, while other cell types can present intracellular antigens to CTLs. APCs are an essential component of the adaptive immune response, because the functioning of both CTLs and $T_H$ cells depends on APC activity. Antigen presentation allows for the specificity of adaptive immunity and enables adaptive immune responses to both intracellular and extracellular pathogens, and is involved in defense against tumors.

As used herein, the terms "histone deacetylase", "HDAC enzyme", or "HDAC" refer to a class of enzymes (EC 3.5.1.98) that catalyze removal of acetyl groups ($CH_3$—CO—R) from, for example, ε-N-acetyl-lysine amino acids on a histone. See, e.g., Seto and Yoshida, 2014). Histone acetylation and de-acetylation plays an important role in regulating gene expression. The acetylation of histones is thought to neutralize their positive charges and loosen their interaction with negatively-charged DNA. This opens the chromatin structure to facilitate the binding of transcription factors and, subsequently, gene transcription. De-acetylation of histones by HDACs tightens their interaction with DNA, resulting in a closed chromatin structure and the inhibition of gene transcription. Histone lysine acetylation is highly reversible. A lysine residue becomes acetylated by the action of the histone/lysine acetyltransferase enzymes (HATs), and de-acetylated by histone deacetylases (HDACs).

As used herein, the term "HDAC inhibitor" or "HDACi" refers to a broad class of compounds capable of potently and specifically inhibiting the histone deacetylase activity of one or more HDAC enzymes. Classical HDAC is act exclusively on conventional HDACs in Classes I, II, and IV, comprising those HDACs requiring $Zn^{2+}$ as a cofactor for their deacetylase activity. Classical HDACi are typically grouped according to the chemical moiety responsible for binding to the zinc ion, except for cyclic tetrapeptides, which bind to the zinc ion with a thiol group. Exemplary classical HDAC is comprise hydroxamic acids or hydroxamates (e.g., trichostatin A), cyclic tetrapeptides (e.g., trapoxin B) and depsipeptides, benzamides, electrophilic ketones, and aliphatic acids (e.g., phenylbutyrate and valproic acid). Second generation classical HDAC is include the hydroxamic acids vorinostat (suberanilohydroxamic acid or SAHA, marketed as ZOLINZA®), belinostat (PXD101, marketed as BELEODAQ®), panobinostat (marketed as FARYDAQ®), and dacinostat (LAQ824), and the benzamides entinostat (SNDX-275 or MS-275), tacedinaline (C1994), and mocetinostat (MGCD0103).

As used herein, the terms "antibody" or "immunoglobulin" are used interchangeably to refer to any of several high molecular weight glycoproteins typically comprising four separate polypeptides-two heavy chains and two light chains-linked by disulfide bonds. Antibodies are produced normally by specialized lymphocytes called B cells following antigen stimulation. Antibodies are capable of specifically binding particular epitopes on the antigen that stimulated the B cell as part of a humoral immune response. Antibodies are members of the immunoglobulin superfamily, and occur in five different forms referred to as isotypes, each distinguished by the presence of a different heavy chain: IgA, IgD, IgE, IgG, and IgM. Antibodies can be cleaved by protease enzymes to release a series of fragments including, for example, the Fab (fragment, antigen-binding), the Fv (fragment, variable region) comprising complementarity determining regions (CDRs) that determine antigen specificity, and the Fc (fragment, constant region).

Antibodies can be polyclonal or monoclonal. Polyclonal antibodies are a mixture of antibodies secreted by different B cell lineages within the body comprising a collection of antibodies that react against the same antigen, each binding a different epitope. Monoclonal antibodies are antibodies produced by a single clone of cells such as a hybridoma cell line, and comprising antibodies having identical specificity (i.e., each binding the same epitope). The term "antibody"

encompasses all naturally occurring and engineered antibody fragments retaining the desired biological activity, e.g., antigen binding, complement fixation, Fc receptor binding, and the like. Engineered antibodies and antibody fragments include, for example, bispecific antibodies, Fab, F(ab')$_2$, monospecific Fab$_2$, bispecific Fab$_2$, trispecific Fab$_3$, monovalent IgG, scFv, bispecific diabody, trispecific diabody, scFv-Fc, and the like. Depending on the source of the antibody and the desired application (i.e., a mouse monoclonal antibody for use as a human therapeutic) may be further engineered to improve binding affinity or to reduce immunogenicity by a process called 'humanization'.

As used herein, the terms "immunotherapy" or "immune therapy" refer to any approach to prevent or detect or treat cancer that relies on mechanisms involving the immune system such as vaccines, cellular therapies and any vectors or related components involved in the production and use of cellular therapies, oncolytic viruses, antibodies (e.g., naked, drug conjugated, bi-specific, and the like), immunomodulatory agents (e.g., adjuvants, cytokines, growth factors, and the like) and other categories of agents that reduce immunosuppression, enhance trafficking and/or activation of immune cells, or favorably alter the tumor microenvironment, and any laboratory technologies related to the characterization of an immune response against cancer or its effects.

As used herein, the terms "immune checkpoint" or "immune checkpoint protein" refer to any of a plethora of proteins involved in processes or pathways that negatively regulate one or more aspects of the immune response, e.g., the cellular immune response, and play critical roles in the maintenance of self-tolerance, the prevention of autoimmunity, modulating the duration and amplitude of physiological immune responses in peripheral tissues, and the minimization of collateral tissue damage. Immune checkpoint proteins include, for example, programmed cell death pathway 1 (PD-1/CD279) and its ligands (PD-L1/CD274 and PD-L2/CD273), cytotoxic T lymphocyte-associated antigen 4 (CTLA-4/CD152), lymphocyte-activation gene 3 (LAG-3/CD223), B and T lymphocyte attenuator (BTLA), T cell immunoreceptor with Ig and immunoreceptor tyrosine-based inhibitory motif (ITIM) domains (TIGIT), T cell immunoglobulin domain and mucin domain 3 (TIM-3/HAVcr2), killer immunoglobulin-like receptor (KIR/CD158), V-domain immunoglobulin suppressor of T cell activation (VISTA), and the adenosine A2a receptor (A2aR).

As used herein, the term "immune checkpoint inhibitor" refers to a class of therapeutic agents capable of binding immune checkpoint proteins and relieving their negative regulation of the immune response. Exemplary immune checkpoint inhibitors include, for example, ipilimumab (targeting CTLA-4, marketed as Yervoy®), pembrolizumab (targeting PD-1, marketed as Keytruda®), nivolumab (targeting PD-1, marketed as Opdivo®), atezolizumab (targeting PD-L1, marketed as Tecentriq®), avelumab (targeting PD-L1, marketed as Bavencio®), and durvalumab (targeting PD-L1, marketed as Imfinzi®). Immune checkpoint inhibition encompasses both reduction of function and full blockade.

As used herein, the terms "anti-cancer agent", "chemotherapeutic agent" and the like refer to any class of chemicals or compounds that are selectively toxic to cancerous or malignant cells or tissues, i.e., to cells or tissues with high proliferative rates. Chemotherapeutic agents can be used to cure, control, or palliate cancer in a subject. There are many different classes of chemotherapeutics, including alkylating agents, anthracyclines, cytoskeletal disruptors, epothilones, histone deacetylase inhibitors (see above), topoisomerase I inhibitors, topoisomerase II inhibitors, kinase inhibitors, nucleotide analogs and nucleotide precursor analogs, peptide antibiotics, platinum-based compounds, retinoids, *vinca* alkaloids and derivatives, and the like. Alkylating agents include, but are not limited to, cyclophosphamide, mechloroethamine, chlorambucil, melphalan, dacarbazine, nitrosoureas, and temozolomide. Anthracyclines include, but are not limited to, daunorubicin, doxorubicin, epirubicin, idarubicin, mitoxantrone, and valrubicin. Cytoskeletal disruptors (e.g., taxanes) include, but are not limited to, paclitaxel, docetaxel, abraxane (nab-paclitaxel), and taxotere. Inhibitors of topoisomerase I include, but are not limited to, irinotecan and topotecan. Inhibitors of topoisomerase II include, but are not limited to, etoposide, teniposide, and tafluposide. Kinase inhibitors include, but are not limited to, bortezomib, erlotinib, gefitinib, imatinib, venurafenib, and vismodegib. Nucleotide analogs and nucleotide precursor analogs include, but are not limited to, azacitidine, azathioprine, capecitabine, cytarabine, doxifluridine, fluorouracil, gemcitabine, hydroxyurea, mercaptopurine, methotrexate, and thioguanine. Peptide antibiotics include, but are not limited to, bleomycin and actinomycin. Platinum-based agents include, but are not limited to, carboplatin, cisplatin, and oxaliplatin. Retinoids include, but are not limited to, tretinoin, alitretinoin, and bexarotene. *Vinca* alkaloids and derivatives include, but are not limited to, vinblastine, vincristine, vindesine, and vinorelbine.

As used herein, the terms "treat", "treatment", "treating", and the like refer to the process of ameliorating, lessening, or otherwise mitigating the symptoms of a disease or condition in a subject by, for example, administering a therapeutic agent to the subject, or by performing a surgical, clinical, or other medical procedure on the subject.

As used herein, the terms "subject" or "patient" are used interchangeably herein to refer to an individual, e.g., a human or a non-human organism, such as a primate, a mammal, or a vertebrate.

As used herein, the terms "therapeutically effective" or "therapeutically beneficial" and the like refer to a therapeutic agent, or a surgical, clinical, or other medical procedure that ameliorates, mitigates or otherwise relieves one or more symptoms of a disease, disorder, or condition, thereby enhancing the well-being of a subject having a disease, disorder, or condition by, for example, reducing the frequency or severity of the signs or symptoms of a disease, disorder, or condition. Thus, a therapeutically effective or therapeutically beneficial cancer treatment may, for example, reduce the size of a tumor, reduce the growth rate of a tumor, reduce the likelihood of tumor dissemination or metastasis.

As used herein, the terms "pharmaceutically acceptable" or "pharmacologically acceptable" refer to pharmaceutical formulations of therapeutic agents that do not produce an adverse, allergic, or other undesired reaction when administered to a mammalian or vertebrate subject. Such preparations should be formulated in compliance with good manufacturing practice (GMP) standards for sterility, pyrogenicity, purity, and any other relevant standards as required by FDA Office of Biological Standards.

As used herein, the term "pharmaceutically acceptable carrier" refers to any and all chemical compounds or solvents used to formulate a therapeutic agent for delivery to a mammalian or vertebrate subject such as, for example, aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, antioxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, and any combinations thereof, as would be known to one of ordinary skill in the art.

As used herein, the terms "unit dose", "dose", or "dosage" refer to formulations of a therapeutic agent suitable for administration to a mammalian or vertebrate subject containing a predetermined quantity of the agent expected to be therapeutically effective in the subject when administered by an appropriate route and according to a desired treatment regimen. The actual dosage of a particular therapeutic agent to be administered to a subject may be determined empirically by a health care provider in light of a variety of physical and physiological parameters, including, for example, the subject's body weight, age, health, and gender, the type of disease being treated, the extent of disease progression, previous or concurrent therapeutic interventions, the route of administration, and the potency, stability, and toxicity of the particular therapeutic substance.

II. Methods of Reprogramming $T_{EFF}$ Cells

In one aspect, the present disclosure provides methods for reprogramming antigen-specific effector T cells ($T_{EFF}$ cells) into another desired type of T cell such as, for example, central memory T cells ($T_{CM}$ cells). Thus, provided herein are methods for reprogramming antigen-specific effector T cells ($T_{EFF}$ cells) into central memory T cells ($T_{CM}$ cells).

In certain embodiments, the methods comprise the steps of: obtaining a starting population of lymphocytes comprising $T_{EFF}$ cells from a subject; optionally preparing a sample enriched in $T_{EFF}$ cells from the starting population of lymphocytes comprising $T_{EFF}$ cells; and culturing the starting population of lymphocytes comprising $T_{EFF}$ cells or the sample enriched in $T_{EFF}$ cells in the presence of a histone deacetylase inhibitor (HDACi) and interleukin-21 (IL-21), each in an amount sufficient to re-program the $T_{EFF}$ cells into $T_{CM}$ cells, wherein the re-programming produces a population of lymphocytes enriched for $T_{CM}$ cells as compared to the number of $T_{CM}$ cells in the starting population of lymphocytes comprising $T_{EFF}$ cells obtained from a subject.

In certain embodiments, the CD8$^+$ $T_{EFF}$ cells are cultured in the presence of an HDACi prior to adding IL-21. In certain embodiments, the CD8$^+$ $T_{EFF}$ cells are cultured in the presence of an HDACi for 12 to 48 hours prior to adding IL-21. In certain embodiments, the CD8$^+$ $T_{EFF}$ cells are cultured in the presence of an HDACi for 1 to 3 days prior to adding IL-21. In certain embodiments, the CD8$^+$ $T_{EFF}$ cells are cultured in the presence of IL-21 prior to adding an HDACi. In certain embodiments, the CD8$^+$ $T_{EFF}$ cells are cultured in the presence of IL-21 for 12 to 48 hours prior to adding an HDACi. In certain embodiments, the CD8$^+$ $T_{EFF}$ cells are cultured in the presence of IL-21 for 1 to 3 days prior to adding an HDACi.

In certain embodiments, the starting population of lymphocytes comprising $T_{EFF}$ cells is obtained by taking a blood sample from a subject. In certain embodiments, the blood sample is further purified by apheresis. In certain embodiments, the apheresis comprises leukapheresis and produces the starting population of lymphocytes comprising $T_{EFF}$ cells. In certain embodiments, the starting population of lymphocytes comprising $T_{EFF}$ cells is obtained by isolating a sample of tumor infiltrating lymphocytes (TILs) from fresh tumor biopsy tissue taken from a subject. In certain embodiments, the starting population of lymphocytes comprising $T_{EFF}$ cells is obtained by isolating a sample of tumor infiltrating lymphocytes (TILs) from fresh tumor biopsy tissue taken from a subject and expanding the TILs by culturing them in the presence of IL-2. In certain embodiments, the starting population of lymphocytes comprising $T_{EFF}$ cells is obtained by taking a sample of peripheral blood mononuclear cells (PBMCs) from a subject. In certain embodiments, the starting population of lymphocytes comprising $T_{EFF}$ cells is obtained by taking a sample of peripheral blood mononuclear cells (PBMCs) from a subject (e.g., an elderly subject) and expanding the $T_{EFF}$ cells by culturing them in the presence of IL-2. In particular aspects, pretreatment (e.g., activation) of the starting population of lymphocytes is not required. In certain embodiments, the subject is a mammal. In certain embodiments, the mammal is a human, such as an elderly human.

In certain embodiments, the sample of tumor infiltrating lymphocytes (TILs) comprises a cell suspension prepared from fresh tumor biopsy tissue taken from a subject. In certain embodiments, the cell suspension is obtained by mechanical disaggregation of the tumor tissue using, for example, a gentle MACS™ Dissociator (Miltenyi Biotec, Auburn, CA). In certain embodiments, the cell suspension is obtained by enzymatic disaggregation of the tumor tissue using, for example, collagenase.

In certain embodiments, the method further comprises the step of preparing a sample enriched in $T_{EFF}$ cells from the starting population of lymphocytes comprising $T_{EFF}$ cells. In certain embodiments, the step of preparing a sample enriched in $T_{EFF}$ cells from the starting population of lymphocytes comprising $T_{EFF}$ cells comprises isolating desired $T_{EFF}$ cell types and subtypes from the starting population of lymphocytes comprising $T_{EFF}$ cells. In certain embodiments, the desired $T_{EFF}$ cell type or subtype isolated from the starting population of lymphocytes comprising $T_{EFF}$ cells comprises CD8$^+$ $T_{EFF}$ cells. In certain embodiments, the CD8$^+$ $T_{EFF}$ cells also express CD45RO. In certain embodiments, the isolated CD8$^+$ $T_{EFF}$ cells are further purified. In certain embodiments, the further purification comprises a step of depleting the starting population of lymphocytes comprising $T_{EFF}$ cells of myeloid-derived suppressor cells (MDSCs), $T_{REGs}$, NK cells, and macrophages. In certain embodiments, the CD8$^+$ $T_{EFF}$ cells are isolated or further purified using any of various methods of separating immune cell types well-known to artisans of ordinary skill in the art such as, for example, sedimentation, filtration, or density gradient centrifugation taking advantage of differences in the physical properties of different cell types (e.g., size, density); adherence to plastic or other polymer surfaces taking advantage of differences in surface charge and adhesion to separate adherent cells from free-floating cells in suspension; binding of cell surface antigens to one or more specific binding agents (e.g., antibodies, nucleic acid aptamers) to selectively capture different cell types based on specific cell surface phenotypes; captured cells can then be separated from a complex mixture of cells to by flow cytometry, column chromatography, isolation of magnetic beads, or other methods depending on the antibody reagents used.

In certain embodiments, the step of preparing a sample enriched in $T_{EFF}$ cells from the starting population of lymphocytes comprising $T_{EFF}$ cells comprises depleting the starting population of lymphocytes comprising $T_{EFF}$ cells of myeloid-derived suppressor cells (MDSCs), $T_{REGs}$, NK cells, and macrophages. In certain embodiments, the starting population of lymphocytes comprising $T_{EFF}$ cells depleted of MDSCs, $T_{REGs}$, NK cells, and macrophages is further purified. In certain embodiments, the further purification comprises isolating desired $T_{EFF}$ cell types and subtypes from the starting population of lymphocytes comprising $T_{EFF}$ cells depleted of MDSCs, $T_{REGs}$, NK cells, and macrophages. In certain embodiments, the desired $T_{EFF}$ cell type or subtype isolated from the starting population of lymphocytes comprising $T_{EFF}$ cells depleted of MDSCs, $T_{REGs}$, NK cells, and macrophages comprises CD8$^+$ $T_{EFF}$ cells. In certain embodiments, the CD8$^+$ $T_{EFF}$ cells also express CD45RO. In certain embodiments, the CD8$^+$ $T_{EFF}$ cells are isolated or further purified using any of various methods of separating immune cell types well-known to artisans of ordinary skill in the art such as, for example, sedimentation, filtration, or density gradient centrifugation taking advantage of differences in the physical properties of different cell types (e.g., size, density); adherence to plastic or other polymer surfaces taking advantage of differences in surface charge and adhesion to separate adherent cells from free-floating cells in suspension; binding of cell surface antigens to one or more specific binding agents (e.g., antibodies, nucleic acid aptamers) to selectively capture different cell types based on specific cell surface phenotypes; captured cells can then be separated from a complex mixture of cells to by flow cytometry, column chromatography, isolation of magnetic beads, or other methods depending on the antibody reagents used.

In certain embodiments, one or more desired $T_{EFF}$ cell types or subtypes for use in the methods provided herein are identified by and/or isolated from the starting population of lymphocytes comprising $T_{EFF}$ cells based on the presence or absence of one or more cell surface markers. Exemplary cell surface markers useful in such identification and/or isolation include, but are not limited to, for example, CD34, a hematopoietic progenitor stem cell antigen, costimulatory molecules such as, for example, B7-1 (CD80), B7-2 (CD86), CD28, and L-selectin (CD62L). In certain embodiments, populations of $T_{EFF}$ for use in the methods described herein are isolated or characterized based on their expression of CD45RO and/or CD45RA. In certain embodiments, populations of $T_{EFF}$ for use in the methods described herein are isolated or characterized based on their lack of expression of CD28, CD62L, CCR7, and/or CD127. In certain embodiments, the isolation comprises positive selection for expression of a cell surface marker such as, for example, CD8, such that a desired type of $T_{EFF}$ cells, e.g., CD8$^+$ $T_{EFF}$ cells, is retained. In certain embodiments, the isolation comprises negative selection for expression of a cell surface marker such as, for example, Foxp3, such that an undesired type of $T_{EFF}$ cell, e.g., $T_{REGS}$, IS removed.

In certain embodiments, the identification and/or isolation of desired types or subtypes of $T_{EFF}$ based on expression of cell surface markers is accomplished by any of a variety of standard methods known in the art including, but not limited to, for example, fluorescence-activated cell sorting (FACS), column chromatography and other chromatographic methods, panning with magnetic beads, Western blotting, autoradiography, electrophoresis, and various other well-known immunological methods such as, for example, enzyme-linked immunosorbent assays (ELISAs), and the like.

In certain embodiments, the starting population of lymphocytes comprising $T_{EFF}$ cells or the sample enriched in $T_{EFF}$ cells is further cultured or expanded before being cultured in the presence of a histone deacetylase inhibitor (HDACi) and interleukin-21 (IL-21). In certain embodiments, the starting population of lymphocytes comprising $T_{EFF}$ cells or the sample enriched in $T_{EFF}$ cells is further cultured in interleukin-2 (IL-2). In certain embodiments, the IL-2 is administered every three days at a concentration between 50 U/ml and 6000 U/ml. In certain embodiments, the starting population of lymphocytes comprising $T_{EFF}$ cells or the sample enriched in $T_{EFF}$ cells are cultured until confluent, e.g., from about 2 to about 21 days, preferably from about 10 to about 14 days. In certain embodiments, the starting population of lymphocytes comprising $T_{EFF}$ cells or the sample enriched in $T_{EFF}$ cells are cultured until they reach a desired concentration, such as $10^{10}$ or more cells.

In certain embodiments, the cultured starting population of lymphocytes comprising $T_{EFF}$ cells or the sample enriched in $T_{EFF}$ cells are pooled and expanded. In certain embodiments, expansion provides an increase in the number of $T_{EFF}$ cells as compared to the starting population of lymphocytes comprising $T_{EFF}$ cells or the sample enriched in $T_{EFF}$ cells of at least about 50-fold, at least about 60-fold, at least about 70-fold, at least about 80-fold, at least about 90-fold, or at least about 100-fold over a period of about 10 days to about 14 days. In certain embodiments, expansion provides an increase in the number of $T_{EFF}$ cells as compared to the starting population of lymphocytes comprising $T_{EFF}$ cells or the sample enriched in $T_{EFF}$ cells of at least about 200-fold, at least about 300-fold, at least about 400-fold, at least about 500-fold, at least about 600-fold, at least about 700-fold, at least about 800-fold, at least about 900-fold, or at least about 1000-fold over a period of about 10 days to about 14 days.

In certain embodiments, expansion of the cultured starting population of lymphocytes comprising $T_{EFF}$ cells or the sample enriched in $T_{EFF}$ cells is accomplished by any of a variety of standard methods known in the art including, but not limited to, for example, non-specific T-cell receptor stimulation in the presence of feeder lymphocytes and either interleukin-2 (IL-2) or interleukin-15 (IL-15). In certain embodiments, the non-specific T-cell receptor stimulation comprises a dose of 30 ng/ml of OKT3, a mouse monoclonal anti-CD3 antibody (Ortho-McNeil®, Raritan, NJ).

In certain embodiments, the methods provided herein further comprise a step of identifying and/or isolating the reprogrammed $T_{CM}$ cells based on the presence or absence of one or more cell surface markers. Exemplary cell surface markers useful in such identification and/or isolation include, but are not limited to, for example, CD45RO, CD28, CD62L, CCR7, CD127, and CD27. In certain embodiments, populations of $T_{CM}$ produced by the methods described herein are isolated or characterized based on their expression of CD28 and/or CD62L. In certain embodiments, populations of $T_{CM}$ produced by the methods described herein are isolated or characterized based on their lack of expression of CD45RA. In certain embodiments, the isolation comprises positive selection for expression of a cell surface marker such as, for example, CD8, such that a desired type of T cell, e.g., CD8$^+$ $T_{CM}$ cells, is retained. In certain embodiments, the isolation comprises negative selection for expression of a cell surface marker such as, for example, CD45RA, such that an undesired type of T cell, e.g., $T_N$, is removed.

In certain embodiments, the identification and/or isolation of $T_{CM}$ based on expression of cell surface markers is accomplished by any of a variety of standard methods known in the art including, but not limited to, for example, fluorescence-activated cell sorting (FACS), column chromatography and other chromatographic methods, panning with magnetic beads, Western blotting, autoradiography, electrophoresis, and various other well-known immunological methods such as, for example, enzyme-linked immunosorbent assays (ELISAs), and the like.

A. Engineered $T_{EFF}$ Cells

In another aspect, the starting population of lymphocytes comprising $T_{EFF}$ cells for use in the methods for reprogramming antigen-specific $T_{EFF}$ cells into $T_{CM}$ cells provided herein comprise engineered T cells. In certain embodiments, the engineered T cells comprise T cells expressing a chimeric antigen receptor (CAR T cells). In certain embodiments, the engineered T cells comprise T cells expressing a recombinant T cell receptor capable of binding tumor-specific epitopes or neoepitopes.

In some embodiments, the engineered T cells are constructed using any of the many well-established gene transfer methods known to those skilled in the art. In certain embodiments, the engineered cells are constructed using viral vector-based gene transfer methods to introduce nucleic acids encoding a chimeric antigen receptor specific for a desired target tumor antigen or encoding a recombinant TCR specific for a desired tumor-specific epitope or neoepitope. In certain embodiments, the engineered cells are constructed using non-viral vector-based gene transfer methods to introduce nucleic acids encoding a chimeric antigen receptor specific for a desired target tumor antigen or encoding a recombinant TCR specific for a desired tumor-specific epitope or neoepitope. In certain embodiments, the viral vector-based gene transfer method comprises a lentiviral vector. In certain embodiments, the viral vector-based gene transfer method comprises a retroviral vector. In certain embodiments, the viral vector-based gene transfer method comprises an adenoviral or an adeno-associated viral vector. In certain embodiments, the non-viral vector-based gene transfer method comprises a gene-editing method selected from the group consisting of a zinc-finger nuclease (ZFN), a transcription activator-like effector nuclease (TALENs), and a clustered regularly interspaced short palindromic repeats (CRISPR)/CRISPR-associated protein 9 (Cas9) nuclease. In certain embodiments, the non-viral vector-based gene editing method comprises a transfection or transformation method selected from the group consisting of lipofection, nucleofection, biolistics, virosomes, liposomes, polycation or lipid:nucleic acid conjugates, naked DNA, artificial virions, and agent-enhanced uptake of DNA.

In certain embodiments, the CAR T cell expresses a CAR construct comprising an extracellular antigen-binding domain, an optional spacer sequence, a transmembrane domain, one or more intracellular signaling domains, and one or more optional regulatory sequences for activating or inactivating the CAR T cell.

In certain embodiments, the extracellular antigen-binding domain comprises a moiety capable of specifically binding a desired target. In certain embodiments, the moiety capable of specifically binding a desired target comprises a monoclonal antibody or antigen-binding fragment thereof. In certain embodiments, the antigen-binding fragment thereof comprises a single-chain variable fragment (scFv) of a monoclonal antibody capable of specifically binding a desired target. In certain embodiments, the desired target is a tumor-specific antigen. In certain embodiments, the tumor-specific antigen is selected from the group consisting of CD19, CD20, CD22, carcinoembryonic antigen, alphafetoprotein, CA-125, MUC-1, epithelial tumor antigen, melanoma-associated antigen (MAGE) (e.g., MAGE-1, MAGE-11, or MAGE-A), mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, VEGFR2, and human papilloma virus (HPV). In certain embodiments, the desired target is a tumor-specific neoepitope. In certain embodiments, the tumor-specific neoepitope is identified by in silico analysis. In certain embodiments, the tumor-specific neoepitope is identified and purified from a population of autologous TILs derived from a human subject.

In certain embodiments, the transmembrane domain comprises any synthetic or natural amino acid sequence capable of forming a structure able to span a cell membrane. In certain embodiments, the structure able to span a cell membrane comprises an alpha helix. In certain embodiments, the transmembrane region is derived from a naturally occurring transmembrane protein selected from the group consisting of CD3ζ, CD3ε, CD4, CD5, CD8, CD9, CD16, CD22, CD28, CD33, CD37, CD45, CD64, CD80, CD86, CD134, 4-1BB/CD137, CD154, inducible T cell costimulator (ICOS)/CD278, glucocorticoid-induced TNFR-related protein (GITR)/CD357, NKG2D, TCRu and TCRO. In certain embodiments, the transmembrane region derived from a naturally occurring transmembrane protein comprises one or more amino acid substitutions in sequences known to be involved in interactions with other signaling proteins.

In certain embodiments, the one or more intracellular signaling domains comprise one or more intracellular tyrosine-based activation motifs ("ITAMs"). In certain embodiments, the one or more ITAMs are present on a CD3-zeta (CD3ζ) molecule. In certain embodiments, the one or more intracellular signaling domains further comprise a costimulatory signaling domain selected from the group consisting of CD28, 4-1BB/CD137, ICOS, OX40, CD2, CD40L, CD27, Light-R, GITR, or combinations thereof.

B. Recombinant T Cell Receptors (TCRs)

In certain embodiments, the T cells comprise a recombinant T cell receptor capable of binding tumor-specific epitopes or neoepitopes. In certain embodiments, the recombinant T cell receptor comprises a naturally occurring TCR cloned from a T cell isolated from a subject. In certain embodiments, the recombinant TCR comprises a heterodimer comprising a TCR alpha (TCRα) polypeptide and a TCR beta (TCRβ) polypeptide (i.e., a TCRαβ). In certain embodiments, the recombinant TCR comprises a heterodimer comprising a TCR gamma (TCRγ) polypeptide and a TCR delta (TCRδ) polypeptide (i.e., a TCRγδ).

In certain embodiments, the recombinant TCRαp comprises a cloned TCRαp isolated from a subject and specific for a peptide antigen derived from a desired target. In certain embodiments, the subject is a mammal. In certain embodiments, the mammal is a human. In certain embodiments, the desired target is a tumor-specific antigen selected from the group consisting of CD19, CD20, CD22, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, and VEGFR2. In certain embodiments, the recombinant TCRγδ comprises a cloned TCRγδ isolated from a subject and specific for a peptide antigen derived from a desired target. In certain embodiments, the subject is a mammal. In certain embodiments, the mammal is a human. In certain embodiments, the desired target is a tumor-specific antigen selected from the group consisting of CD19, CD20, CD22, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, and VEGFR2.

C. Histone Deacetylase Inhibitors (HDACi)

Provided herein are methods for reprogramming antigen-specific effector T cells ($T_{EFF}$ cells) into central memory T cells ($T_{CM}$ cells) comprising a step of culturing the starting population of lymphocytes comprising $T_{EFF}$ cells or the sample enriched in $T_{EFF}$ cells in the presence of a histone deacetylase inhibitor (HDACi) and interleukin-21 (IL-21), each in an amount sufficient to re-program the $T_{EFF}$ cells into $T_{CM}$ cells, wherein the re-programming produces a population of lymphocytes enriched for $T_{CM}$ cells as compared to the number of $T_{CM}$ cells in the starting population of lymphocytes comprising $T_{EFF}$ cells obtained from a subject. The combined IL-21 and HDACi treatment has a more than additive effect to induce the central memory phenotype from effector T cells and to enhance response to IL-2 and IL-15.

In certain embodiments, the starting population of lymphocytes comprising $T_{EFF}$ cells or the sample enriched in $T_{EFF}$ cells are cultured sequentially with an HDACi and IL-21. In certain embodiments, the starting population of lymphocytes comprising $T_{EFF}$ cells or the sample enriched in $T_{EFF}$ cells is first cultured with an HDACi (e.g., 0.1-5 nM, such as 1-3 nM) and then cultured with IL-21 (e.g., 10-50 ng/mL, such as 20-40 ng/mL, particularly about 30 ng/mL). In certain embodiments, the starting population of lymphocytes comprising $T_{EFF}$ cells or the sample enriched in $T_{EFF}$ cells is first cultured with IL-21 (e.g., 10-50 ng/mL, such as 20-40 ng/mL, particularly about 30 ng/mL) and then cultured with an HDACi (e.g., 0.1-5 nM, such as 1-3 nM). In certain embodiments, the starting population of lymphocytes comprising $T_{EFF}$ cells or the sample enriched in $T_{EFF}$ cells are cultured simultaneously in the presence of an HDACi and IL-21. In certain embodiments, the starting population of lymphocytes comprising $T_{EFF}$ cells or the sample enriched in $T_{EFF}$ cells are cultured simultaneously in the presence of an HDACi and IL-21 for a period of time sufficient to induce a $T_{CM}$ phenotype. In certain embodiments, the starting population of lymphocytes comprising $T_{EFF}$ cells or the sample enriched in $T_{EFF}$ cells are cultured simultaneously in the presence of an HDACi and IL-21 for between 7 and 20 days. In certain embodiments, the starting population of lymphocytes comprising $T_{EFF}$ cells or the sample enriched in $T_{EFF}$ cells are cultured simultaneously in the presence of an HDACi and IL-21 for between 12-16 days. In certain embodiments, the starting population of lymphocytes comprising $T_{EFF}$ cells or the sample enriched in $T_{EFF}$ cells are cultured simultaneously in the presence of an HDACi and IL-21 for 7, 8, 9, 10, 11, 12, 13, 14, 15, 16, 17, 18, 19, or 20 days. In certain embodiments, the starting population of lymphocytes comprising $T_{EFF}$ cells or the sample enriched in $T_{EFF}$ cells are cultured simultaneously in the presence of an HDACi and IL-21 for 13, 14, or 15 days.

In certain embodiments, the starting population of lymphocytes comprising $T_{EFF}$ cells or the sample enriched in $T_{EFF}$ cells are further cultured in the presence of one or more additional cytokines, chemokines, or growth factors. In certain embodiments, the starting population of lymphocytes comprising $T_{EFF}$ cells or the sample enriched in $T_{EFF}$ cells are further cultured in the presence of IL-2. In certain embodiments, the starting population of lymphocytes comprising $T_{EFF}$ cells or the sample enriched in $T_{EFF}$ cells are cultured in the presence of IL-2 prior to being cultured simultaneously in the presence of an HDACi and IL-21.

In certain embodiments, the HDACi comprises a classical HDACi requiring $Zn^{2+}$ as a cofactor for its deacetylase activity. In certain embodiments, the classical HDACi is selected from the group consisting of hydroxamic acids or hydroxamates, cyclic tetrapeptides and depsipeptides, benzamides, electrophilic ketones, and aliphatic acids. In certain embodiments, the HDACi comprises a hydroxamic acid or hydroxamate. In certain embodiments, the hydroxamic acid or hydroxamate is selected from the group consisting of vorinostat (suberanilohydroxamic acid or SAHA, marketed as ZOLINZA®), belinostat (PXD101, marketed as BELEODAQ®), panobinostat (marketed as FARYDAQ®), and dacinostat (LAQ824). In certain embodiments, the HDACi comprises a benzamide. In certain embodiments, the benzamide is selected from the group consisting of entinostat (SNDX-275 or MS-275), tacedinaline (CI994), and mocetinostat (MGCD0103). In certain embodiments, the HDACi comprises a cyclic tetrapeptide or depsipeptides. In certain embodiments, the cyclic tetrapeptide or depsipeptide is trapoxin B. In certain embodiments, the HDACi is an aliphatic acid. In certain embodiments, the aliphatic acid is selected from the group consisting of phenylbutyrate and valproic acid.

D. Interleukin-21 (IL-21)

Human Interleukin 21 (IL-21) is a protein cytokine encoded by the IL-21 gene that has potent regulatory effects on cells of the immune system, including natural killer (NK) cells and cytotoxic T cells that can destroy virally infected or cancerous cells. The 162 amino acid human IL-21 protein (GenBank Accession No. BBA22643; SEQ ID NO:1) is described in U.S. Pat. Nos. 6,307,024, and 6,686,178, both of which are incorporated herein by reference for any purpose. The present methods concern the treatment of Effector T cells with IL-21 in combination with HDACi for the production of Central Memory T cells. In some aspects, the IL-21 is present in the culture media at a concentration of 10 ng/mL to 50 ng/mL, such as 15 ng/mL to 60 mg/mL, such as 20 ng/mL to 40 ng/mL, particularly about 25, 30, or 35 ng/mL.

III. Methods of Use

In another aspect, provided herein are methods for treating cancer or infection in a subject comprising administering to the subject a therapeutically effective amount of the population of lymphocytes enriched for $T_{CM}$ cells produced by any of the methods provided herein. The cells may be adoptively transferred to a subject with a cancer from which TILs may be cultured from or tumor antigen-specific CTLs can be generated from in vitro.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; aeral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

In certain embodiments, the method further comprises a step of performing lymphodepletion prior to administration of the therapeutically effective amount of the population of $T_{CM}$ cells. In certain embodiments, the lymphodepletion comprises non-myeloablative lymphodepleting chemotherapy. In certain embodiments, the non-myeloablative lymphodepleting chemotherapy comprises administration of cyclophosphamide and fludarabine.

In certain embodiments, the method further comprises a step of administering a T-cell growth factor that promotes the growth and activation of autologous T cells to the subject, either concomitantly with the autologous T cells or subsequently to the autologous T cells. In certain embodiments, the T cell growth factor comprises any suitable growth factor that promotes the growth and activation of the autologous T-cells. In certain embodiments, the T cell growth factor is selected from the group consisting of interleukin (IL)-2, IL-7, IL-15, and IL-12, and combinations thereof (e.g., IL-2 and IL-7, IL-2 and IL-15, IL-7 and IL-15, IL-2, IL-7 and IL-15, IL-12 and IL-7, IL-12 and IL-15, or IL-12 and IL-2).

In certain embodiments, the therapeutically effective amount of the population of lymphocytes enriched for $T_{CM}$ cells produced by any of the methods provided herein is administered to the subject intravenously, intratumorally, or intraperitoneally. The appropriate dosage of the T cell therapy may be determined based on the type of cancer to be treated, the severity and course of the disease, the clinical condition of the individual, the individual's clinical history and response to the treatment, and the discretion of the attending physician.

A. Combination Therapies

In certain embodiments, the methods provided herein further comprise a step of administering at least one additional therapeutic agent to the subject. All additional therapeutic agents disclosed herein will be administered to a subject according to good clinical practice for each specific composition or therapy, taking into account any potential toxicity, likely side effects, and any other relevant factors.

In certain embodiments, the additional therapy may be immunotherapy, radiation therapy, surgery (e.g., surgical resection of a tumor), chemotherapy, bone marrow transplantation, or a combination of the foregoing. The additional therapy may be targeted therapy. In certain embodiments, the additional therapy is administered before the primary treatment (i.e., as adjuvant therapy). In certain embodiments, the additional therapy is administered after the primary treatment (i.e., as neoadjuvant therapy.

In certain embodiments, the additional therapy comprises an immunotherapy. In certain embodiments, the immunotherapy comprises an immune checkpoint inhibitor. In certain embodiments, the immune checkpoint inhibitor inhibits an immune checkpoint protein selected from the group consisting of programmed cell death pathway 1 (PD-1/CD279) and its ligands (PD-L1/CD274 and PD-L2/CD273), cytotoxic T lymphocyte-associated antigen 4 (CTLA-4/CD152), lymphocyte-activation gene 3 (LAG-3/CD223), B and T lymphocyte attenuator (BTLA), T cell immunoreceptor with Ig and immunoreceptor tyrosine-based inhibitory motif (ITIM) domains (TIGIT), T cell immunoglobulin domain and mucin domain 3 (TIM-3/HAVcr2), killer immunoglobulin-like receptor (KIR/CD158), V-domain immunoglobulin suppressor of T cell activation (VISTA), and the adenosine A2a receptor (A2aR).

In certain embodiments, the immune checkpoint inhibitor is a PD-1 binding antagonist. In certain embodiments, the PD-1 binding antagonist is an anti-PD-1 antibody. In certain embodiments, the anti-PD-1 antibody is selected from the group consisting of nivolumab, pembrolizumab, and CT-011. In certain embodiments, the PD-1 binding antagonist is an immunoadhesin (e.g., an immunoadhesin comprising an extracellular or PD-1 binding portion of PDL1 or PDL2 fused to an immunoglobulin constant region (e.g., an Fc region of an immunoglobulin sequence).

In certain embodiments, the immune checkpoint inhibitor is a CTLA-4 binding antagonist. In certain embodiments, the CTLA-4 binding antagonist is an anti-CTLA-4 antibody. In certain embodiments, the anti-CTLA-4 antibody is selected from the group consisting of ipilimumab and tremelimumab.

In certain embodiments, the additional therapeutic agent comprises treatment with radiotherapy. In certain embodiments, the radiotherapy is selected from the group consisting of gamma rays (γ-rays), X-rays, microwaves, proton beam irradiation, ultraviolet irradiation, and the directed delivery of radioisotopes to the tumor. In certain embodiments, the radiotherapy comprises treatment with X-rays. In certain embodiments, the X-rays are administered in daily doses of 50 to 200 roentgens over a period of three to four weeks. In certain embodiments, the X-rays are administered in a single dose of 2000 to 6000 roentgens. In certain embodiments, the radiotherapy comprises directed delivery of radioisotopes to the tumor. Dosage ranges for radioisotopes vary widely depending on the half-life of the isotope, the strength and type of radiation emitted, and the degree of uptake by tumor cells, but determination of an appropriate therapeutically effective dose is within the level of ordinary skill in the art.

In certain embodiments, the additional therapeutic agent comprises administration of agents for the treatment of side-effects associated with the primary treatment (e.g., nausea, cachexia, and the like). In certain embodiments, the additional therapy comprises an immunotherapy. In certain embodiments, the additional therapy comprises radiation therapy. In some embodiments, the radiotherapy comprises gamma irradiation. In certain embodiments, the additional therapy comprises surgery. In certain embodiments, the additional therapy comprises a combination of radiation therapy and surgery. In certain embodiments, the additional therapy comprises treatment with a class of chemotherapeutic agent selected from the group consisting of alkylating agents, anthracyclines, cytoskeletal disruptors, epothilones, histone deacetylase inhibitors, topoisomerase I inhibitors, topoisomerase II inhibitors, kinase inhibitors, nucleotide analogs and nucleotide precursor analogs, peptide antibiotics, platinum-based compounds, retinoids, vinca alkaloids and derivatives thereof.

The additional therapies contemplated herein may be administered before, after, or concurrently with administration of the compositions provided herein. In certain embodiments, the additional therapy is administered before the compositions provided herein. In certain embodiments, the additional therapy is administered after the compositions provided herein. In certain embodiments, the additional therapy is administered at one or more intervals before or after administration of the compositions provided herein. Determination of an appropriate interval for administration of an additional therapy such that the subject being treated benefits from the combination therapy is within the level of ordinary skill in the art.

B. Pharmaceutical Compositions

In another aspect, provided herein are pharmaceutical compositions and formulations comprising $T_{CM}$ cells and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of aqueous solutions, such as normal saline (e.g., 0.9%) and human serum albumin (e.g., 10%). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Re-Programming of Effector T Cells to Central Memory T Cells

Figure 1A:
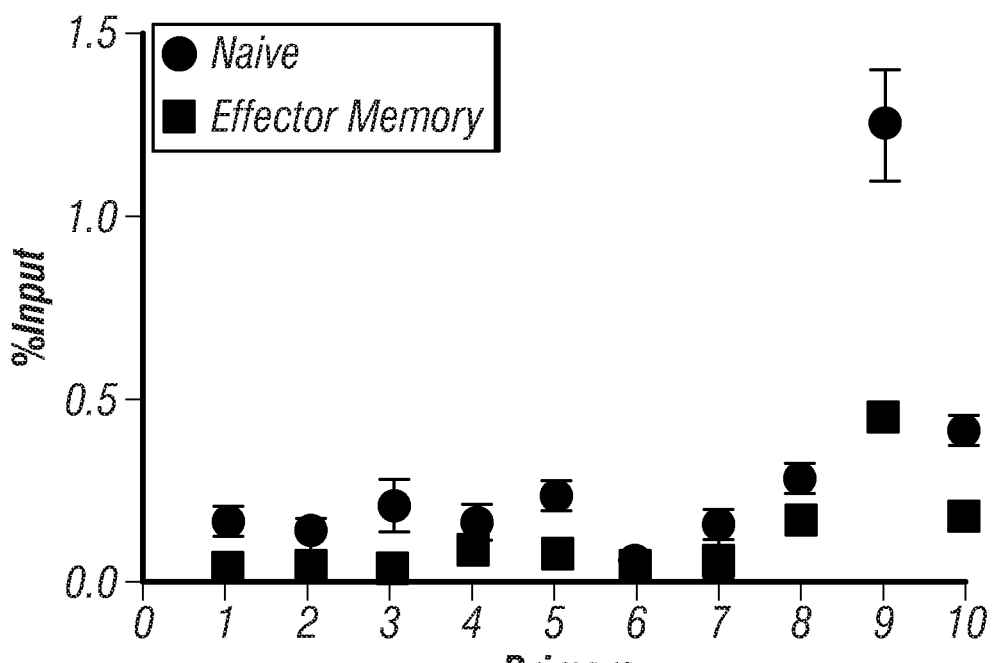
FIGS. 1A-1C: Reduced AcH3 level on CD28 promoter in effector memory ($CD45RA^-CCR7^-$) $CD8^+$ T cells. (A) ChIP results of AcH3 level on CD28 promoter. Primers 8-10 span the genomic DNA region downstream of transcription start site. The results were normalized to percentage of the input amount. Naïve ($CD45RA^+CCR7^+$) $CD8^+$ T cells were used for comparison. (B) Western blot results of dose-dependent increase of AcH3 level by SAHA. H3 and β-actin were used as loading controls. (C) Western blot results of IL-21-induced pSTAT3 in CTLs. STAT3 and β-actin were used as loading controls. The representative results out of two independent experiments are shown.
Figure 1B:
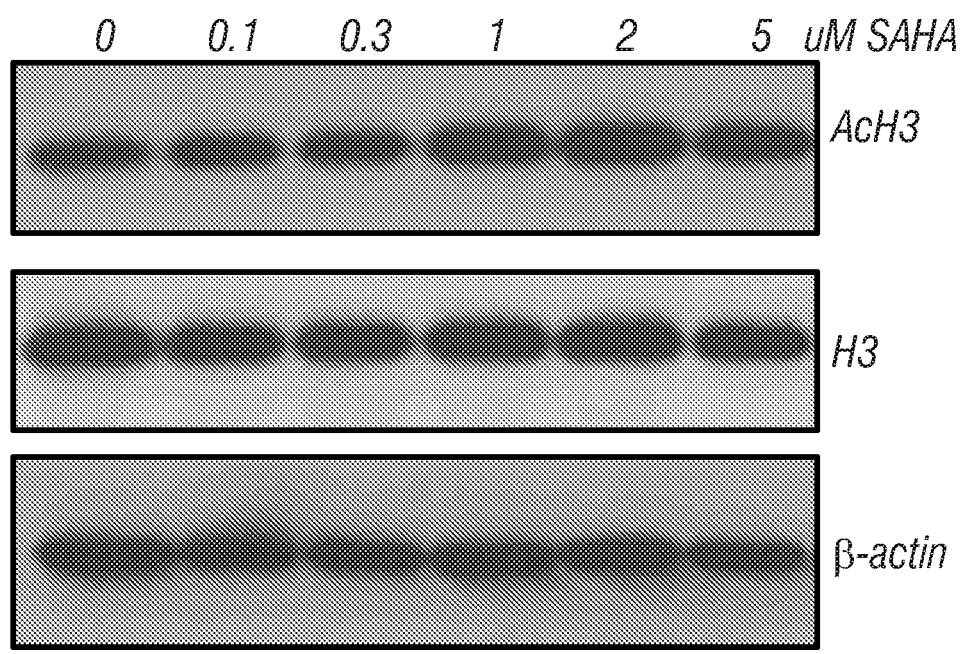
Figure 1C:
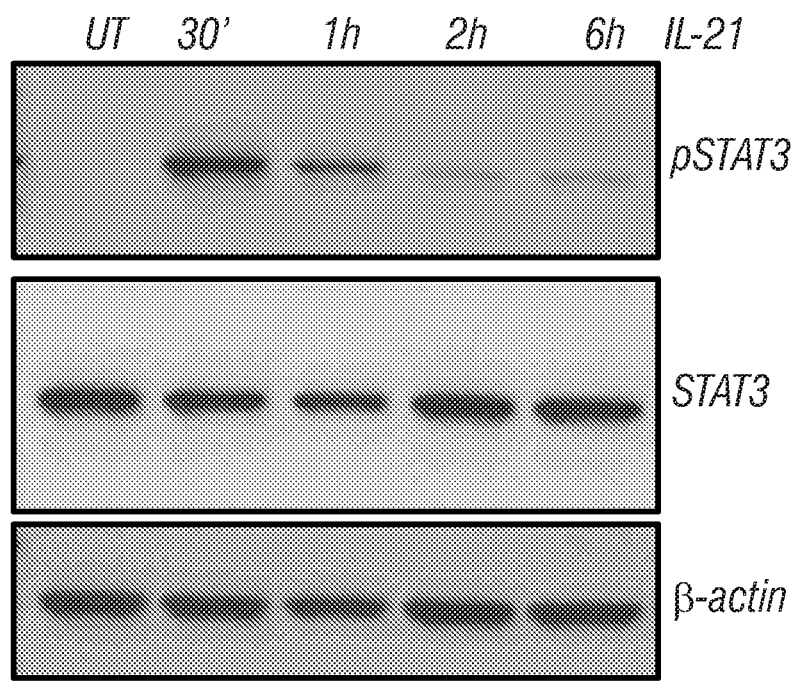

In line with high CD28 expression, naïve CD8+ T cells showed dramatically increased acetylated histone H3 (AcH3) level on the promoter and near the transcription start site of CD28, compared to effector memory CD8+ T cells (FIG. 1A). These results suggested that CD8+ T cell differentiation accompanies loss of histone acetylation and inhibiting histone deacetylation may reverse CD8+ T cell differentiation. FIG. 1B shows that 1 uM or more SAHA augmented AcH3 level in effector CD8+ T cells, and FIG. 1C indicates that IL-21 induced STAT3 phosphorylation in effector CD8+ T cells.

Figure 2A:
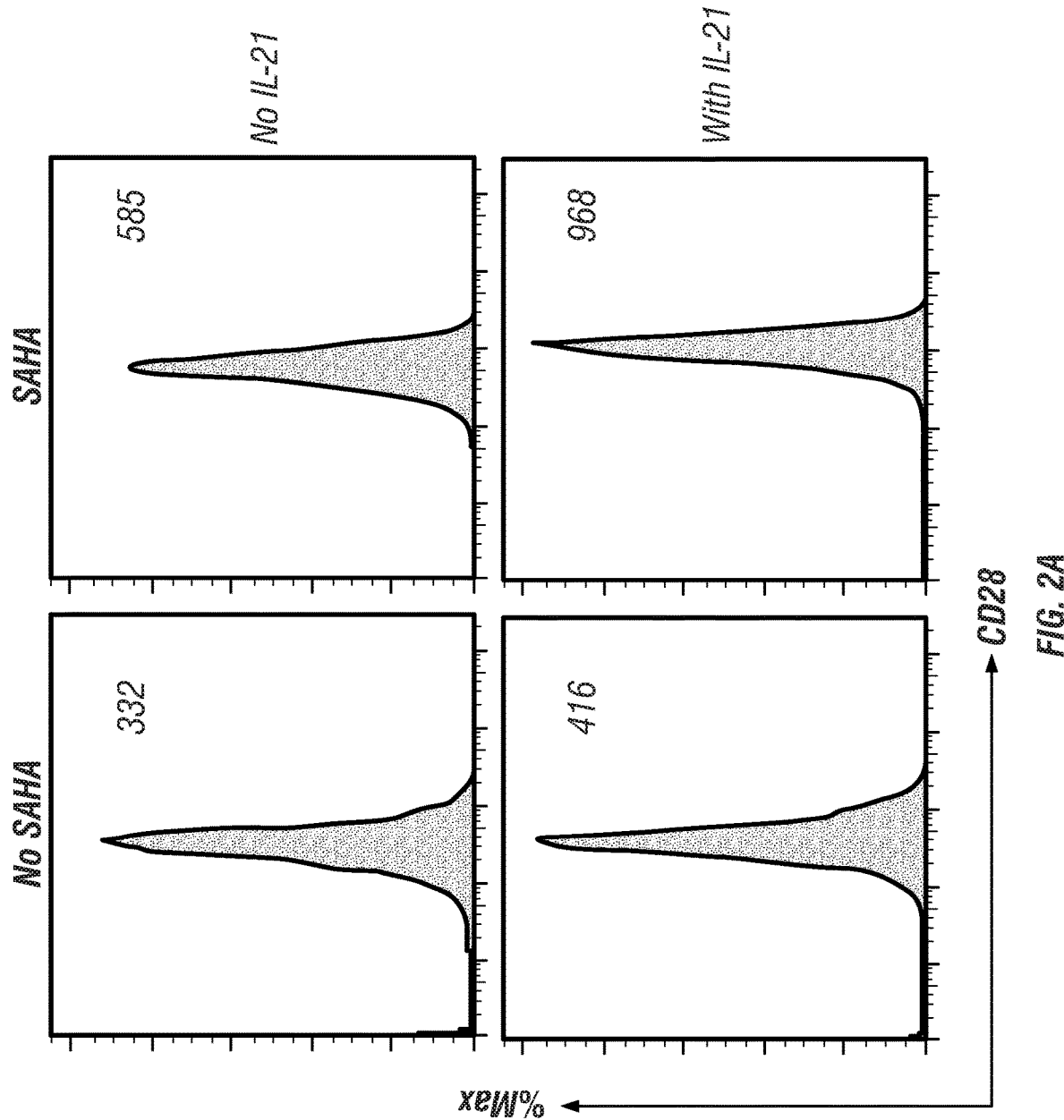
FIGS. 2A-2C: IL-21 and SAHA synergize to upregulate CD28 and CD62L expression. (A) Representative histograms of CD28 level on CTLs treated with the indicated conditions for 4 days. The number inside each panel shows the MFI of CD28 staining. (B) Representative plot of CD28 and CD62L levels on TILs expanded with the indicated conditions for 2 weeks. The numbers within the plots annotate the percentage of cells in each quadrant. (C) ChIP results of enrichment of AcH3 and STAT3 near the STAT binding sites on the CD28 promoter. The results were normalized to percentage of the input amount. IgG was used as a negative control. The representative results out of two independent experiments are shown. MFI: mean fluorescence intensity. AcH3: H3 acetylation.  $p<0.01$, * $p<0.001$.
Figure 8:
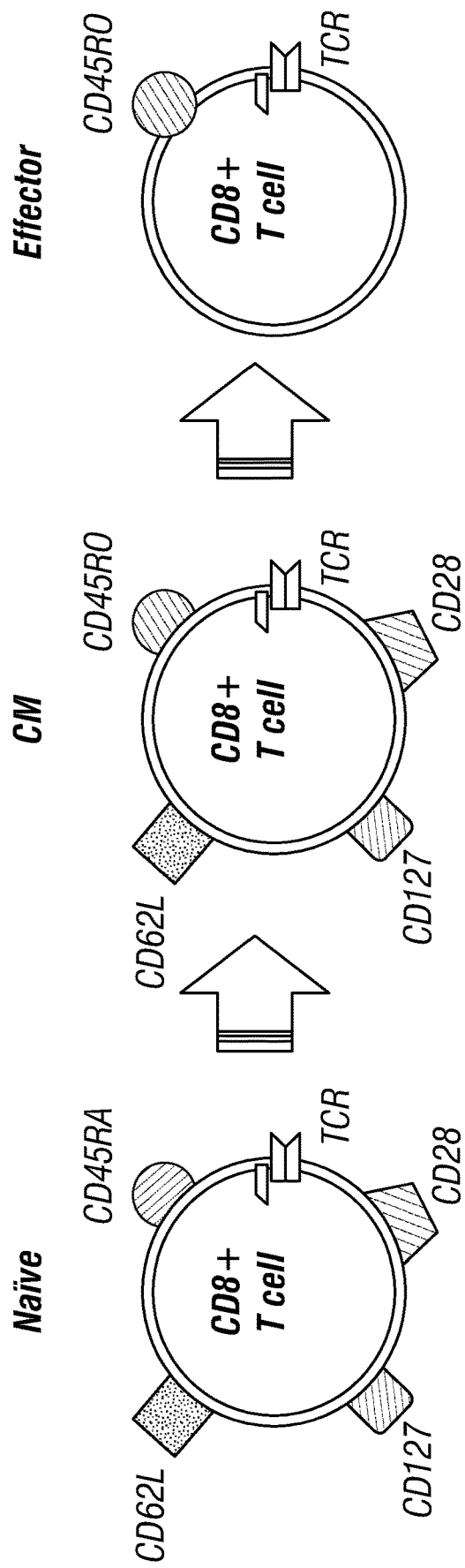
FIG. 8: Schematic depicting markers of Naïve, Central Memory, and Effector T cells. Naïve T cells express CD62L, CD127, CD28, and CD45RA. Central Memory T cells express CD62L, CD45RO, CD127, and CD28. Effector T cells express CD45RO.

The present studies were performed to develop a method to reprogram or de-differentiate effector T cells that express CD45RO to central memory T cells that express CD62L and CD28 (FIG. 8). The effect of IL-21 and histone deacetylase inhibitor (HDACi) treatment on central memory markers CD28 and CD62L was evaluated. MART1 (M27)-specific effector CD8+ T cells were untreated or pretreated with SAHA for 24 hours, followed by activation with M27-pulsed mature dendritic cells in the presence or absence of SAHA/IL-21 for 4 days. Compared to control cells (No SAHA, No IL-21), IL-21 alone slightly increased CD28 expression. While SAHA alone upregulated CD28 expression, interestingly, SAHA and IL-21 together dramatically enhanced CD28 expression, demonstrating the cooperative effect of SAHA and IL-21 on CD28 expression (FIG. 2A).

Figure 2B:
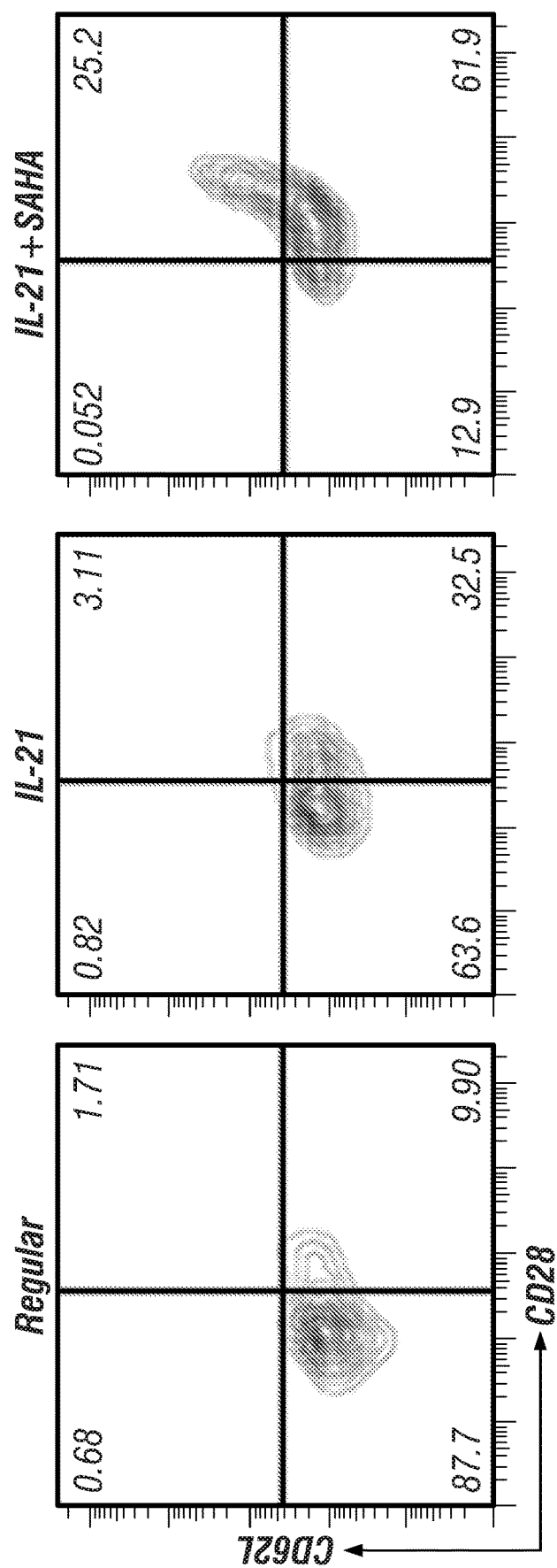

Tumor infiltrating lymphocytes (TILs) were isolated and then expanded with cytokine IL-2. The TILs were treated with IL-21 (30 ng/mL) or a combination of IL-21 and HDACi (SAHA) for 2 weeks. At the end of expansion, TILs were stained with antibodies against CD8, CD28 and CD62L, and analyzed using the CD8+ gate. The results showed that the combination of HDACi and IL-21 treatment resulted in a significant increase in the percentage of central memory T cells (FIG. 2B).

Figure 2C:
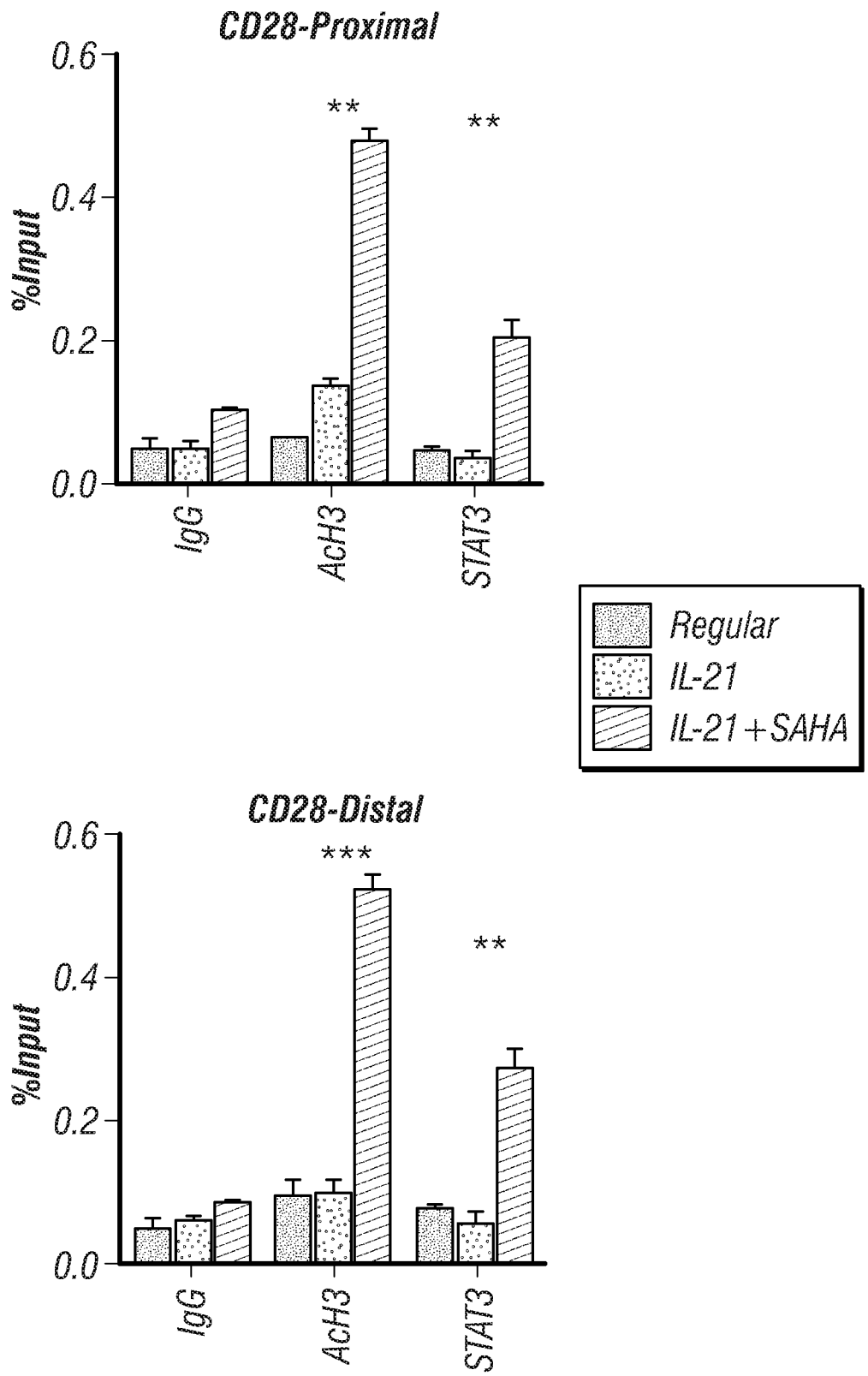

In addition, ChIP results of enrichment of AcH3 and STAT3 near the STAT binding sites on the CD28 promoter showed that HDACi (SAHA) treatment increased the acetylated H3 (AcH3) level on the CD28 promoter, allowing IL-21-induced STAT3 to bind to the same DNA region (FIG. 2C).

Figure 3A:
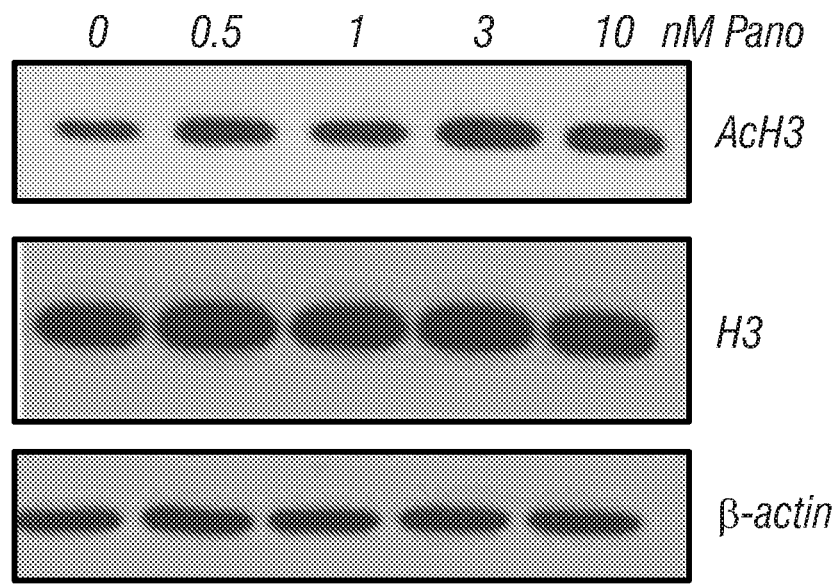
FIGS. 3A-3D: IL-21 and Panobinostat synergize to induce $CD28^+CD62L^+$ CTLs. (A) Western results of dose-dependent increase of AcH3 level by Panobinostat. H3 and β-actin were used as loading controls. (B) Mini-REP expansion fold of CTLs expanded with the indicated conditions for 2 weeks. (C) Percentage of CD28+CD62L+ CTLs at the end of Mini-REP. (D) REP expansion fold of CTLs expanded with the indicated conditions for 2 weeks. Pano: Panobinostat.
Figure 3B:
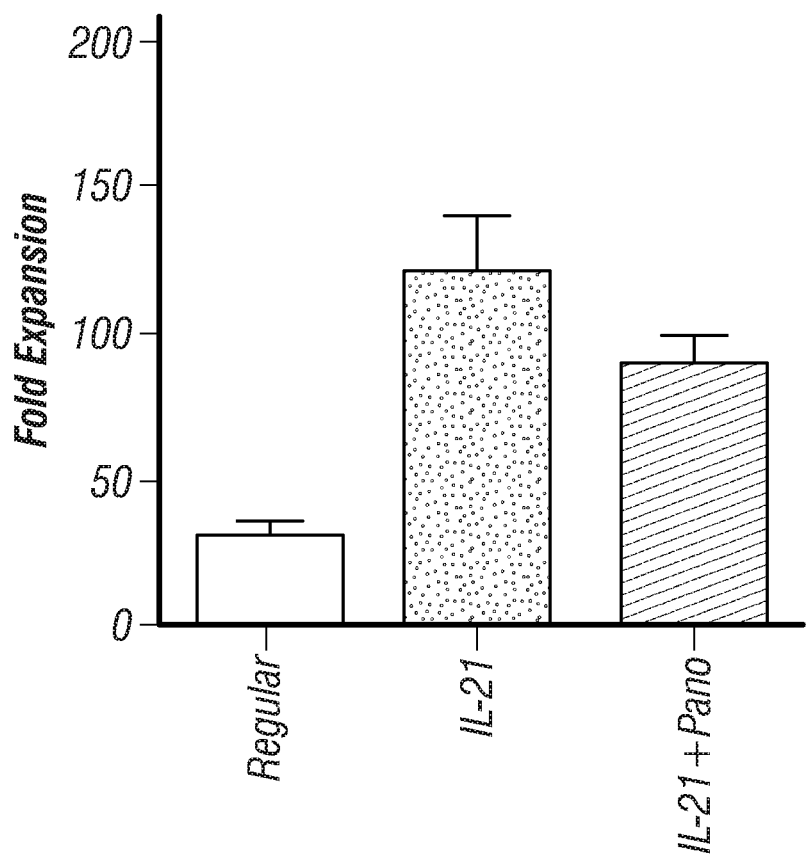
Figure 3C:
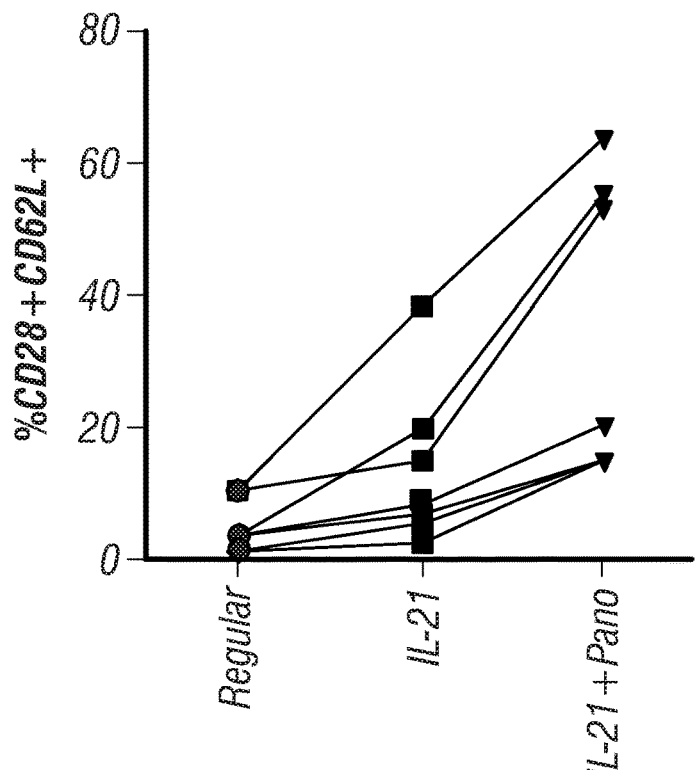
Figure 3D:
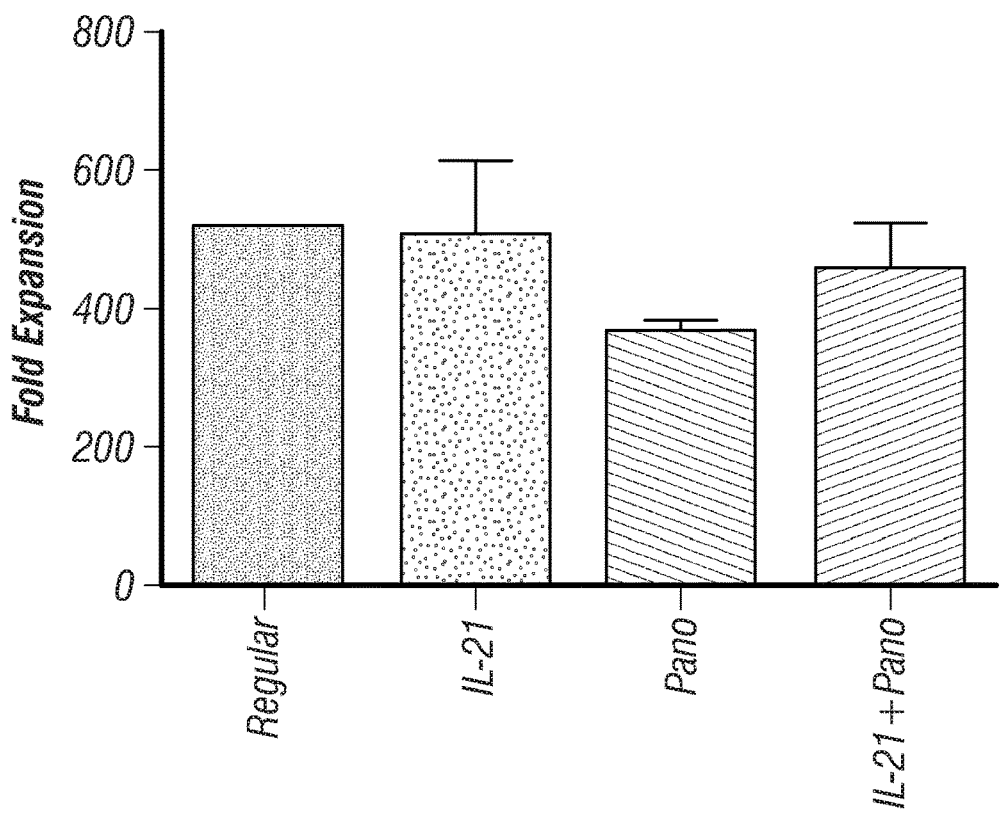

Panobinostat increased AcH3 level at 0.5 nM or higher doses (FIG. 3A). Adding IL-21 with or without Panobinostat to mini-REP dramatically increased the yield of cell expansion (FIG. 3B) and Panobinostat significantly enhanced the induction of CD28+CD62L+ cell population by IL-21 (FIG. 3C). In regular REP, though adding Panobinostat (Pano) alone to REP slightly reduced the expansion yield, expansion fold was similar for the other three conditions (FIG. 3D).

Figure 4A:
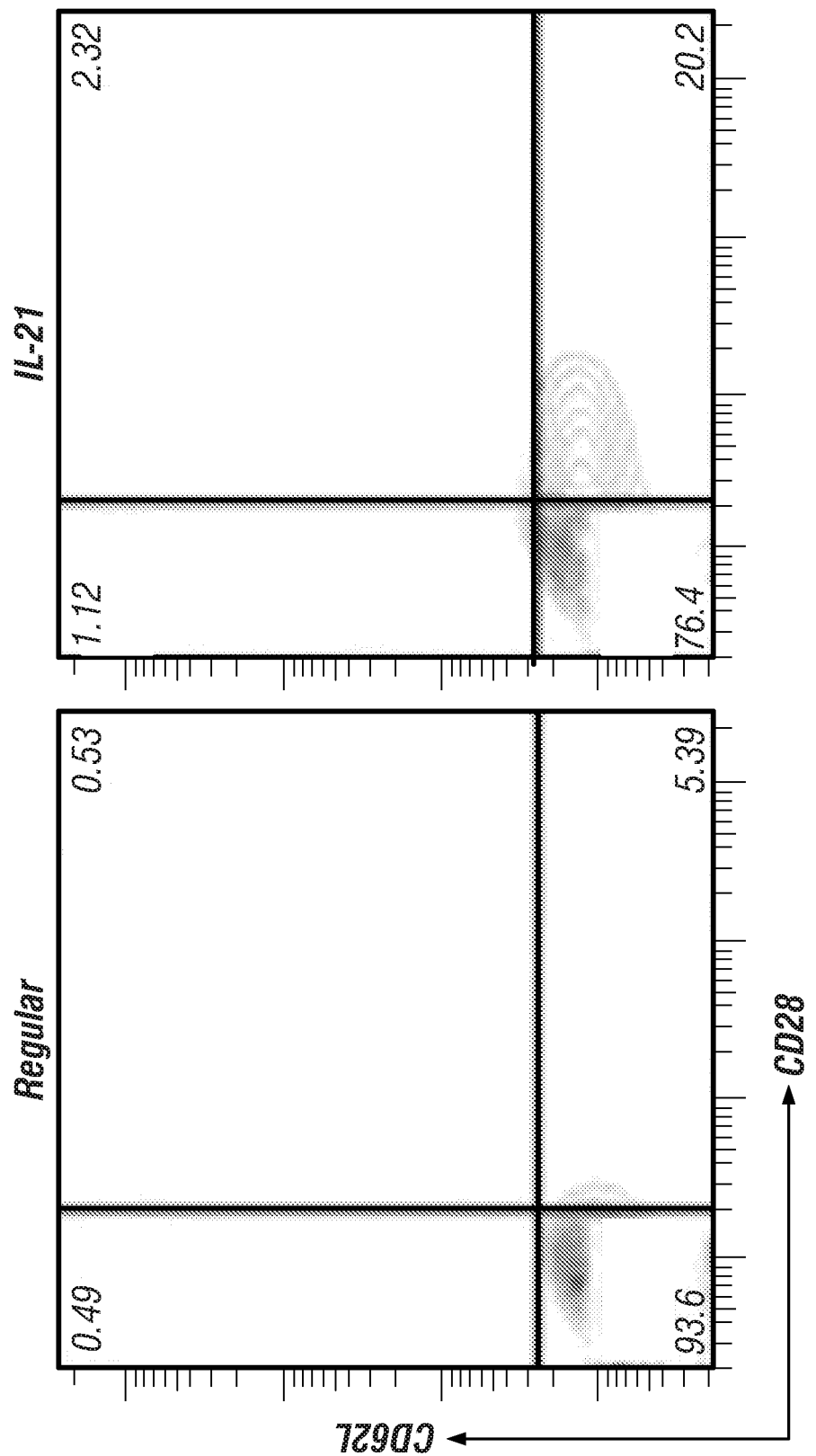
FIGS. 4A-4C: IL-21 and Panobinostat (Pano) cooperate to induce central-memory-like T cells. (A) Representative plot of CD28 and CD62L levels on CTLs expanded with the indicated conditions for 2 weeks. The numbers within the plots annotate the percentage of cells in each quadrant. (B) Proliferation of expanded CTLs when treated with either IL-2 or IL-15 indicated by CFSE dilution. The gates represent the percentage of cells divided 2 times or more in 2 days. (C) Representative histogram of CD132 (gC) levels on CTLs expanded regularly or with IL-21. Summary of CD132 MFI on CTLs expanded with the indicated conditions. The representative results out of three to five independent experiments are shown. Pano: Panobinostat. MFI: mean fluorescence intensity. ** $p<0.01$.
Figure 4A:
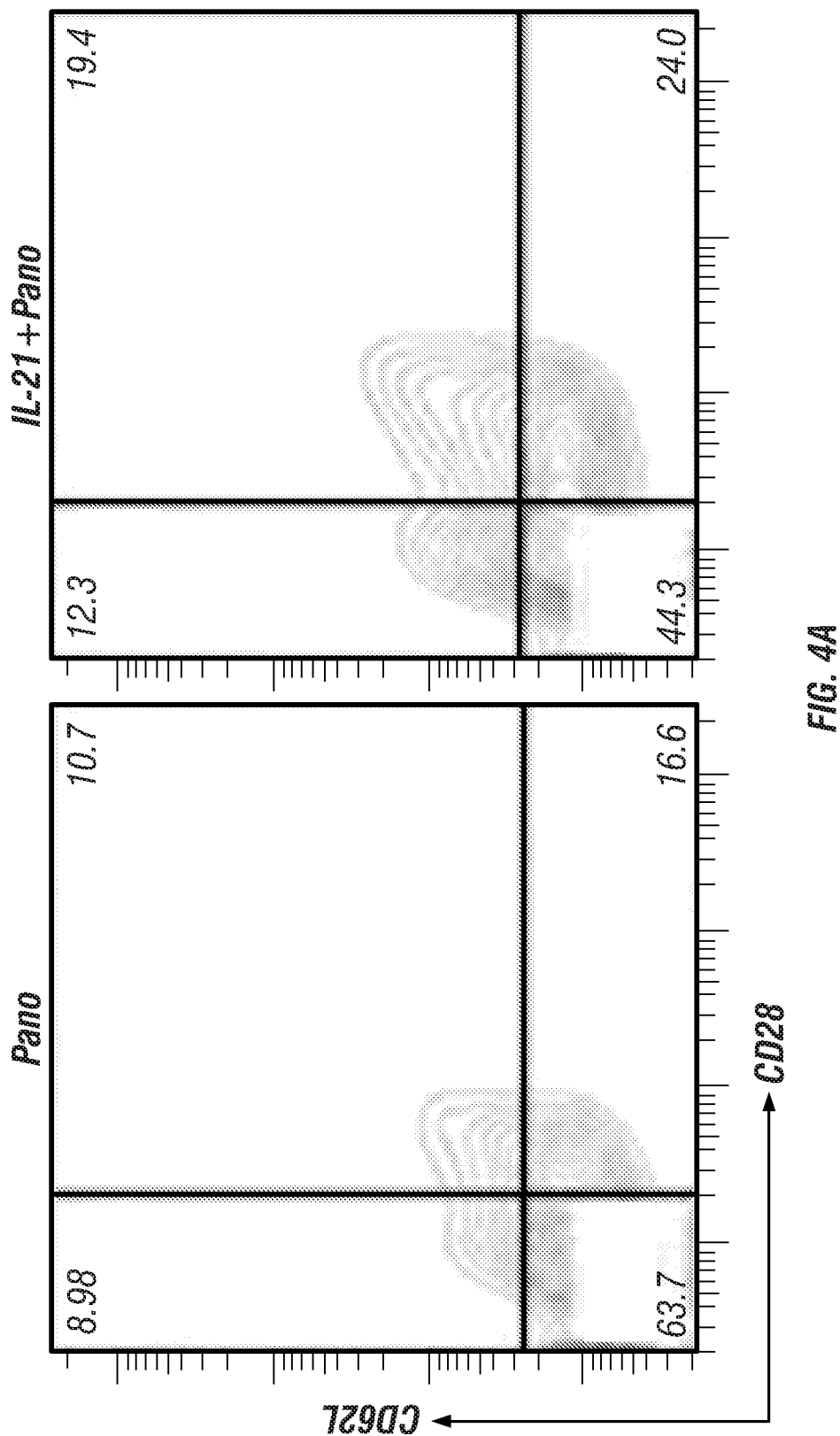

To validate these results, antigen-specific CTL cell lines comprising central memory and effector T cells were expanded and stained with antibodies against CD8, CD28 and CD62L, and analyzed in CD8+ gate. It was found that the combination treatment of IL-21 and the HDACi panobinostat resulted in an increase from about 0.5% Central Memory T cells to over 19% Central Memory T cells (FIG. 4A).

Figure 4B:
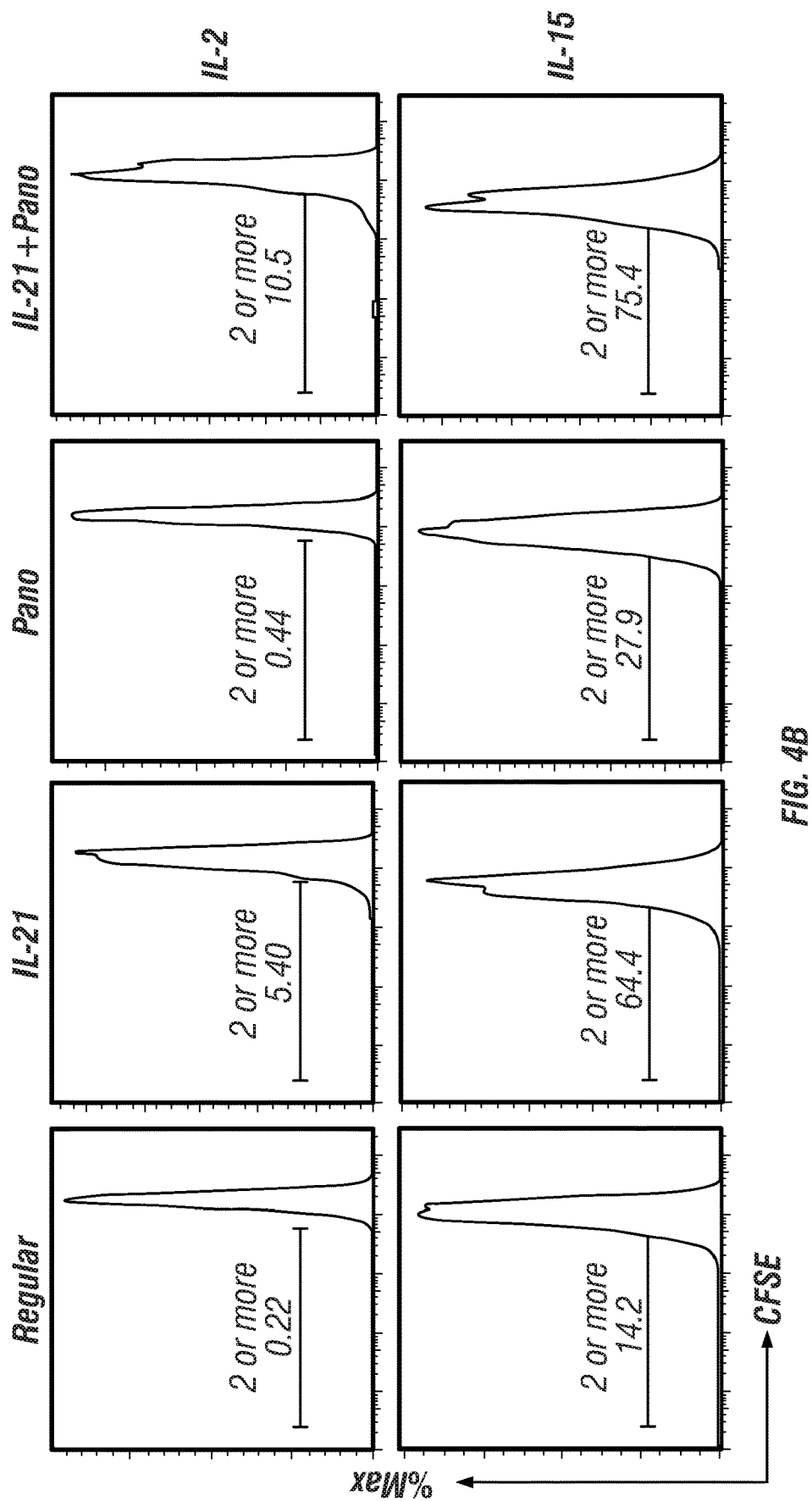
Figure 4C:
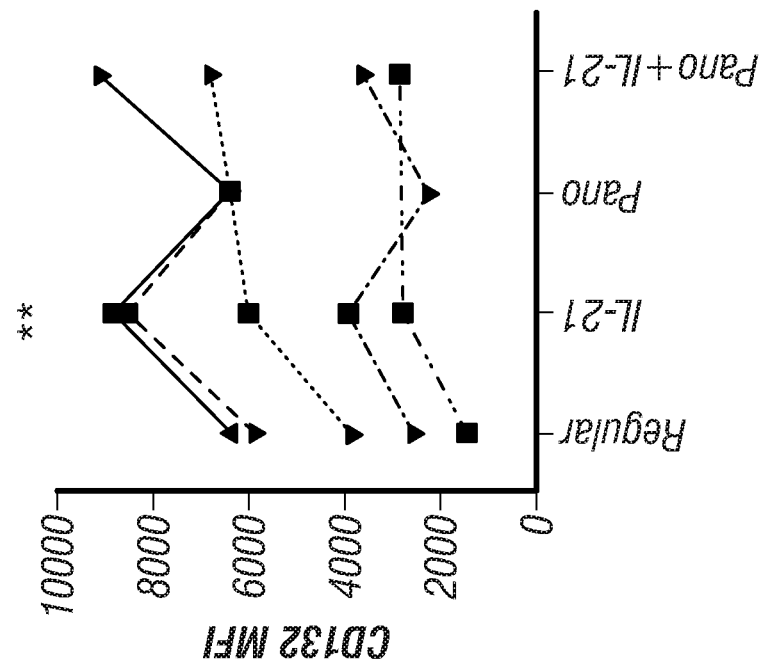
Figure 4C:
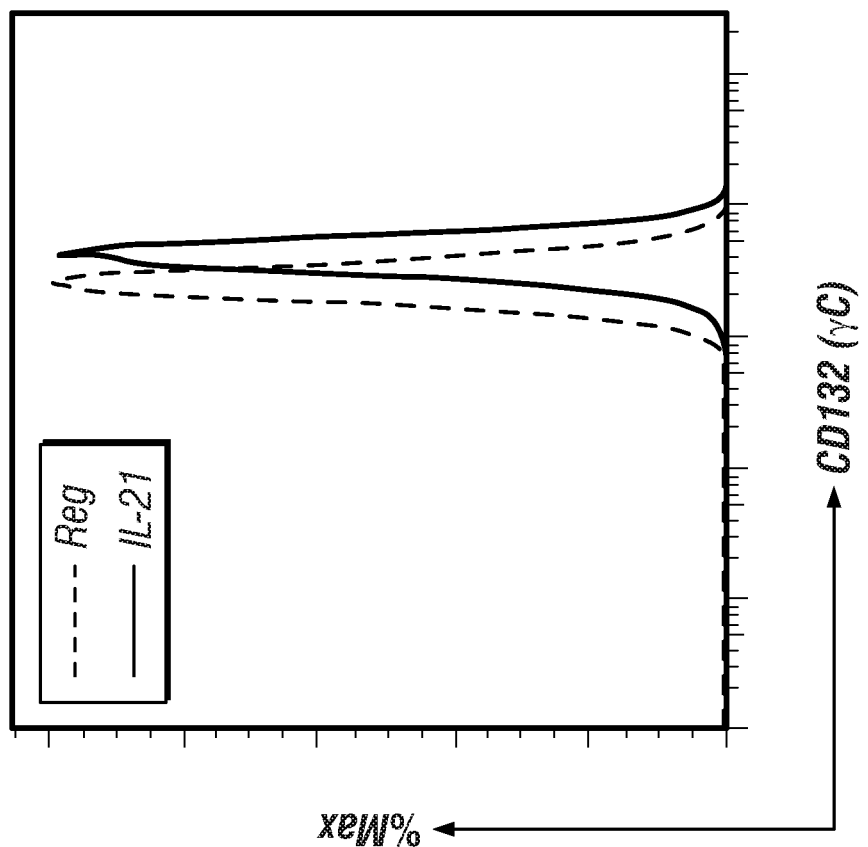

The expanded TILs/CTLs were also stained with antibodies against CD8 and CD132 and analyzed using the CD8+ gate. IL-21 was found to upregulate CD132 (γ chain) expression (FIG. 4C). In addition, the expanded CTLs were labeled with carboxyfluorescein succinimidyl ester (CFSE) and cultured with IL-2 or IL-15 for 2 days to check cell division. The IL-21 and panobinostat-treated cells showed enhanced response to γ-chain cytokines IL-2 and IL-15. (FIG. 4B).

Figure 5A:
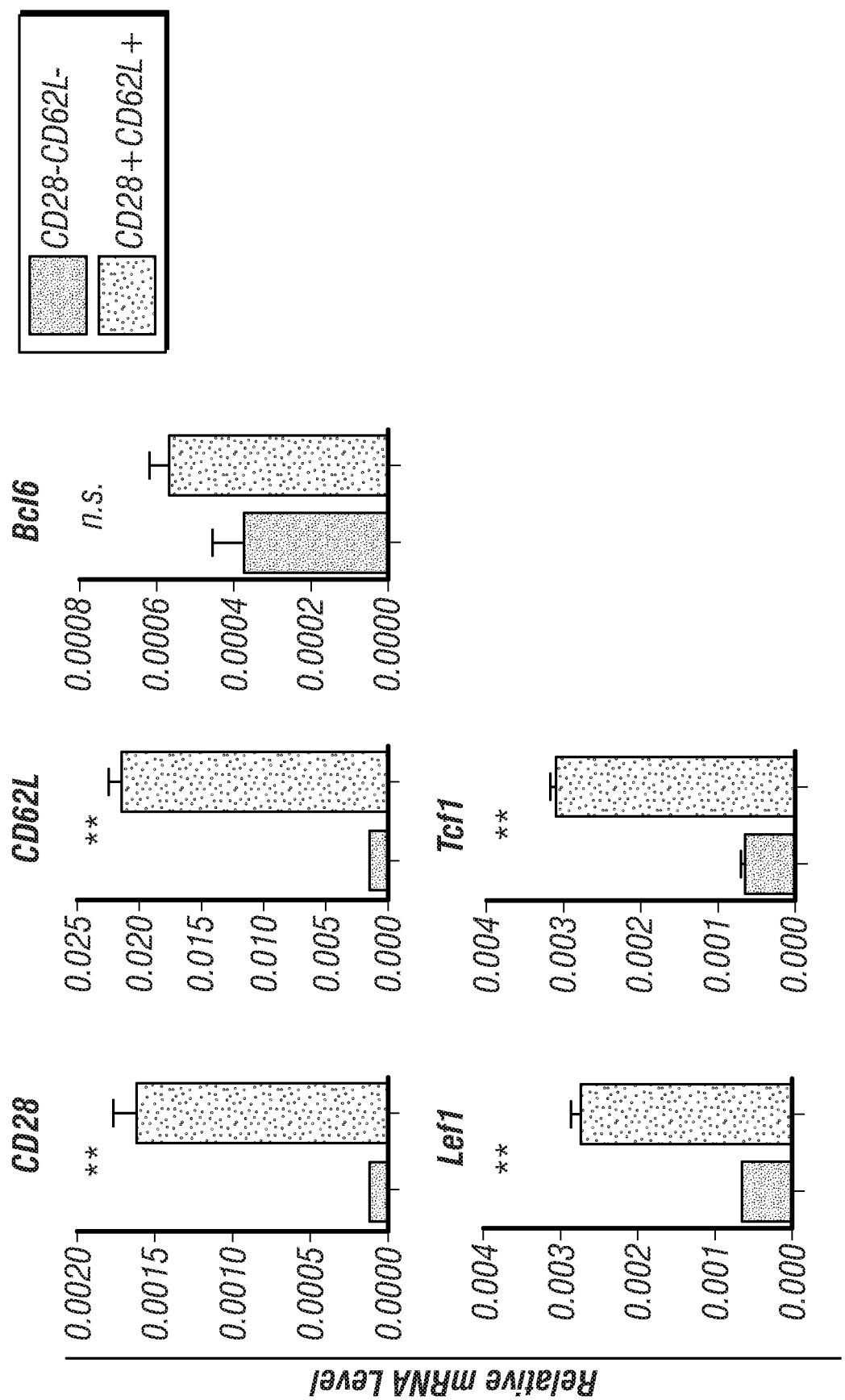
FIGS. 5A-5B: IL-21/Panobinostat-induced $CD28^+$ $CD62L^+$ T cells display enhanced expression of memory-associated genes. (A) CD28-CD62L- and $CD28^+CD62L^+$ CTLs expanded with IL-21 and Panobinostat were sort-purified and mRNA gene expression was normalized to housekeeping gene RPL13A expression. The representative results out of two independent experiments are shown. ** $p<0.01$. n.s.: not significant. (B) Clinical Grex REP expansion fold of TILs.
Figure 5A:
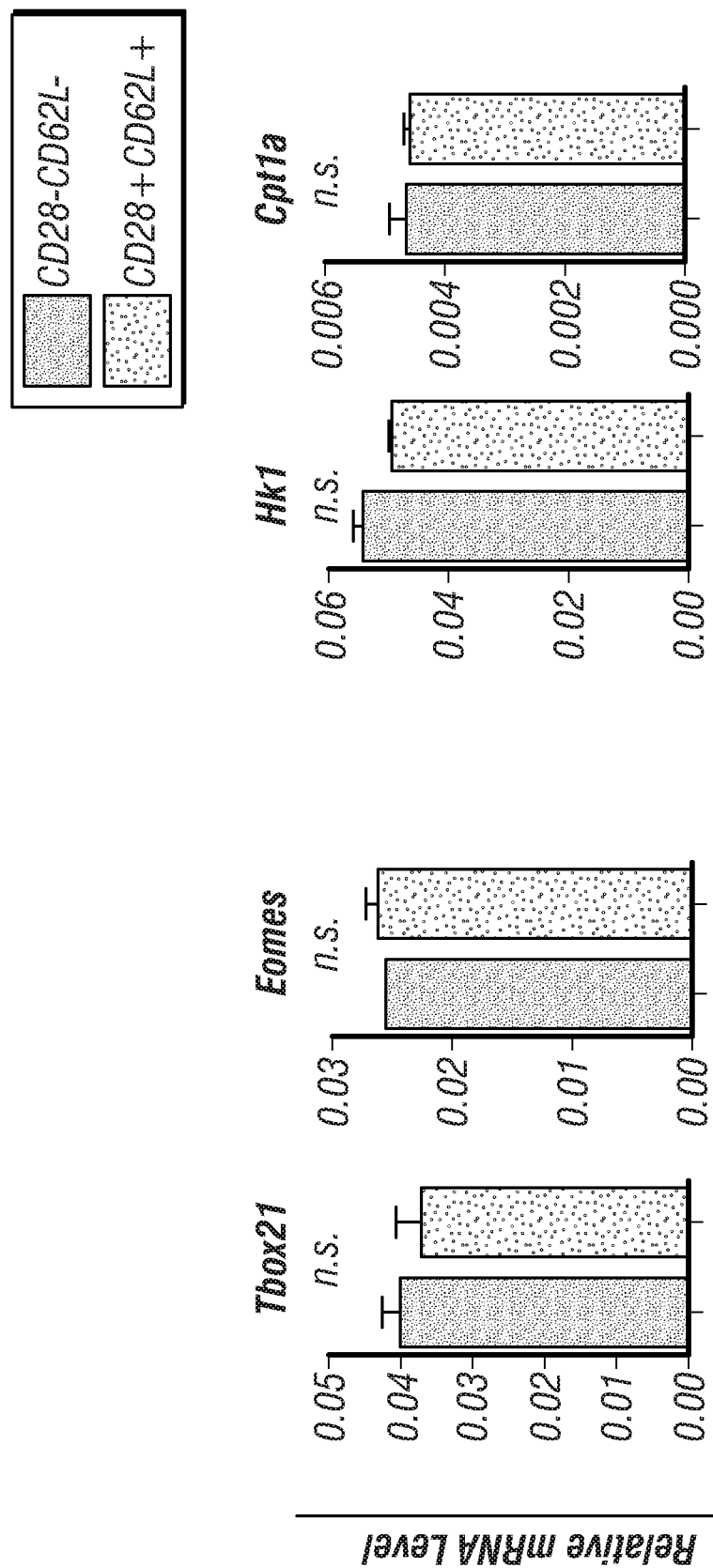

FIG. 5A shows that IL-21 and panobinostat-induced CD28+CD62L+ cells highly expressed CD28, CD62L, Lef1 and Tcf1, which suggested that these cells were less differentiated than CD28−CD62L− cells.

Figure 5B:
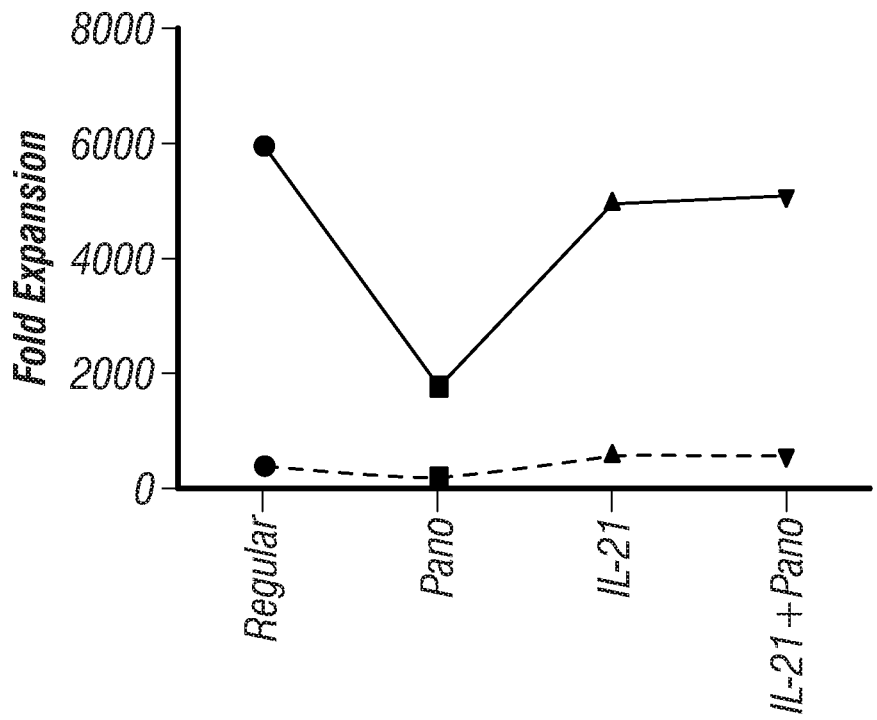

The effect of IL-21 and Panobinostat in the clinical-relevant TIL expansion was assessed. Though including Panobinostat alone in the expansion reduced the product yield in one TIL line, the expansion fold was similar for regular expansion and with IL-21/Panobinostat in the expansion (FIG. 5B).

Figure 6A:
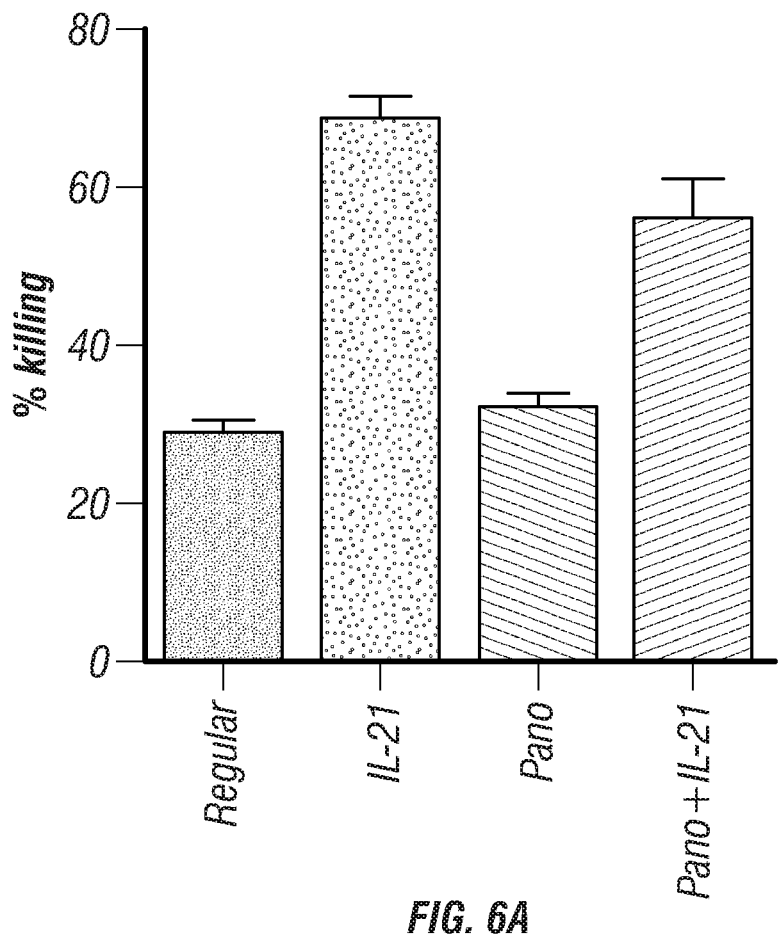
FIGS. 6A-6B: IL-21/Panobinostat-expanded CTLs exhibit augmented tumor killing capability. (A) CRA results demonstrating the percentage of target tumor cell killing by CTLs expanded with the indicated condition. (B) Representative plot of intracellular IFN-γ and granzyme B expression in different CTLs activated by target tumor cells. The numbers within the plots annotate the percentage of cells in each quadrant. The representative results out of two independent experiments are shown. CRA: chromium release assay. Pano: Panobinostat.
Figure 6B:
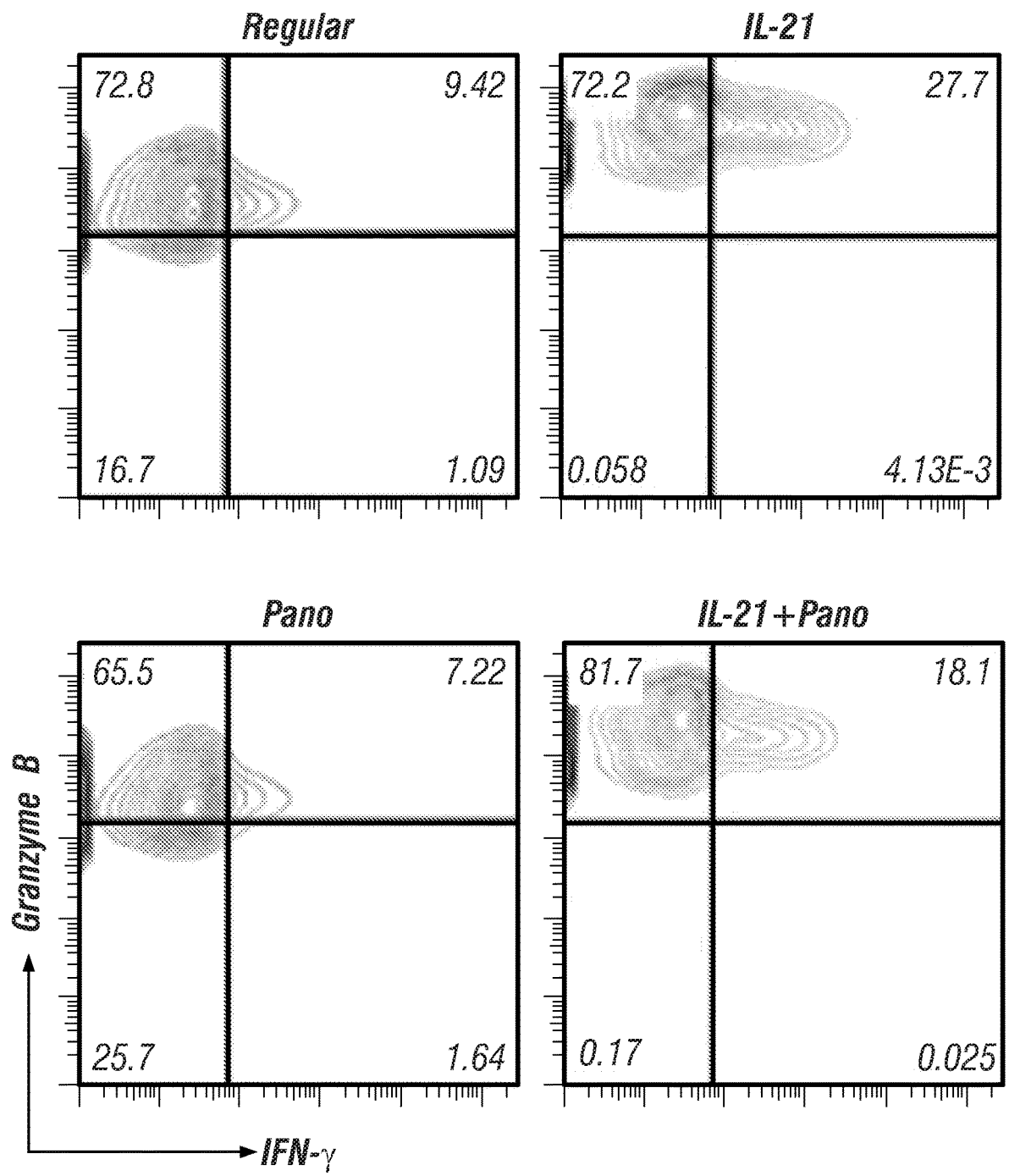

At the end of expansion, a chromium-release assay (CRA) was performed to evaluate tumor killing efficiency of cells expanded under different conditions. IL-21 treatment and the combined panobinostat+IL-21 treatment enhanced tumor cell killing (FIG. 6A). After expansion, the tumor antigen-specific CTL cells were restimulated with tumor cells, followed by intracellular staining. IL-21 augmented IFNγ and granzyme B expression (FIG. 6B).

Figure 7:
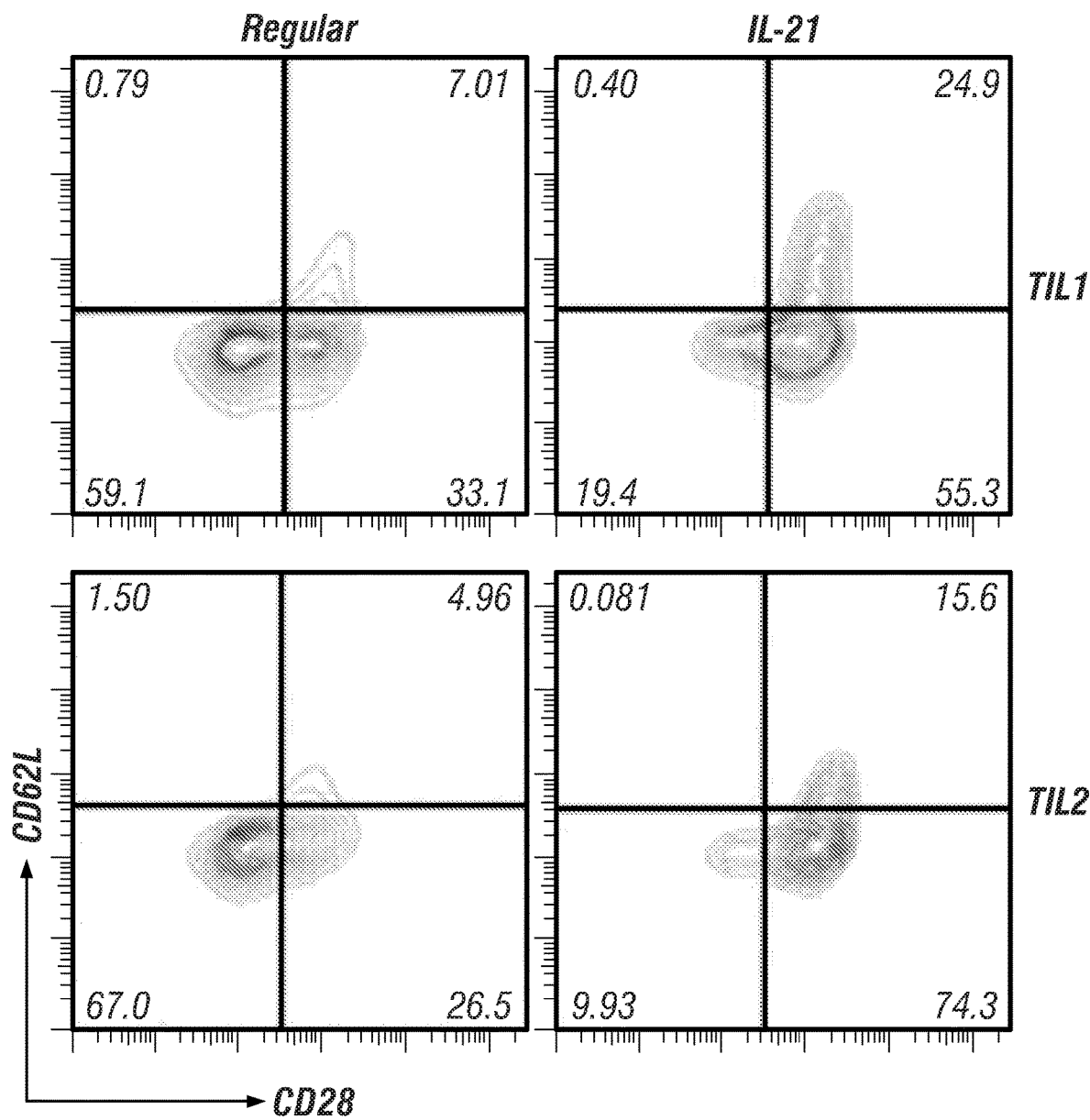
FIG. 7: IL-21 and Panobinostat (Pano) synergize to upregulate CD28 and CD62L expression on TILs. Representative plot of CD28 and CD62L levels on TILs expanded with the indicated conditions for 2 weeks. The numbers within the plots annotate the percentage of cells in each quadrant. TILs: tumor infiltrating lymphocytes.
Figure 7:
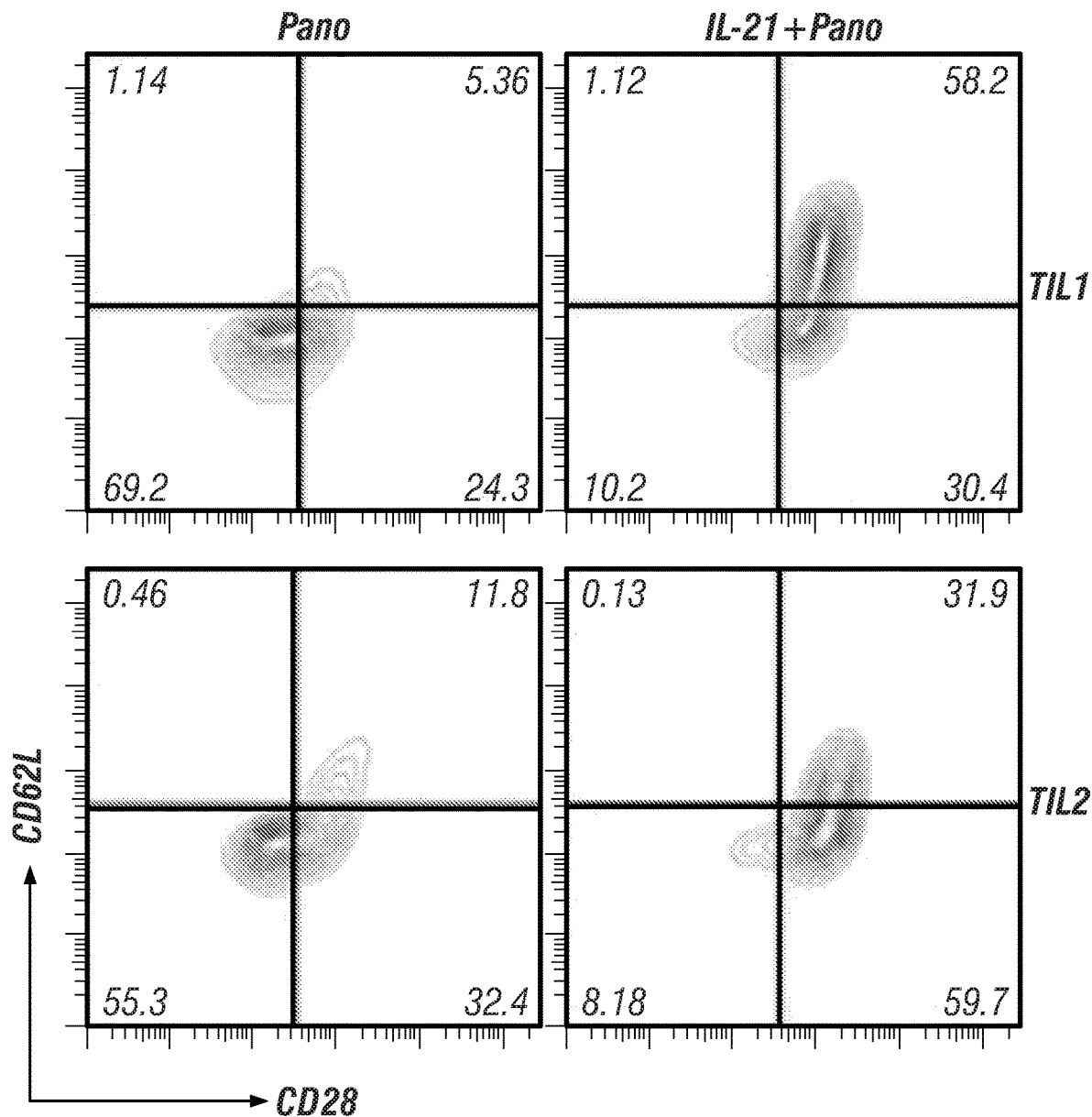

In another experiment, a heterogeneous population of terminally differentiated and non-terminally differentiated TILs were expanded and stained with antibodies against CD8, CD28 and CD62L, and analyzed using the CD8+ gate. IL-21 and panobinostat (Pano) treatment upregulated central memory markers CD28 and CD62L expression on TILs (FIG. 7A).

Thus, the HDACi can be used to reprogram effector T cells so that they become sensitive to memory T cells. In conclusion, the combined IL-21 and HDACi treatment was shown to have a synergistic effect to induce the central memory phenotype from effector T cells and to enhance response to IL-2 and IL-15.

Example 2—Materials and Methods

Expansion of tumor antigen-specific CTL lines or tumor infiltrating lymphocytes (TILs): CTL lines or TILs were expanded using anti-CD3 and irradiated allogeneic PBMCs or Lymphoblastoid Cell Lines (LCLs) (for CTL lines) as feeder cells for rapid expansion. The TILs were cultured from patient melanoma tumors. The cultures were fed with IL-2 at 50 U/ml (for CTL lines) or 6000 U/ml (for TILs) every 3 days. IL-21 (30 ng/ml) or HDACi Panobinostat (3 nM) (as controls) or a combination of IL-21 and HDACi was fed on day 0, 4 and day 7. After 14 days, cells were used for further analyses. For studies with SAHA (FIG. 2), SAHA was used at 1-5 PM.

Flow Cytometry: Cells were stained with antibodies against CD8, CD28, CD62L or CD132. All FACS data were acquired via an LSR II flow cytometer and analyzed via FlowJo software (Tree Star, Inc.).

Intracellular Staining: The cells were restimulated with tumor cells for 16 hours and stained with antibody against CD8, followed by fixation and staining with antibodies against IFN-γ and granzyme B in permeabilization buffer. The cells were washed and resuspended in FACS buffer before analysis.

Quantitative real-time PCR: Total RNA was prepared using Qiagen RNA purification kit. eDNA was made using Superscript reverse transcriptase and oligo(dT) primers (Life Technology), and gene expression was detected with a Bio-Rad iCycler Optical System using iQ SY1BR green real-time PCR kit (Bio-Rad Laboratories, Inc.). The data were normalized to the reference gene RPL13A. RPL13A primer was purchased from Qiagen. Other primer pairs used were: CD28 forward: CTCACACTTCGGGTTCCTCGG (SEQ ID NO:2), reverse: GACTCCACCAACCAC-CACCAG (SEQ ID NO: 3); CD62L forward: ATGGAAC-GATGACGACTGCC (SEQ ID NO: 4), reverse: GGCCTC-CAAAGGCTCACACT (SEQ ID NO: 5); Additional primers included lymphoid enhancer-binding factor 1 (LEFI) forward: CACACCCGTCACACATCCCA (SEQ ID NO: 6), reverse: TGGGAAAACCAGCCAAGAGGTG (SEQ ID NO: 7); transcription factor 1 (TCF1) forward: TGCAGCTATACCCAGGCTGG (SEQ ID NO: 8), reverse: CCTCGACCGCCTCTTCTTC (SEQ ID NO: 9).

Chromatin immunoprecipitation (ChIP): ChIP was performed using a ChIP Assay Kit according to the manufacturer's instructions (Millipore). Quantitative real-time PCR was performed with primers: CD28 promoter proximal STAT sites: forward TCTGCTGGATTTCAAGCACCC (SEQ ID NO:10), reverse GACTGCAGCATTT-CACACAGG (SEQ ID NO: 11); distal STAT sites: forward TGCTTGCACGTAGAATGGGT (SEQ ID NO: 12), reverse GGATGGGGACAGGTTGTGTC (SEQ ID NO: 13); Rabbit IgG was used as a negative control.

Chromium Release Assay (CRA): Tumor cells were labeled with Cr51 before being incubated with antigen-specific CTLs at effector:tumor of 20:1 for 4 hours. The Cr51 amount in the supernatants was measured and the killing efficiency was calculated as % killing=100%× (sample average−average of negative control)/(average of positive control average of negative control).

Mini-REP was started scaling down from T25 flasks to 24-well plates accordingly. IL-21 and Panobinostat dose remained unchanged.

Statistical analysis: Graphical presentation and statistical analysis of the data were performed using GraphPad Prism (Version 6, GraphPad software, San Diego, CA) and Excel. Data are displayed as mean and STD. Results between experimental groups were compared using Student's t test. $p<0.05$ was considered statistically significant. Statistical significance is displayed as *P<0.05, P<0.0, *P<0.001.

Example 3—Reprogramming of Human Effector to Memory CD8$^+$ T Cells

Figure 9D:
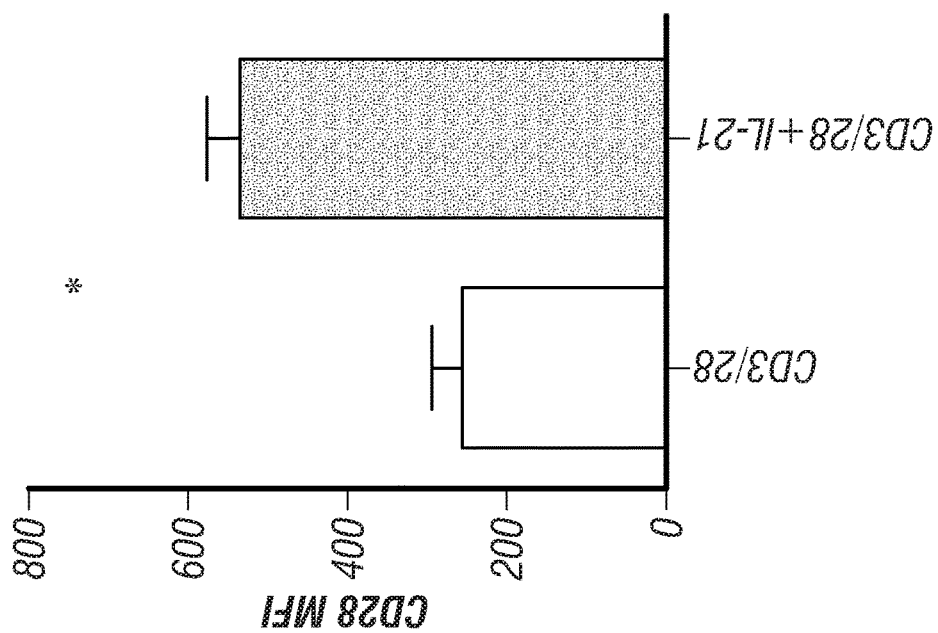
Figure 9C:
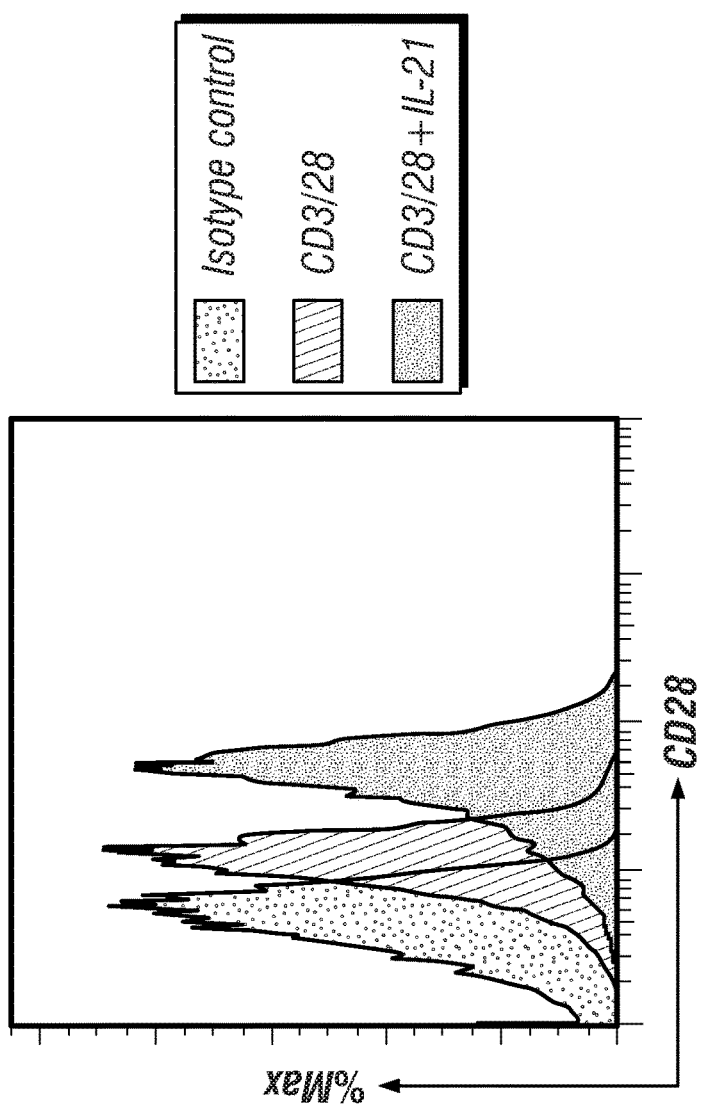
Figure 9F:
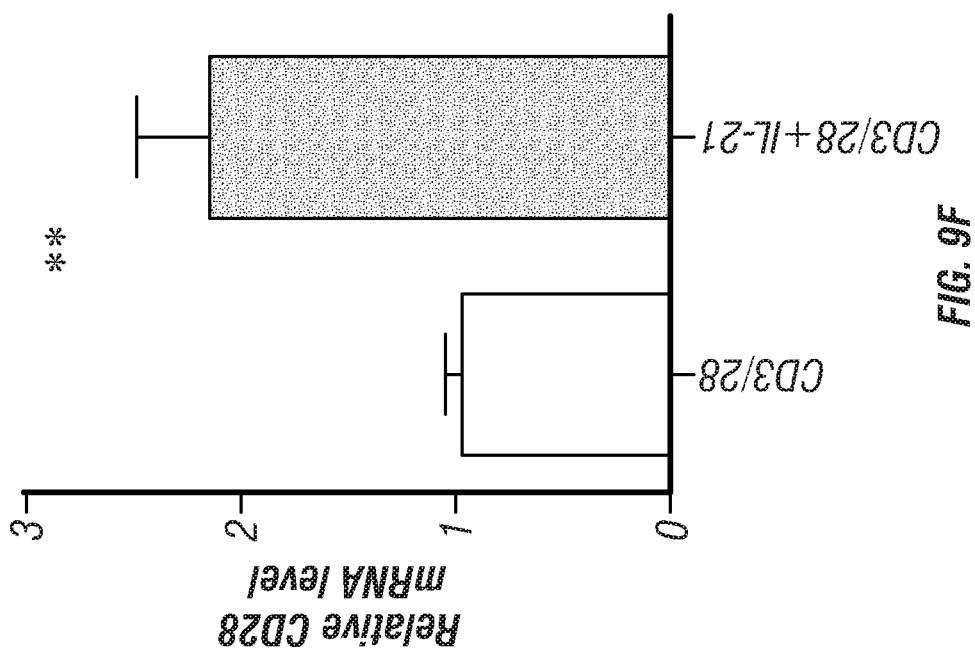
Figure 9E:
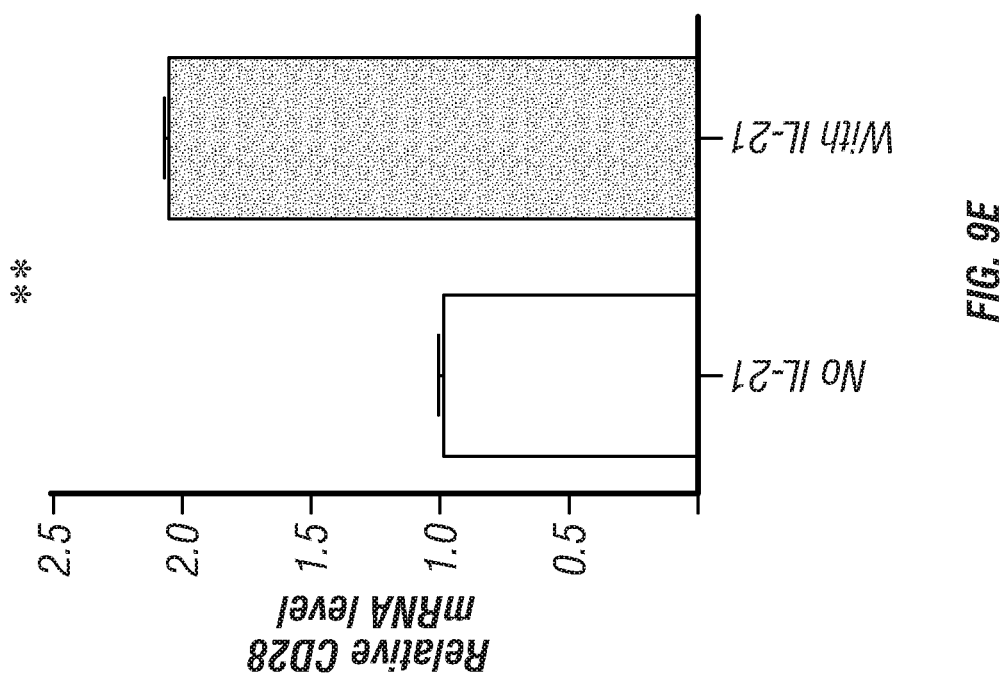

IL-21 upregulates CD28 expression on activated human naïve CD8$^+$ T cells: CD28 is a pivotal costimulatory molecule for naïve T cell activation and memory T cell function. Previous studies comparing the effects of various γC cytokines on the generation of tumor-antigen specific CTLs in vitro found that IL-21 has the unique ability to enrich for CD28$^{hi}$ CTLs that exhibit enhanced persistence and improved patient clinical responses after adoptive transfer. To investigate the molecular mechanisms of IL-21-induced CD28 expression, melanoma antigen recognized by T cells (MART1, M27)-specific CTLs were generated in the absence or presence of IL-21 as previously described (Li et al., 2005). M27-specific CTLs generated with IL-21 displayed significantly higher CD28 expression than cells generated in the absence of IL-21 (FIGS. 9A and B). To further corroborate the findings, sort-purified naïve human CD8$^+$ T cells (CD45RA$^+$CCR7$^+$) from healthy donors were activated with anti-CD3/CD28 beads in the absence or presence of IL-21 and surface CD28 expression was detected by flow cytometry. Consistent with antigen-specific CTLs (FIGS. 9A and B), surface level expression of CD28 was significantly increased in polyclonally activated IL-21-treated human naïve CD8$^+$ T cells (FIGS. 9C and D). In line with enhanced CD28 protein expression, greatly augmented CD28 mRNA level was consistently detected in M27-specific CTLs generated in the presence of IL-21 (FIG. 9E) and in IL-21-treated anti-CD3/CD28 activated human naïve CD8$^+$ T cells (FIG. 9F). Together these results indicated that IL-21 upregulates CD28 mRNA expression to increase CD28 surface level expression.

STAT3 activation is required for IL-21-mediated enhancement of CD28 expression: IL-21 functions through activation of Janus-activated kinase 1 (JAK1) and JAK3 and subsequent phosphorylation of signal transducer and activator of transcription (STAT)-3 and, to a lesser extent, STAT1 and STAT5. Thus, the phosphorylation of STAT1, STAT3 and STAT5 was examined in naïve CD8$^+$ T cells under the culture conditions. Human naïve CD8$^+$ T cells from healthy donors were activated with anti-CD3/CD28 beads in the absence or presence of IL-21 for different periods of time. IL-21 stimulation induced strong STAT1 and STAT3 phosphorylation but weak STAT5 phosphorylation 30 minutes after activation (FIG. 16A). Since IL-21 induces strong STAT1 and STAT3 activation, the studies aimed to elucidate whether STAT1 and/or STAT3 activation was essential for CD28 upregulation by IL-21. To examine the role of STAT3, peripheral blood mononuclear cells (PBMCs) from Job's syndrome patients were used. Job's syndrome (also known as hyper-IgE syndrome, characterized by abnormally high levels of immunoglobulin E (IgE) in the blood) is caused by diminished STAT3 functions due to dominant negative mutations in the STAT3 gene. Total CD8$^+$ T cells were isolated from PBMCs of healthy donors or Job's syndrome patients and activated as described above. IL-21 increased the expression of CD28 at both the protein and mRNA levels in CD8$^+$ T cells from healthy donors, however, IL-21-mediated enhancement of CD28 expression was completely abrogated in cells from Job's syndrome patients (FIG. 17A-C). These results indicated that STAT3 activity is important for the upregulation of CD28 expression by IL-21 in activated human CD8$^+$ T cells.

Figure 10A:
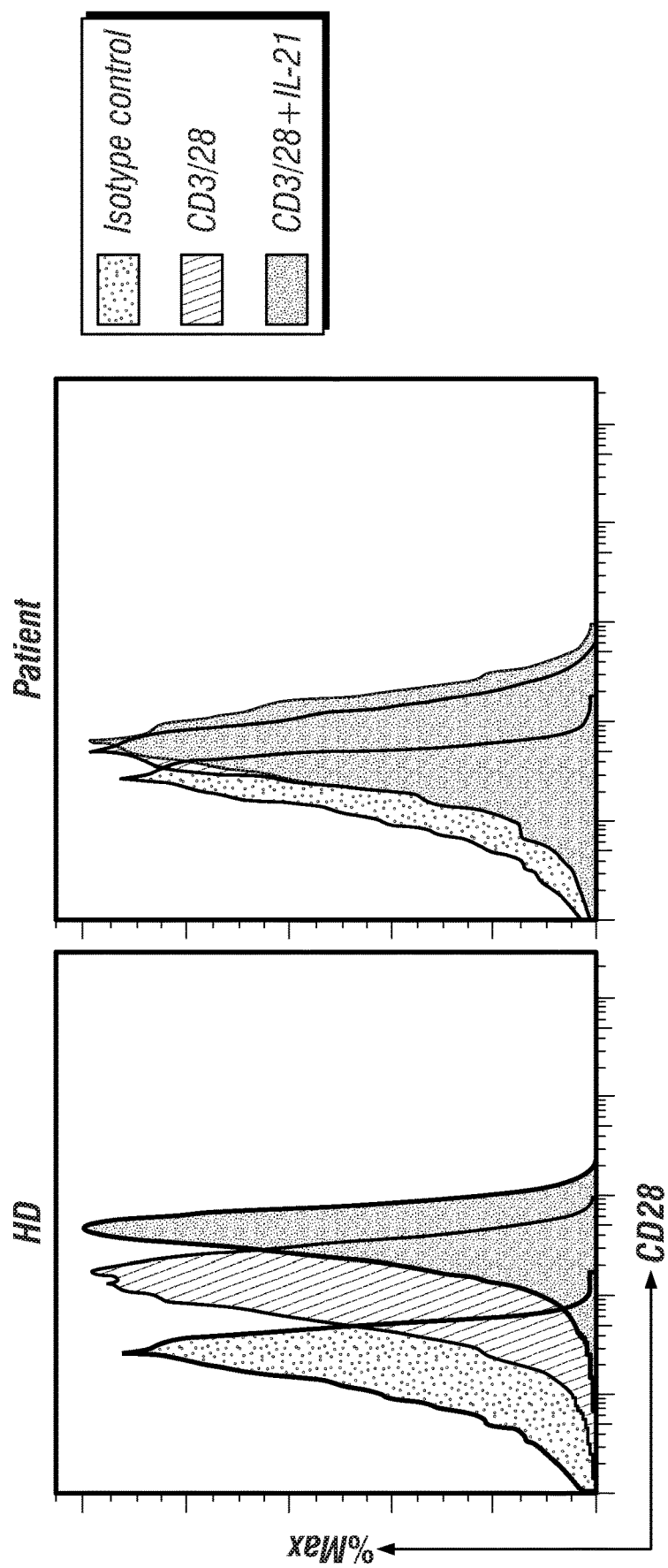
Figure 10C:
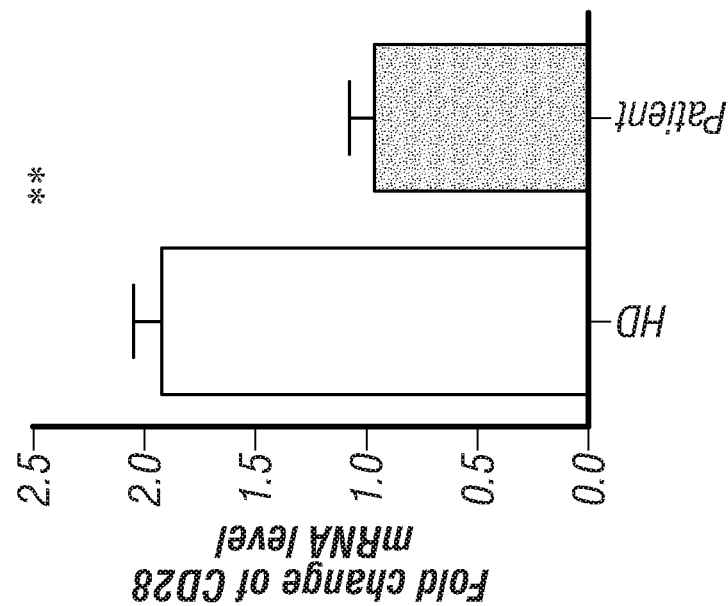
Figure 10B:
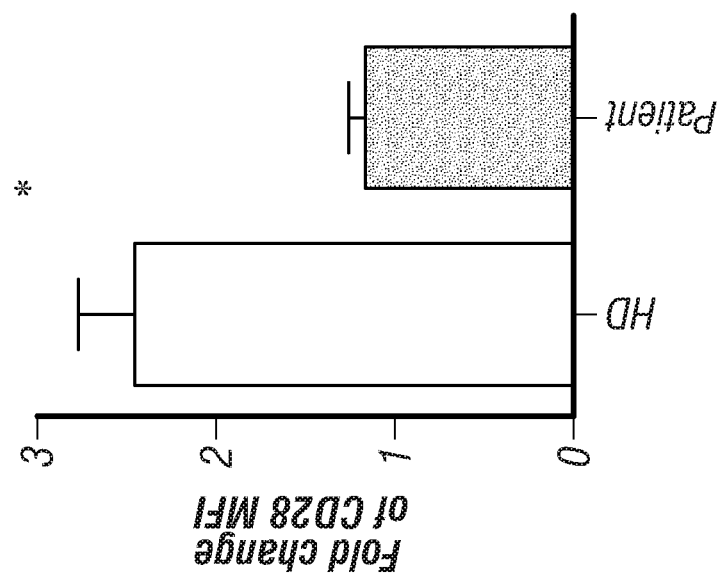
Figure 10D:
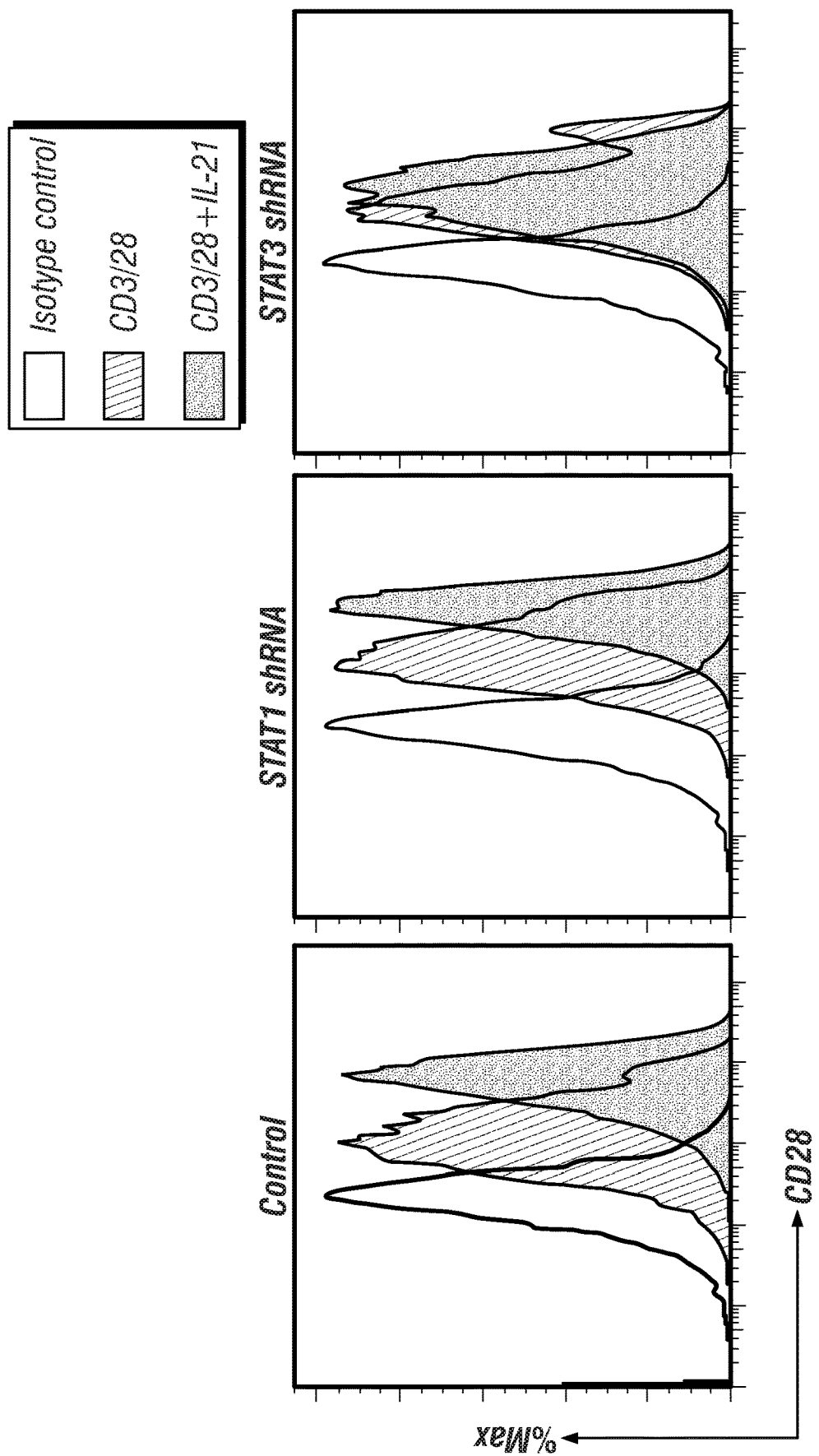
Figure 10G:
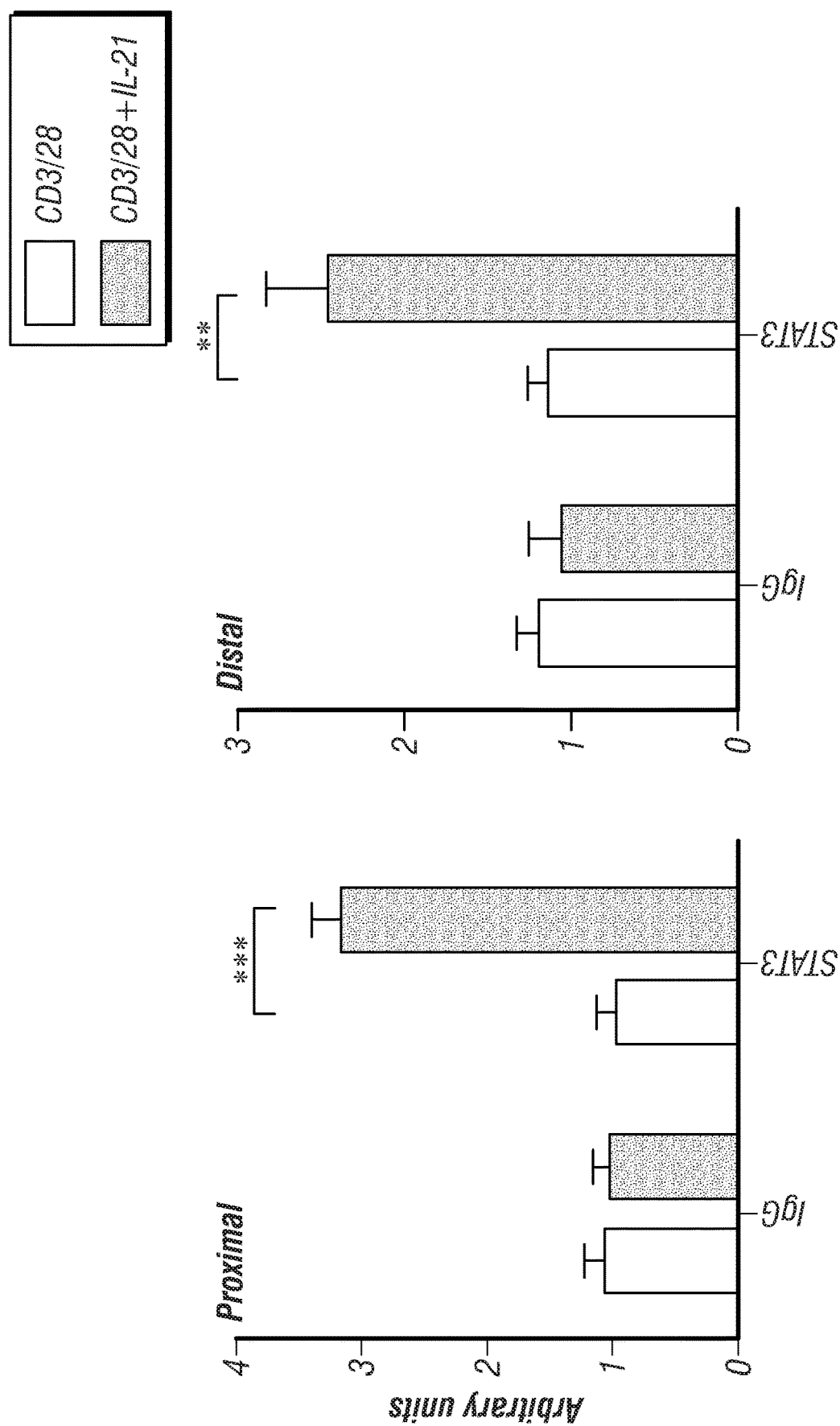

To further affirm the findings and also assess the role of STAT1 in IL-21-induced CD28 upregulation, different shRNA constructs targeting various regions of the human STAT1 or STAT3 genes were used to knockdown STAT1 or STAT3 expression in untreated human CD8$^+$ T cells. Total STAT1 and STAT3 levels showed that STAT1 or STAT3 shRNA specifically and efficiently decreased expression of their respective proteins (FIG. 16B). As shown in FIGS. 10D-F, compared to control cells, IL-21-induced CD28 protein and mRNA upregulation was diminished in STAT3 shRNA-transfected and activated CD8$^+$ T cells, but not in STAT1 shRNA-transfected and activated cells. These results supported the critical role of STAT3, but not STAT1, in IL-21-induced upregulation of CD28 expression in activated human CD8$^+$ T cells. Consistent with the findings, a previous study of STAT3 mutant, STAT1 mutant, and IL21R mutant patient cells indicated that IL21/STAT3, but not STAT1, is required for differentiation of CD8$^+$ central memory (CD45RA$^-$CCR7$^+$) and effector memory (CD45RA$^-$CCR7$^-$) cells in vivo.

To further delineate the molecular mechanism by which STAT3 mediates IL-21-induced upregulation of CD28 expression in activated human CD8$^+$ T cells, the human CD28 promoter was analyzed and several consensus STAT sites were identified clustered in the proximal and distal part of the CD28 promoter. ChIP assays showed a 2-3 fold enrichment of STAT3 at both proximal and distal CD28 promoter regions in cells activated with anti-CD3/CD28 and IL-21, relative to anti-CD3/CD28 treatment alone (FIG.

10G). Collectively, these results suggested that IL-21-activated STAT3 binds to the human CD28 promoter to promote CD28 transcription.

Figure 11A:
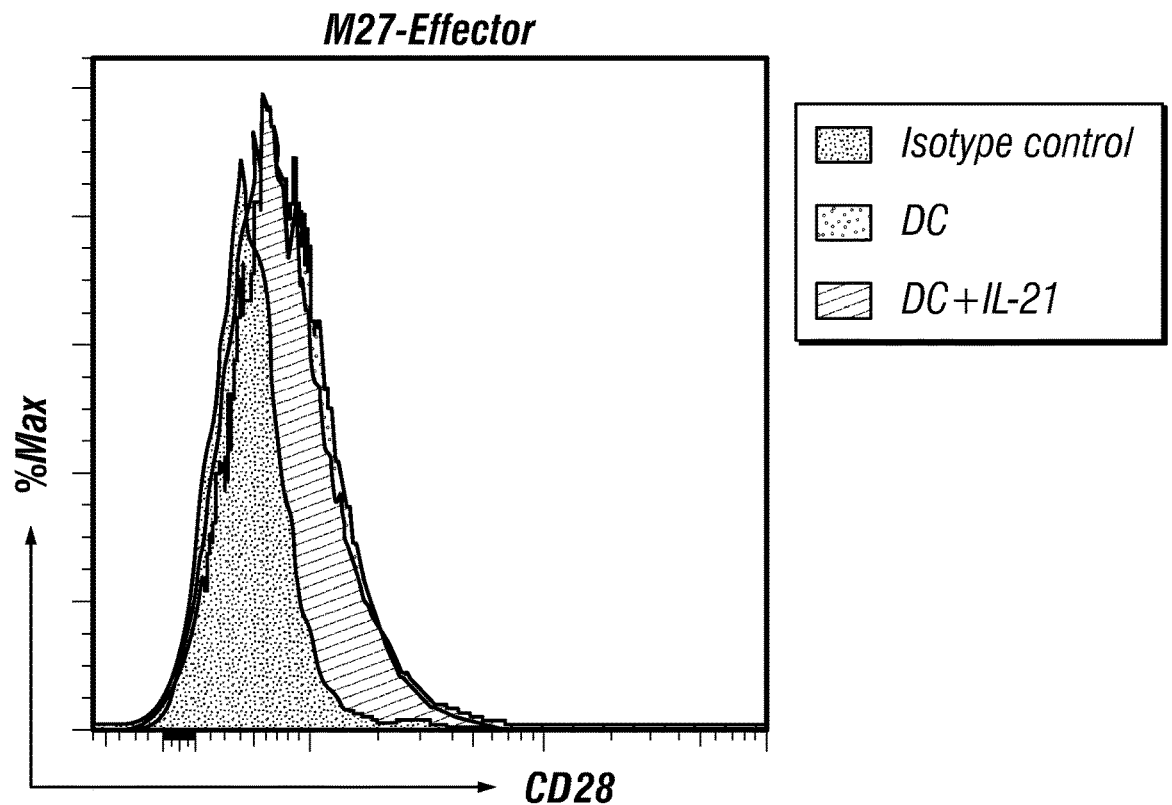
FIGS. 11A-11F: The differential induction of CD28 in response to IL-21 correlates with histone H3 acetylation levels in naïve and effector $CD8^+$ T cells. (A-B) Representative histogram and summary of CD28 levels on M27-specific effector $CD8^+$ T cells activated with M27-pulsed mature dendritic cells in the presence or absence of IL-21 for 4 days. Isotype antibody was used as a negative staining control. [n=3; mean±SEM; ns: not significant; paired t test]. (C) Western blot results of IL-21-induced pSTAT3 in naïve and M27-specific effector CTLs. STAT3 and β-actin were used as loading controls. The bands were quantified using ImageJ and normalized to the density of actin in the corresponding samples. Molecular weight is indicated in kilodaltons. UT: untreated. (D) ChIP results of H3 acetylation level on the CD28 promoter comparing Naïve to $CD45RA^+EM$ ($T_{EMRA}$) $CD8^+$ T cells. The results were normalized to the percentage of the input amount. TSS: transcription start site. [n=3; mean±SEM; * $p<0.05$, *** $p<0.001$; two-way ANOVA]. (E) Representative histogram of CD28 levels on naïve and $T_{EMRA}$ $CD8^+$ T cells activated with anti-CD3/CD28 or together with IL-21 for 4 days. (F) ChIP results of H3 acetylation level on the CD28 promoter comparing Naïve to M27-specific effector $CD8^+$ T cells. The results were normalized to the percentage of the input amount.
Figure 11B:
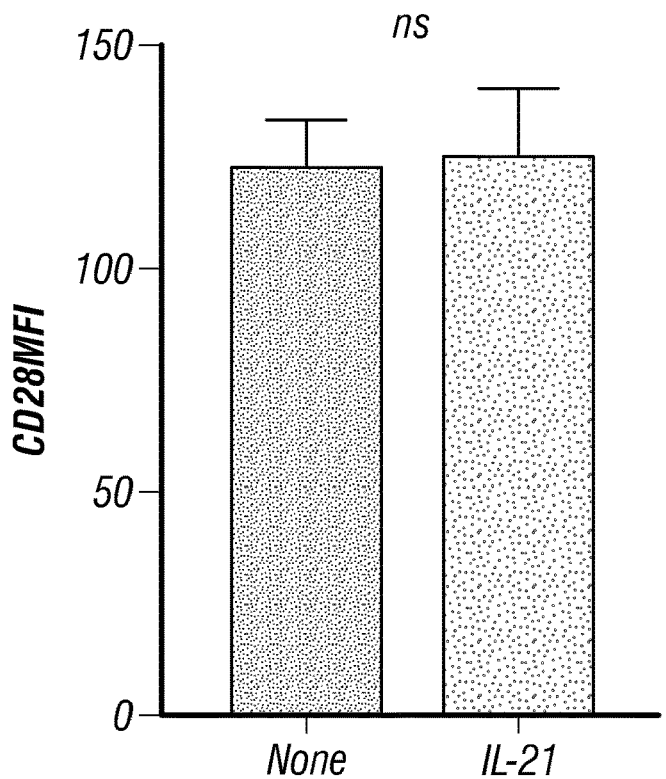
Figure 11C:
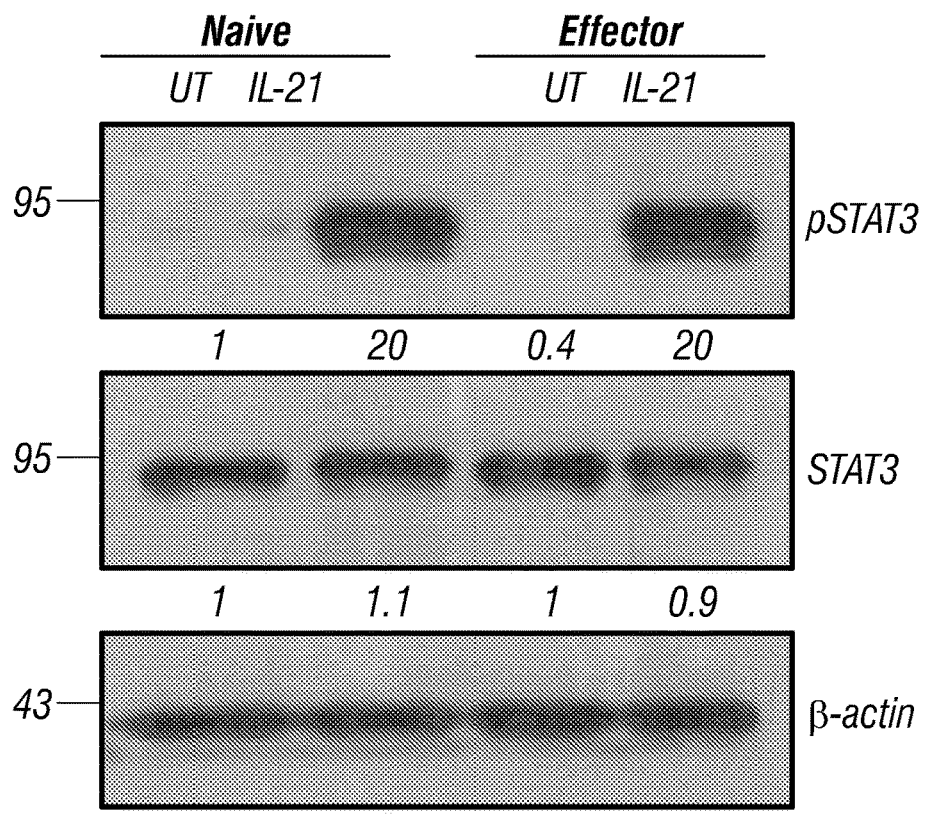

The differential induction of CD28 in response to IL-21 correlates with histone H3 acetylation levels in naïve and effector CD8$^+$ T cells: The studies demonstrated that IL-21 uniquely enhances CD28 expression on naïve CD8$^+$ T cells following activation (FIG. 9). However, the induction of CD28 by IL-21 was not observed on MART1 (M27)-specific effector CD8$^+$ T cells activated with their cognate peptide-pulsed mature dendritic cells (FIGS. 11A and B). Since IL-21 functions mainly through phosphorylation of STAT3 (FIG. 10), IL-21-induced STAT3 phosphorylation levels were compared in naïve and effector CD8$^+$ T-cells and were found to be comparable (FIG. 1 IC), suggesting that the inability of IL-21 to increase CD28 expression on effector CD8$^+$ T cells was not due to absence of IL-21 signaling, but to lack of access of pSTAT3 to its binding sites.

Figure 11D:
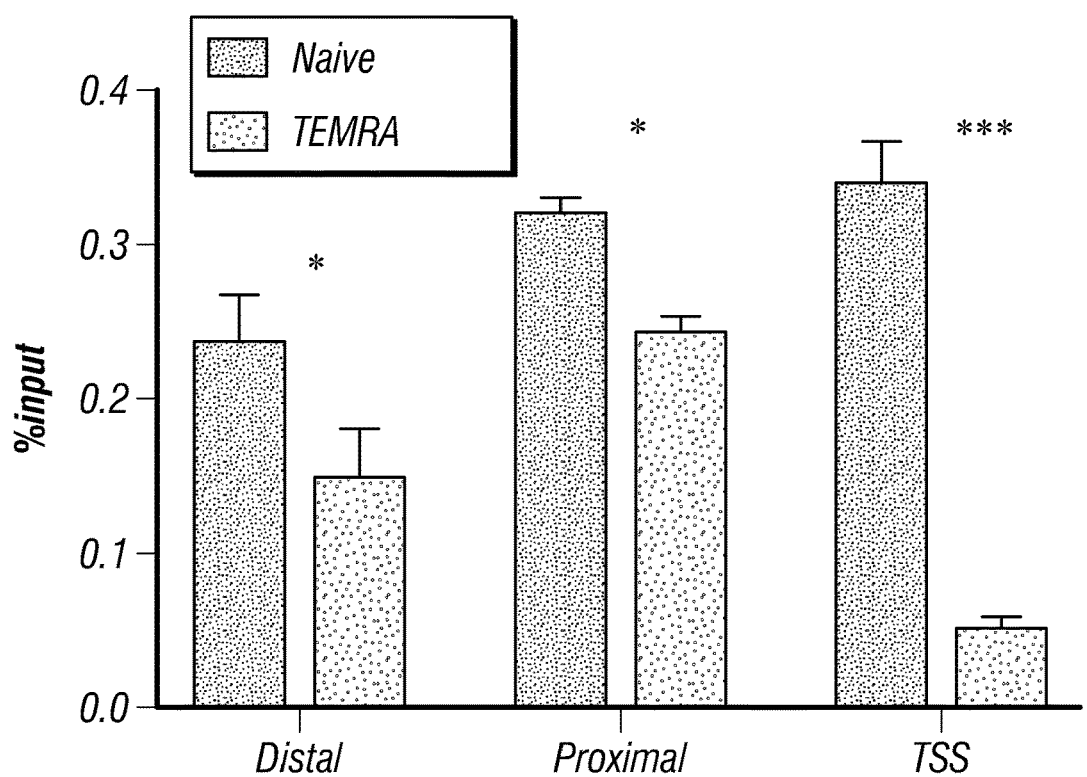
Figure 11E:
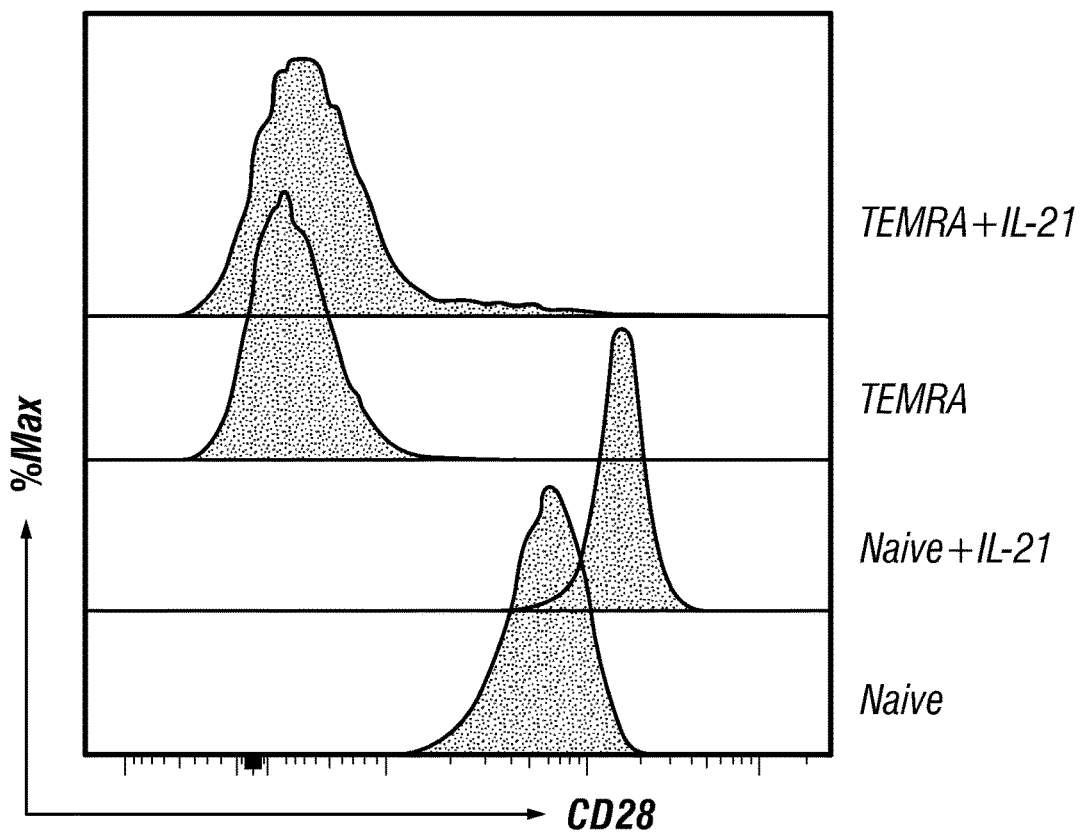
Figure 11F:
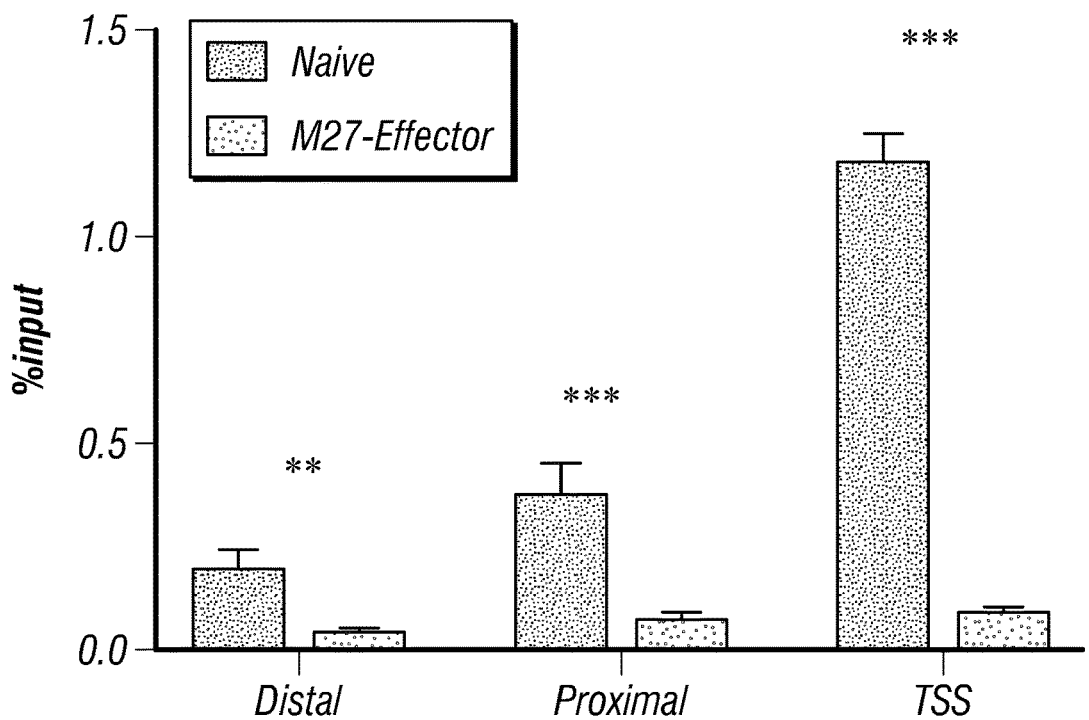

Chromatin accessibility and gene expression can be regulated by histone acetylation. To determine whether histone acetylation level correlates with CD28 expression, chromatin immunoprecipitation (ChIP) was performed on naïve (CD45RA$^+$CCR7$^+$) and T$_{EMRA}$ effector memory (CD45RA$^+$ CCR7$^-$) CD8$^+$ T cells, which have high and low CD28 levels, respectively. In line with their high CD28 expression, naïve CD8$^+$ T cells showed increased acetylated histone H3 (AcH3) around the distal and proximal STAT3 binding sites on the promoter and around the transcription start site (TSS) of the CD28 gene, compared to T$_{EMRA}$ CD8$^+$ T cells (FIG. 11D). IL-21 treatment minimally upregulated CD28 expression in activated T$_{EMRA}$ CD8$^+$ T cells (FIG. 11E). Similarly, MART1 (M27)-specific CD28neg effector CD8$^+$ T cells displayed significantly decreased AcH3 levels on the CD28 locus, compared to naïve CD8$^+$ T cells (FIG. 11F). These results indicated that CD28 transcription is regulated by histone acetylation, which correlates with the differential induction of CD28 by IL-21 in naïve and effector CD8$^+$ T cells. Therefore, modulation of AcH3 could allow IL-21-mediated CD28 upregulation in effector CD8$^+$ T cells.

SAHA allows IL-21-induced pSTAT3 to access the CD28 promoter and to upregulate CD28 expression in effector CD8$^+$ T cells: The above findings indicated that CD28 transcription is regulated by histone acetylation, which suggests that reduction of histone acetylation levels may lead to CD8$^+$ T cell differentiation and loss of naïve/central memory marker expression. It was hypothesized that increasing histone acetylation through the use of HDACi would reverse CD8$^+$ T cell differentiation. Since IL-21 significantly enhances CD28 expression on naïve CD8$^+$ T cells (FIG. 9), which have higher levels of histone acetylation (FIG. 11D), it was reasoned that the combination of HDACi and IL-21 would have a synergistic effect on CD28 expression. To test the hypothesis, the effect of a clinically available compound, Suberoylanilide Hydroxamic Acid (SAHA, Vorinostat), a broad histone deacetylase inhibitor (HDACi), that is approved to treat cutaneous T-cell lymphoma and has been used in clinical trials to treat other diseases was assessed. Titration studies to determine effective dose showed that SAHA at concentrations of 1p M or greater could augment AcH3 levels in effector CD8$^+$ T cells (FIG. 16).

Figure 12A:
Figure 12B:
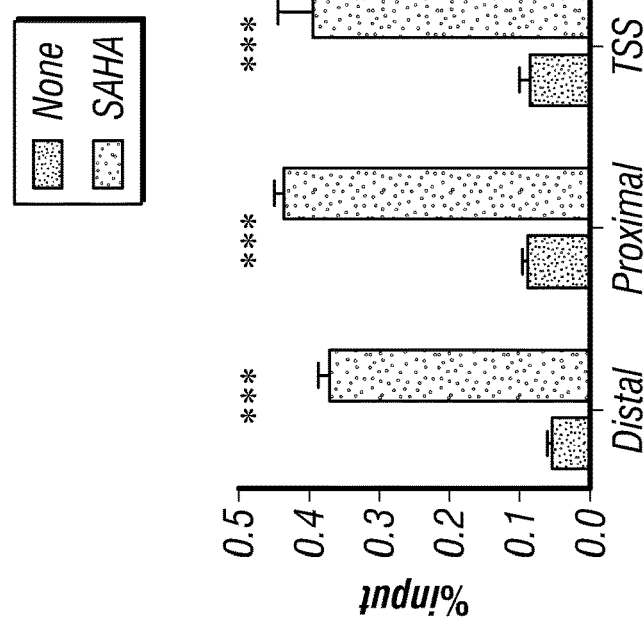
Figure 12D:
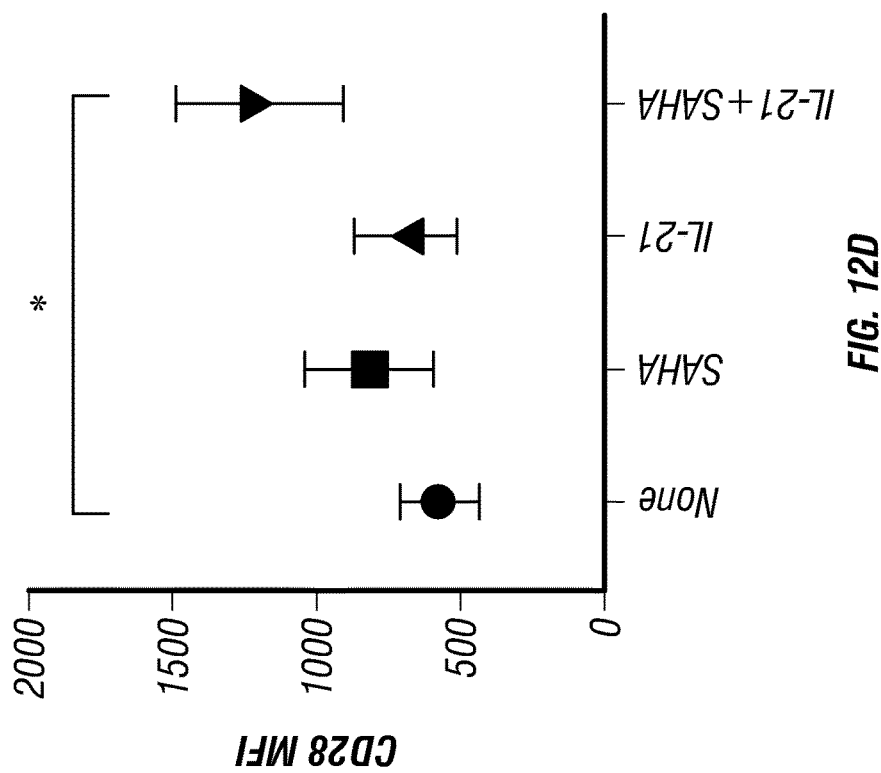
Figure 12C:
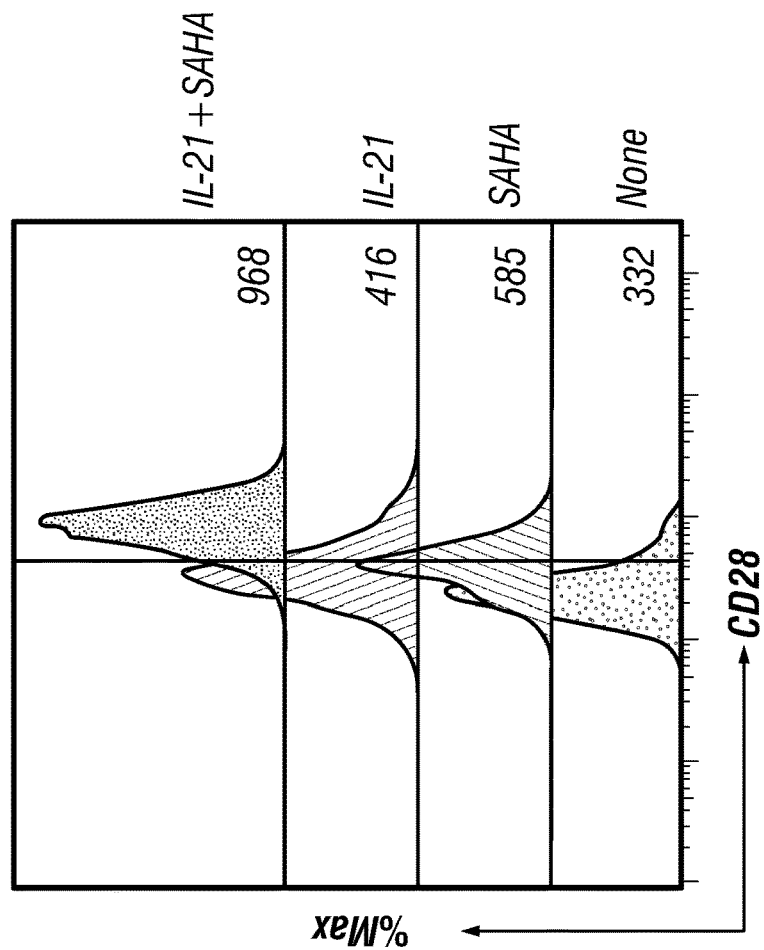
Figure 12E:
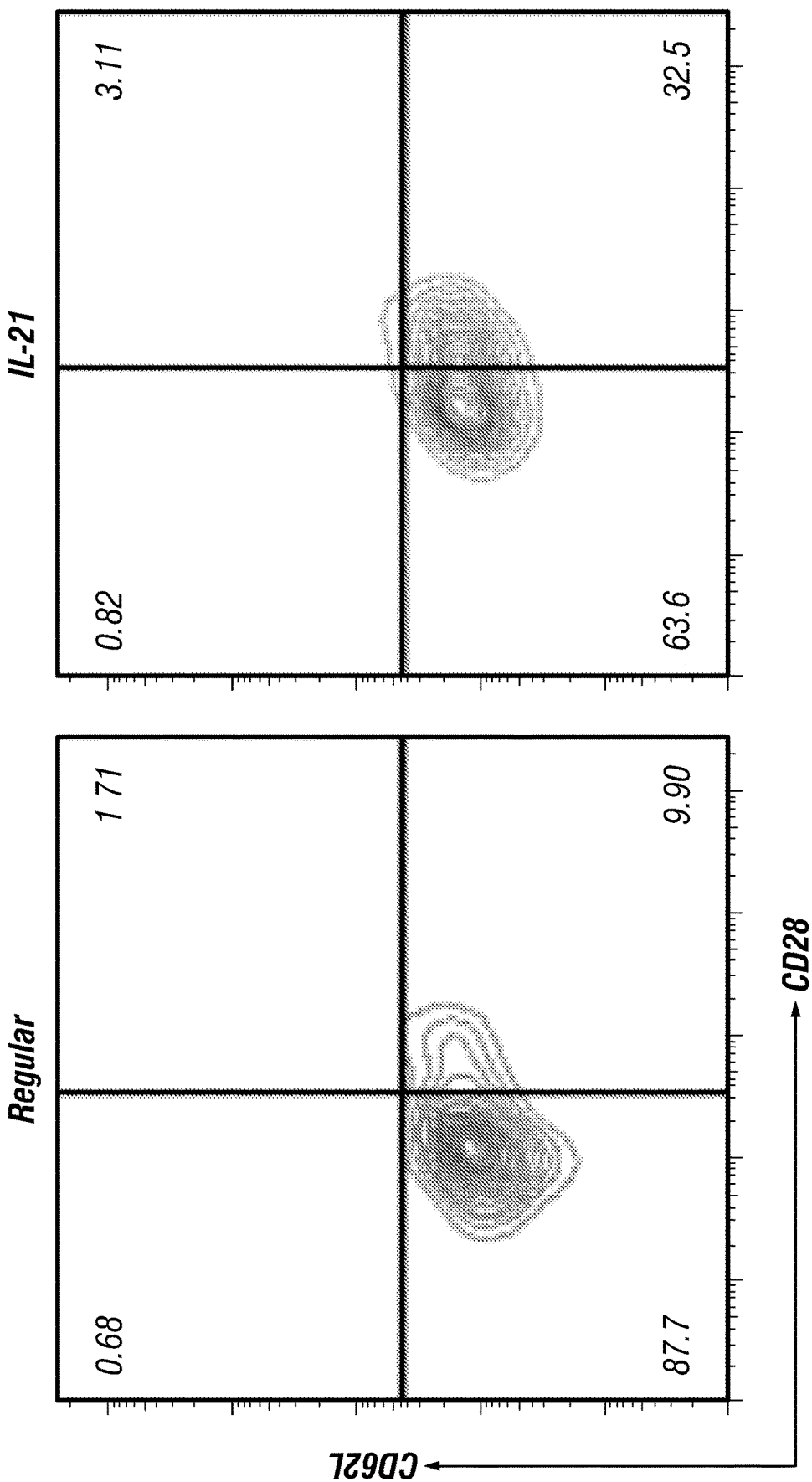

To assess the effect of SAHA/IL-21 on CD28 expression in the context of a more physiologic, antigen-specific (in contrast to non-specific polyclonal) stimulation, this effect was evaluated on MART1 (M27)-specific effector/effector memory cells generated using peptide-pulsed autologous dendritic cells. MART1 (M27)-specific effector CD8$^+$ T cells (CD45RO$^+$, CD28-neg, CD62L-neg) were generated following iterative cycles of in vitro stimulation, tetramer-guided sorting of M27-specific CTL and expansion to uniformity (>95% MART-1-specific effector CTL). First, the effect of SAHA was evaluated on pSTAT3 binding to the CD28 promoter region. SAHA treatment significantly increased AcH3 levels on the promoter and TSS region of CD28 gene (FIG. 12A). In correlation with increased AcH3 levels, SAHA treatment increased IL-21-induced pSTAT3 binding to the CD28 promoter (FIG. 12B). Next, M27-specific effector CD8$^+$ T cells were left untreated or pretreated with SAHA for 24 hours, followed by activation with M27-pulsed mature dendritic cells in the presence or absence of SAHA/IL-21 for 4 days. Interestingly, SAHA and IL-21 together significantly enhanced CD28 expression (FIGS. 12C and D), demonstrating the cooperative effect of SAHA and IL-21 on CD28 expression. These results suggested that SAHA treatment increased AcH3 level and chromatin accessibility in M27-specific effector CD8$^+$ T cells, thus allowing IL-21-activated STAT3 to bind to its promoter sites and induce CD28 expression.

IL-21 and SAHA synergize to upregulate CD28 and CD62L expression: To assess the effect of SAHA/IL-21 in the translational setting, this program was evaluated on tumor-infiltrating lymphocytes (TIL). Adoptive transfer of TIL cells for the treatment of patients with metastatic melanoma, and other TIL$^+$ solid tumors, involves extraction of infiltrating lymphocytes from tumor biopsies, in vitro treatment with high dose IL-2, in vitro expansion with a Rapid Expansion Protocol (REP) and then infusion of ex vivo expanded TILs following high dose lymphodepletion conditioning. Although TIL therapy has shown some success in the treatment of metastatic melanoma patients, many patients do not respond to TIL therapy, partly due to limited persistence of the infused cells. CD8$^+$ T cells in TIL products are usually well-differentiated effector, effector memory, and terminal effector cells with reduced proliferative ability. To examine the possible de-differentiating effect of an HDAC inhibitor/IL-21 combination, TILs were untreated or pretreated with SAHA for 24 hours, then subjected to regular REP (irradiated PBMC and LCL cells, anti-CD3 and IL-2), or REP with SAHA/IL-21. Adding SAHA alone to REP culture caused dramatic cell death and hemocytometer counting showed there were few viable cells at the end of REP. Compared to REP alone or REP with IL-21 alone, SAHA and IL-21 given in combination during REP increased not only CD28 but also CD62L expression (FIGS. 12E and F), two markers highly expressed on naïve and central memory T cells. These results suggested that, similar to the results in M27-effector CD8$^+$ T cells, SAHA treatment increased AcH3 level and chromatin accessibility in TILs, thus allowing IL-21-activated STAT3 to bind to its promoter sites and induce CD28 expression and phenotypic evidence of de-differentiation of effector CD8$^+$ T cells.

IL-21 and Panobinostat (Pano) cooperate to induce central-memory-like T cells: Since the cytotoxicity of SAHA limits its application in ACT other pharmacologically available HDACi (FIG. 17A) were screened and it was found that Panobinostat (LBH589, Pano) had an effect similar to that of SAHA but with minimal cytotoxicity. Panobinostat increased AcH3 level at 0.5 nM or higher doses (FIG. 17B). The effect of Panobinostat was initially investigated on TILs in REP at a small scale and compared pretreatment (pretreating cells with Panobinostat for 24 hours before rapid expansion with Pano and IL-21) with co-treatment (adding Panobinostat and IL-21 when starting cell expansion). Since these two strategies had comparable effects in inducing a CD28+CD62L+ cell population for TILs (FIGS. 18A and 18B), the co-treatment scheme was followed in subsequent studies for simplicity.

To examine the clinical applicability of Panobinostat (Pano) in the setting of antigen-specific ACT, MART1 (M27)-specific effector/effector memory cells generated via the ETC approach were used and expanded in vitro by REP, as previously described (Yee, 2014). Cells were expanded with four different protocols (regular, adding IL-21 alone, adding Pano alone, or IL-21+Pano). Though adding Panobinostat alone to REP slightly reduced the overall yield, expansion fold was similar for the other three conditions (FIG. 18C). Addition of Panobinostat induced a CD28+ CD62L+ cell population that was further enhanced when combined with the addition of IL-21 (FIGS. 13A and B). It was posited that Panobinostat, like SAHA, enabled STAT3 and other transcription factors/cofactors to access binding sites and induce CD28 and CD62L expression.

Figure 14A:
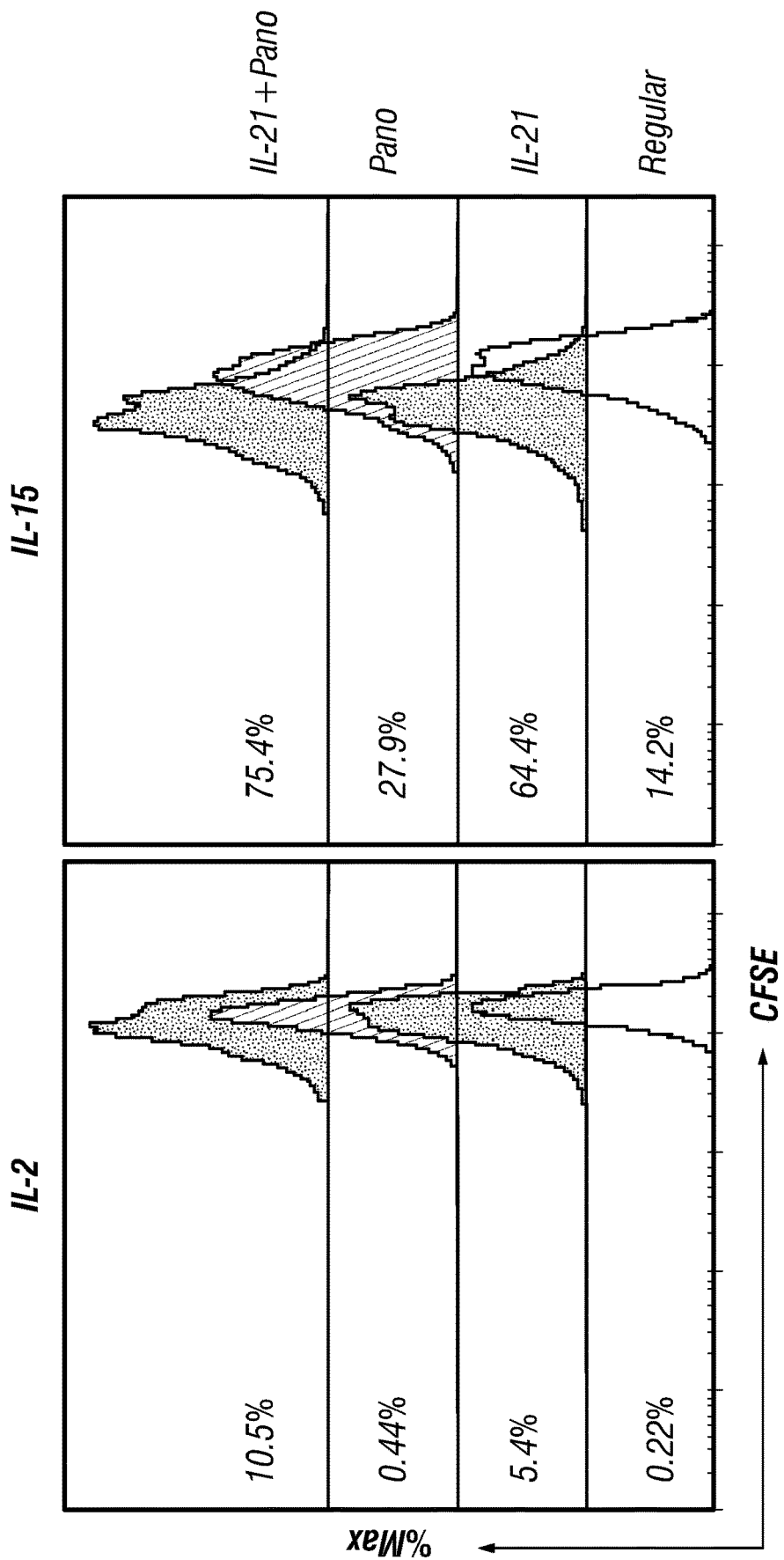

Central memory function associated with the IL-21/Pano-induced CD28+CD62L+ population was evaluated by the ability of these central memory-like T cells to undergo homeostatic proliferation in response to IL-7 and IL-15. ETC cells expanded with four different protocols (regular, adding IL-21 alone, adding Pano alone, or IL-21+Pano) were labeled with CFSE and cultured with IL-2, IL-7 or IL-15 for 2 days. IL-7 did not induce cell division, likely due to low levels of CD127 expression. Cells expanded in the presence of IL-21 exhibited enhanced IL-2- and IL-15-induced proliferation (FIG. 14A). Adding Panobinostat alone to REP increased cell proliferation in response to IL-15 but not to IL-2. Intriguingly, the cells expanded with the combination of IL-21 and Panobinostat exhibited greater proliferative responses to IL-2 and IL-15 than any other cohort (FIG. 14A). Since IL-2 and IL-15 share CD132 (γC) and CD122 receptor subunits, CD132 and CD122 levels were assessed on the surface of these cells. Treatment with IL-21+/−Panobinostat led to significantly increased surface CD132 levels (FIGS. 14B and C), which could contribute to their increased self-renewal to IL-2 and IL-15.

Figure 14D:
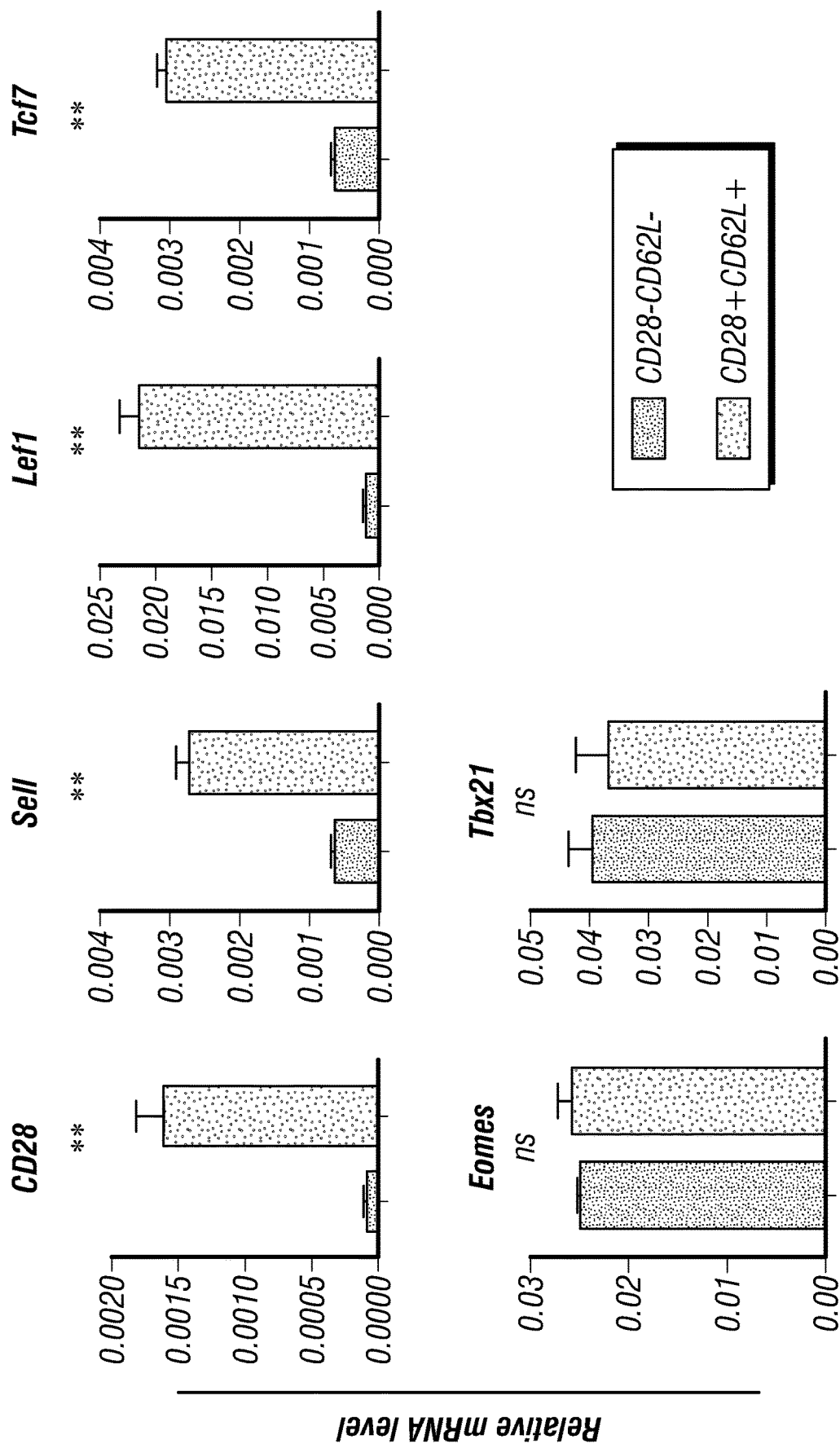

To further confirm the central-memory-like properties of HDACi/IL-21 treated CTL, expression of relevant differentiation genes was assessed. The central memory-associated transcriptional signature (Lef1$^{hi}$, Tcf7$^{hi}$), known to play a role in central memory/stem cell memory CD8+ T cell differentiation, was found to be highly expressed among CD28+CD62L+ cells generated by the combination of Panobinostat and IL-21 treatment (FIG. 14D). The transcription factors T-bet and eomesodermin (Eomes) have essential roles in effector and memory T cell formation, and their expression is increased in differentiated CD8+ T-cells. Interestingly, Tbx21 and Eomes expression was similar between CD28+CD62L+ cells and CD28−CD62L− cells (FIG. 14D).

In this study, it was demonstrated that the combination of IL-21 and HDACi may be used to re-program effector cells to become less differentiated, central memory-like T cells with high replicative capacity. Overall, the potential application of IL-21+Pano approach to two clinically-relevant ACT modalities was demonstrated: ETC and TIL. The study has demonstrated a translatable approach to generate less-differentiated ACT product that would lead to improved clinical outcome.

Example 4—Materials and Methods

Expansion of tumor antigen-specific CTL lines or tumor infiltrating lymphocytes (TILs): CTL lines or TILs were expanded using anti-CD3 and irradiated allogeneic PBMCs or Lymphoblastoid Cell Lines (LCLs) (for CTL lines) as feeder cells for rapid expansion. The TILs were cultured from patient melanoma tumors. The cultures were fed with IL-2 at 50 U/ml (for CTL lines) or 6000 U/ml (for TILs) every 3 days. IL-21 (30 ng/ml) or HDACi Panobinostat (3 nM) (as controls) or a combination of IL-21 and HDACi was fed on day 0, 4 and day 7. After 14 days, cells were used for further analyses. For studies with SAHA, SAHA was used at 1-5 µM.

Polyclonal stimulation of CD8+ T cells: Naïve CD8+ T cells (CD8+CD45RA+CCR7+) were flow cytometry-sorted or were isolated using EasySep™ Human Naïve CD8+ T Cell Enrichment Kit (StemCell). In some experiments, total CD8+ T cells were negatively selected using EasySep™ Human CD8+ T Cell Enrichment Kit (StemCell). The purity of the naïve or total CD8+ T cells was greater than 95% as determined by flow cytometry. CD8+ T cells were cultured in RPMI 1640 with 10% fetal bovine serum and penicillin/streptomycin. CD8+ T cells were activated using Dynabeads® Human T-Activator CD3/CD28 for T-Cell Expansion and Activation (Life Technologies) at a bead:cell ratio of 1:1 or together with 30 ng/mL human IL-21 (Peprotech). At the indicated time points, T cells were harvested and beads were removed using a magnet before downstream analysis.

Cell culture and Rapid expansion protocol (REP): The medium for CTL lines was RPMI1640, 10% FBS, 4 µM Glutamine, and 2-Mercaptoethanol. TILs were cultured in 50% AIM-V, 50% TIL complete medium which contains RPMI1640, 10% human AB serum, 10 mM HEPES, and 2-Mercaptoethanol. For REP, CTL lines or TILs were expanded using 30 ng/mL anti-CD3 (OKT3) and 200× irradiated allogeneic PBMCs or LCLs as feeder cells. The cultures were fed with IL-2 at 50 U/ml every 3 days. IL-21 (30 ng/ml) or HDACi SAHA (1-5 µM) or Panobinostat (1-3 nM) was added on day 0, 4 and 7 if included in the expansion. After 14 days, expanded cells were subjected to further analyses.

Flow Cytometry: Cells were stained with antibodies against CD8, CD28, CD62L or CD132. All FACS data were acquired via an LSR II flow cytometer and analyzed via FlowJo software (Tree Star, Inc.).

Intracellular Staining: The cells were restimulated with tumor cells for 16 hours and stained with antibody against CD8, followed by fixation and staining with antibodies against IFN-γ and granzyme B in permeabilization buffer. The cells were washed and resuspended in FACS buffer before analysis.

Quantitative real-dime PCR: Total RNA was prepared using Qiagen RNA purification kit. cDNA. was made using Superscript reverse transcriptase and oligo(dT) primers (Life Technology), and gene expression was detected with a Bio-Rad iCycler Optical System using iQ SYBR green real-time PCR kit (Bio-Rad Laboratories, Inc.). The data were normalized to the reference gene RPL13A. RPL13A primer was purchased from Qiagen. Other primer pairs used were: CD28 forward: CTCACACTTCGGGTTCCTCGG (SEQ ID NO:2), reverse: GACTCCACCAACCAC-CACCAG (SEQ ID NO: 3); CD62L forward: ATGGAAC-GATGACGCCTGCC (SEQ ID NO: 4), reverse: GGCCTC-CAAAGGCTCACACT (SEQ ID NO: 5); Additional primers included lymphoid enhancer-binding factor 1 (LEF1) forward: CACACCCGTCACACATCCCA (SEQ ID NO: 6), reverse: TGGGAAAACCAGCCAAGAGGTG (SEQ ID NO: 7); transcription factor 1 (TCF1) forward: TGCAGCTATACCCAGGCTGG (SEQ ID NO: 8), reverse: CCTCGACCGCCTCTTCTTC (SEQ ID NO: 9).

Human shRNA Knockdown: Total CD8+ T cells were isolated and transfected with 5 µg negative control, STAT1 shRNA, or STAT3 shRNA (Dharmacon) using Amaxa human T cell Nucleofector Kit according to the manufacturer's instructions (Lonza). Transfected cells were rested for 1-2 days and live GFP+ cells were sort-purified for immunoblot analysis or were stimulated for 7 days as previously described before further analysis.

Western Blot analysis: Equal number of cells was lysed in 2×SDS loading buffer and loaded for immunoblot analysis with different antibodies (Cell Signaling). Anti-β-actin-HRP was from Santa Cruz Biotech. β-actin was used as the loading control for all immunoblot experiments. The results were quantified using ImageJ and normalized to the density of actin in the corresponding samples.

Chromatin immunoprecipitation (ChIP): ChIP was performed using a ChIP Assay Kit according to the manufacturer's instructions (Millipore). Quantitative real-time PCR was performed with primers: CD28 promoter proximal STAT sites: forward TCTGCTGGATTTCAAGCACCC (SEQ ID NO:10), reverse GACTGCAGCATTT-CACACAGG (SEQ ID NO: 11); distal STAT sites: forward TGCTTGCACGTAGAATGGGT (SEQ ID NO: 12), reverse GGATGGGGACAGGTTGTGTC (SEQ ID NO: 13); Rabbit IgG was used as a negative control.

Chromium Release Assay (CRA): Tumor cells were labeled with Cr51 before being incubated with antigen-specific CTLs at effector:tumor of 20:1 for 4 hours. The Cr51 amount in the supernatants was measured and the killing efficiency was calculated as % killing=100%× (sample average−average of negative control)/(average of positive control−average of negative control).

Mini-REP was started scaling down from T25 flasks to 24-well plates accordingly. IL-21 and Panobinostat dose remained unchanged.

Statistical analysis: Graphical presentation and statistical analysis of the data were performed using GraphPad Prism (Version 6. GraphPad software, San Diego, CA) and Excel. Data are displayed as mean and STD. Results between experimental groups were compared using Student's t test. $p<0.05$ was considered statistically significant. Statistical significance is displayed as *$P<0.05$, $P<0.01$, *$P<0.001$.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Klebanoff et al., *Proc Natl Acad Sci USA.* 102(27):9571-6, 2005.
Li et al., *J. Immunol.* 175, 2261-2269, 2005.
Remington: The Science and Practice of Pharmacy, 22$^{nd}$ Edition, *Pharmaceutical Press.* 2013.
Seto and Yoshida, *Cold Spring Harb Perspect Biol.* 6(4): a018713, 2014.
U.S. Pat. No. 6,307,024
U.S. Pat. No. 6,686,178
Yee, *Immunol. Rev.* 257, 250-263, 2014.

What is claimed is:

1. A method for reprogramming antigen-specific effector T cells ($T_{EFF}$ cells) into central memory T cells ($T_{CM}$ cells), the method comprising:
   (a) obtaining a starting population of lymphocytes comprising $T_{EFF}$ cells from a subject; and
   (b) culturing the starting population of lymphocytes comprising $T_{EFF}$ cells or the sample enriched in $T_{EFF}$ cells in the presence of a histone deacetylase inhibitor (HDACi) and interleukin-21 (IL-21), each in an amount sufficient to re-program the $T_{EFF}$ cells into $T_{CM}$ cells,
   wherein the re-programming produces a population of lymphocytes enriched for $T_{CM}$ cells as compared to the number of $T_{CM}$ cells in the starting population of lymphocytes comprising $T_{EFF}$ cells obtained from a subject.

2. The method of claim 1, wherein the obtaining a starting population of lymphocytes comprising $T_{EFF}$ cells comprises taking a sample of tumor infiltrating lymphocytes (TILs) or a sample comprising peripheral blood mononuclear cells (PBMCs) from a subject.

3. The method of claim 1, further comprising the step of preparing a sample enriched in $T_{EFF}$ cells from the starting population of lymphocytes comprising $T_{EFF}$ cells.

4. The method of claim 3, wherein the step of preparing a sample enriched in $T_{EFF}$ cells from the starting population of lymphocytes comprising $T_{EFF}$ cells comprises isolating $CD8^+$ $T_{EFF}$ cells from the starting population of lymphocytes comprising $T_{EFF}$ cells.

5. The method of claim 4, wherein the step of preparing a sample enriched in $T_{EFF}$ cells from the starting population of lymphocytes comprising $T_{EFF}$ cells further comprises depleting the starting population of lymphocytes comprising $T_{EFF}$ cells of myeloid-derived suppressor cells (MDSCs), TREGs, NK cells, and macrophages.

6. The method of claim 5, wherein the $CD8^+$ $T_{EFF}$ cells express CD45RO.

7. The method of claim 6, wherein the $CD8^+$ $T_{EFF}$ cells are cultured in the presence of an HDACi prior to adding IL-21.

8. The method of claim 6, wherein the $CD8^+$ $T_{EFF}$ cells are cultured in the presence of IL-21 prior to adding an HDACi.

9. The method of claim 6, wherein the $CD8^+$ $T_{EFF}$ cells are simultaneously cultured in the presence of an HDACi and IL-21.

10. The method of claim 1, wherein the IL-21 is present at a concentration of 10 ng/mL to 50 ng/mL.

11. The method of claim 1, wherein the HDACi is present at a concentration of 1 nM to 5 nM.

12. The method of claim 1, wherein the IL-21 is present at a concentration of 20 ng/mL to 40 ng/mL and the HDACi is present at a concentration of 2 nM of 4 nM.

13. The method claim 1, wherein the HDACi is a classical HDACi.

14. The method of claim 13, wherein the classical HDACi is selected from the group consisting of trichostatin A, trapoxin B, phenylbutyrate, valproic acid, vorinostat (suberanilohydroxamic acid or SAHA), belinostat (PXD101), panobinostat, dacinostat (LAQ824), entinostat (SNDX-275 or MS-275), tacedinaline (C1994), and mocetinostat (MGCD0103).

15. The method of claim 14, wherein the HDACi is SAHA.

16. The method of claim 15, wherein the HDAC is panobinostat.

17. The method of claim 1, wherein the resulting $T_{CM}$ cells are $CD8^+$ and also express at least two of CD45RO, CD28, CD62L, and CCR7.

18. The method of claim 17, wherein the resulting $T_{CM}$ cells also express increased levels of granzyme B and perforin 1.

19. The method of claim 1, further comprising a step of contacting the starting population of lymphocytes comprising $T_{EFF}$ cells or the sample enriched in $T_{EFF}$ cells with IL-2 prior to or concurrently with the step of culturing the starting population of lymphocytes comprising $T_{EFF}$ cells or the sample enriched in $T_{EFF}$ cells in the presence of an HDACi and IL-21, each in an amount sufficient to re-program the $T_{EFF}$ cells into $T_{CM}$ cells.

20. The method of claim 1, wherein the population of lymphocytes enriched for $T_{CM}$ cells comprises at least 5-fold more $T_{CM}$ cells than in the starting population of lymphocytes comprising $T_{EFF}$ cells.

21. A method of treating cancer in a subject comprising administering a therapeutically effective amount of the population of lymphocytes enriched for $T_{CM}$ cells produced by the method of claim 1 to the subject.

22. A method for generating $T_{CM}$ cells from $T_{EFF}$ cells comprising:
   (a) obtaining a starting population of lymphocytes comprising $T_{EFF}$ cells from a subject;
   (b) simultaneously adding an HDACi at a concentration between 2 nM and 4 nM and IL-21 at a concentration between 20 ng/mL and 40 ng/mL to the starting population of lymphocytes comprising $T_{EFF}$ cells; and
   (c) culturing the starting population of lymphocytes comprising $T_{EFF}$ cells for 12 to 16 days, thereby re-programming the $T_{EFF}$ cells to produce a population of lymphocytes enriched for $T_{CM}$ cells as compared to the number of $T_{CM}$ cells in the starting population of lymphocytes comprising $T_{EFF}$ cells.

23. A composition comprising a population of human central memory-like $CD8^+$ T cells, wherein at least 20% of the T cells are $CD28^+CD62L^+CD127^-CCR7^-$ T cells.

* * * * *

UNITED STATES PATENT AND TRADEMARK OFFICE
CERTIFICATE OF CORRECTION

PATENT NO. : 12,173,317 B2  
APPLICATION NO. : 17/042022  
DATED : December 24, 2024  
INVENTOR(S) : Yee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1098 days.

Signed and Sealed this  
Eighth Day of April, 2025

Coke Morgan Stewart  
*Acting Director of the United States Patent and Trademark Office*

SEQUENCE LISTING

```
<160> NUMBER OF SEQ ID NOS: 13

<210> SEQ ID NO 1
<211> LENGTH: 162
<212> TYPE: PRT
<213> ORGANISM: Homo sapiens

<400> SEQUENCE: 1

Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110
```

```
Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ctcacacttc gggttcctcg g                                              21

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
gactccacca accaccacca g                                              21

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
atggaacgat gacgcctgcc                                                20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ggcctccaaa ggctcacact                                                20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cacacccgtc acacatccca                                                20

<210> SEQ ID NO 7
<211> LENGTH: 22
<212> TYPE: DNA
<213> ORGANISM: Artificial Sequence
<220> FEATURE:
<223> OTHER INFORMATION: Primer
```

-continued

```
<400> SEQUENCE: 7
tgggaaaacc agccaagagg tg                                      22

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tgcagctata cccaggctgg                                         20

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
cctcgaccgc ctcttcttc                                          19

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tctgctggat ttcaagcacc c                                       21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gactgcagca tttcacacag g                                       21

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tgcttgcacg tagaatgggt                                         20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ggatggggac aggttgtgtc                                         20
```